(12) United States Patent
Goto et al.

(10) Patent No.: US 6,827,688 B2
(45) Date of Patent: Dec. 7, 2004

(54) BLOOD PRESSURE MONITOR

(75) Inventors: Masami Goto, Aichi-ken (JP); Hideo Nishibayashi, Inuyama (JP); Kiyoyuki Narimatsu, Kasugai (JP); Akihiro Yokozeki, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 0 days.

(21) Appl. No.: 10/337,987

(22) Filed: Jan. 8, 2003

(65) Prior Publication Data

US 2003/0092999 A1 May 15, 2003

Related U.S. Application Data

(62) Division of application No. 09/892,581, filed on Jun. 28, 2001, which is a division of application No. 09/397,666, filed on Sep. 16, 1999, now Pat. No. 6,283,922, which is a division of application No. 09/152,464, filed on Sep. 14, 1998, now Pat. No. 6,007,492, which is a division of application No. 08/740,126, filed on Oct. 24, 1996, now Pat. No. 5,860,932.

(51) Int. Cl.$^7$ .............................................. A61B 5/00
(52) U.S. Cl. ....................... 600/485; 600/490; 600/500
(58) Field of Search ................................ 600/485, 490, 600/493–6, 500–3

(56) References Cited

U.S. PATENT DOCUMENTS

| | | | |
|---|---|---|---|
| 5,000,187 A | | 3/1991 | Higuchi et al. |
| 5,131,391 A | | 7/1992 | Sakai et al. |
| 5,203,341 A | | 4/1993 | Souma |
| 5,261,414 A | * | 11/1993 | Aung et al. ................. 600/496 |
| 5,279,303 A | | 1/1994 | Kawamura et al. |
| 5,533,511 A | | 7/1996 | Kaspari et al. |
| 5,551,440 A | | 9/1996 | Miyawaki |
| 5,653,241 A | * | 8/1997 | Harada et al. ............... 600/493 |
| 5,671,750 A | | 9/1997 | Shinoda |
| 5,699,807 A | | 12/1997 | Motogi et al. |
| 5,743,856 A | | 4/1998 | Oka et al. |
| 5,743,857 A | | 4/1998 | Shinoda et al. |
| 5,830,149 A | * | 11/1998 | Oka et al. .................... 600/500 |

FOREIGN PATENT DOCUMENTS

EP 655219 A1 5/1995

(List continued on next page.)

Primary Examiner—Robert L. Nasser
(74) Attorney, Agent, or Firm—Oliff & Berridge, PLC

(57) ABSTRACT

A blood pressure monitor including a cuff, a pressure sensor which detects a pressure in the cuff, a pressure regulating device which increases the pressure of the cuff, a pulse-amplitude determining device for determining an amplitude of each of pulses of a pulse wave which are produced in the cuff and detected by the pressure sensor while the cuff pressure is increased, a candidate determining device for determining, as a diastolic BP candidate, a pressure of the cuff which is detected by the pressure sensor and which corresponds to an amplitude of a first pulse of the pulses determined by the pulse-amplitude determining device, by judging whether the amplitude of the first pulse is not greater than a reference value which is smaller than an amplitude of at least one second pulse of the pulses, by a predetermined proportion of the amplitude of the second pulse, the amplitude of the second pulse being determined by the pulse-amplitude determining device after the amplitude of the first pulse is determined, and a BP determining device for determining, as a monitor diastolic BP value, the cuff pressure corresponding to the amplitude of the first pulse, when the candidate determining device determines, as the diastolic BP candidate, the cuff pressure corresponding to the amplitude of the first pulse, with respect to a predetermined number of the one or more second pulses.

1 Claim, 26 Drawing Sheets

FOREIGN PATENT DOCUMENTS

| | | |
|---|---|---|
| EP | 696433 A1 | 2/1996 |
| EP | 698370 A2 | 2/1996 |
| JP | A-50-128387 | 10/1975 |
| JP | A-60-241422 | 11/1985 |
| JP | A-61-103432 | 5/1986 |
| JP | 62-183742 | 8/1987 |
| JP | 64-017628 | 1/1989 |
| JP | A-1-214338 | 8/1989 |
| JP | 02-082309 | 3/1990 |
| JP | U-2-82309 | 6/1990 |
| JP | 03-007137 | 1/1991 |
| JP | A-5-115445 | 5/1993 |
| JP | 05-269092 | 10/1993 |

* cited by examiner

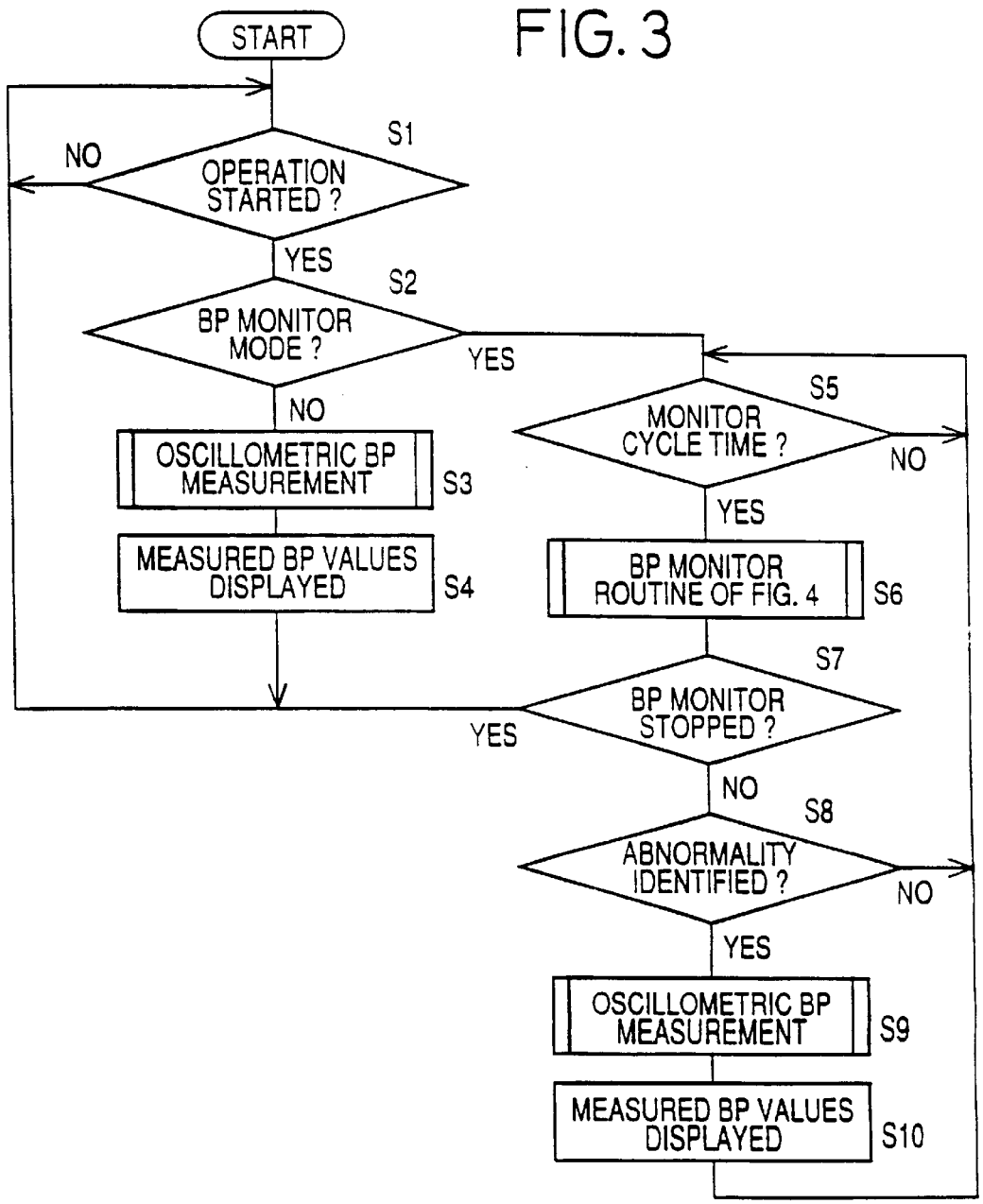

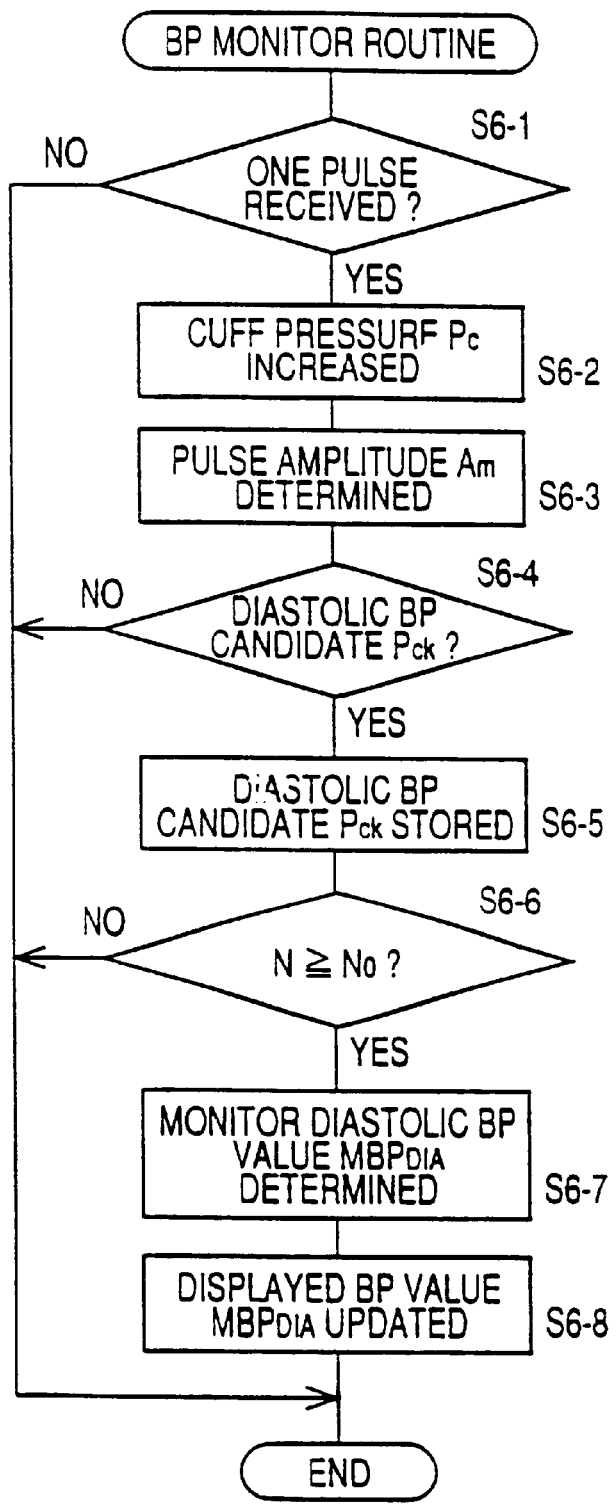

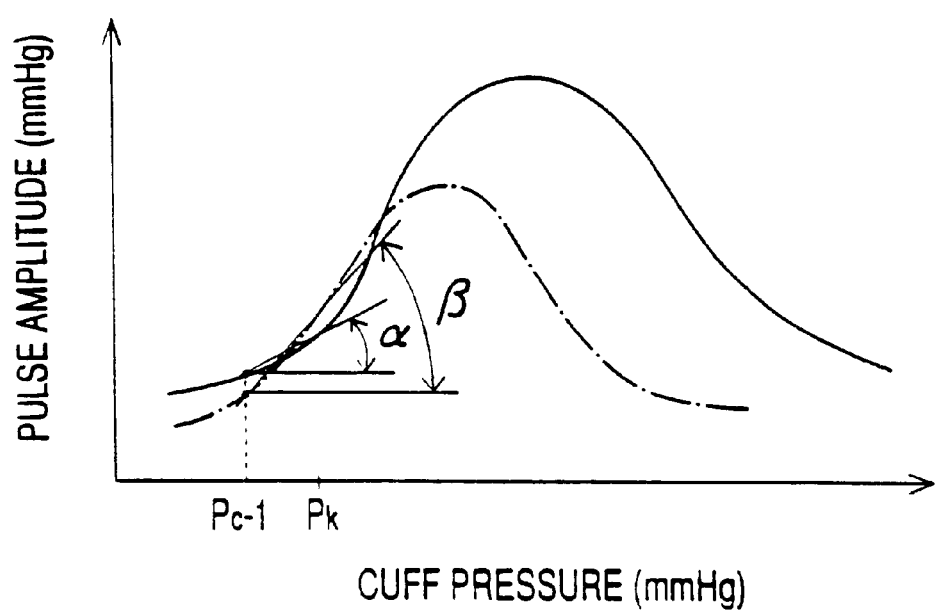

BLOOD PRESSURE MONITOR

This application is a Divisional of application of prior pending Application No. 09/892,581 filed Jun. 28, 2001, which is a Divisional Application of prior pending Application No. 09/397,666 filed Sep. 16, 1999 and issued as U.S. Pat. No. 6,283,922, which is a Divisional application of prior pending Application No. 09/152,464, filed Sep. 14, 1998 and issued U.S. Pat. No. 6,007,492, which is a Divisional Application of prior pending Application No. 08/740,126 filed Oct. 24, 1996 and issued as U.S. Pat. No. 5,860,932.

BACKGROUND OF THE INVENTION

1. Field of the Invention

The present invention relates to a blood pressure monitor including an inflatable cuff.

2. Related Art Statement

There is known a blood pressure (BP) monitor which includes an inflatable cuff adapted to be wound around a body portion, e.g., upper arm, of a living subject, e.g., patient, to press the body portion. The BP monitor functions as an automatic BP measuring device which periodically measures a BP value of the subject by increasing the cuff pressure and thereby pressing the body portion of the subject. However, if the period or interval of the BP measurements effected by the BP monitor is shortened for improving the accuracy of monitoring of subject's blood pressure, the frequency of pressing of subject's body portion is increased, which causes the subject to feel discomfort.

In the above-indicated background, it has been proposed to increase the pressure of an inflatable cuff being wound around a body portion of a living subject, up to a predetermined value, detect a pulse wave that is a pressure oscillation produced in the cuff, and estimate a BP value of the subject based on the magnitude of the pulse wave. This technique is disclosed in, e.g., Japanese Patent Application laid open for inspection purposes under Publication No. 61(1986)-103432, or Japanese Patent Application laid open for inspection purposes under Publication No. 60(1985)-241422.

Regarding the above-indicated conventional BP monitor techniques, however, there are known some cases where it is difficult to detect a change of magnitudes of pulse waves which reflects a change of blood pressure of a living subject, if BP values are estimated based on the pulse waves detected at a considerably low cuff pressure, which contributes to reducing the discomfort felt by the subject. More specifically described, respective amplitudes of pulses of a pulse wave which is detected from an inflatable cuff being wound around a body portion of a living subject whose blood pressure is normal, has an envelope indicated at solid line in the graph of FIG. 6. In contrast, amplitudes of pulses of a pulse wave obtained from a living subject whose blood pressure is low, has an envelope indicated at one-dot chain line in FIG. 6. In the case where amplitudes of pulses of a pulse wave are detected at a considerably low cuff pressure, e.g., pressure, $P_K$, in FIG. 6, an amount of change of the pulse amplitudes with respect to an amount of change of blood pressure of a living subject may be too small. Thus, when the BP monitor is used at the low cuff pressure $P_K$, it may not be able to monitor the blood pressure of the subject with high accuracy.

There is also known a continuous BP monitor which includes an inflatable cuff which is adapted to be wound around a body portion of a living subject to press the body portion; a blood pressure measuring device which measures a blood pressure of the subject by changing a pressure in the cuff; a pressure pulse wave sensor which is adapted to be pressed against a distal section of the artery located on a distal side of the cuff wound around the body portion, so as to detect a pressure pulse wave which is produced from the distal section of the artery; a relationship determining means which determines a relationship between blood pressure and magnitude of pressure pulse wave, based on the blood pressure measured by the blood pressure measuring device and a magnitude of the pressure pulse wave detected by the pressure pulse wave sensor; a blood pressure determining means which successively determines a blood pressure of the subject according to the determined relationship based on a magnitude of each of successive heartbeat-synchronous pulses of the pressure pulse wave detected by the pressure pulse wave sensor; and a display which displays the blood pressure values determined by the blood pressure determining means. This BP monitor is disclosed in, e.g., Japanese Patent Application laid open for inspection purposes under Publication No. 1(1989)-214338 or Japanese Utility Model Application laid open for inspection purposes under Publication No. 2(1990)-82309.

In the prior continuous BP monitor, the condition under which the pressure pulse wave sensor is pressed against subject's artery may be changed due to, e.g., a physical motion of the subject. Hence, in order to improve the accuracy of BP values determined by the BP determining means, the relationship between blood pressure and magnitude of pressure pulse wave is updated at a predetermined period. However, the updating of the relationship needs a blood pressure measurement of the blood pressure measuring device including the inflation of the cuff. In addition, since the pressure pulse wave sensor is set on the distal side of the cuff, the continuous BP determination of the BP determining means is interrupted by the inflation of the cuff. This problem is exaggerated if the period of updating of the relationship is shortened for improving the accuracy of the continuous BP monitoring.

SUMMARY OF THE INVENTION

It is a first object of the present invention to provide a blood pressure monitor which includes an inflatable cuff and which monitors with high accuracy the blood pressure of a living subject without causing the subject to feel discomfort.

It is a second object of the present invention to provide a continuous blood pressure monitor which includes an inflatable cuff and which continuously monitors the blood pressure of a living subject with reduced discomfort felt by the subject and with reduced interruption frequency.

The first object may be achieved according to a first aspect of the present invention, which provides a blood pressure monitor including an inflatable cuff which is adapted to be wound around a body portion of a living subject to press the body portion, a pressure sensor which detects a pressure in the cuff, a cuff-pressure regulating device which increases the pressure of the cuff, pulse-amplitude determining means for determining an amplitude of each of pulses of a pulse wave which are produced in the cuff and detected by the pressure sensor while the pressure of the cuff is increased by the cuff-pressure regulating device, candidate determining means for determining, as a diastolic blood pressure candidate, a pressure of the cuff which is detected by the pressure sensor and which corresponds to an amplitude of a first pulse of the pulses determined by the pulse-amplitude determining means, by judging whether the amplitude of the first pulse is not greater than a reference value which is smaller than an amplitude of at least one second pulse of the pulses, by a predetermined proportion of the amplitude of the second pulse, the amplitude of the second pulse being determined by the pulse-amplitude determining means after the amplitude of the first pulse is determined, and blood-pressure determining means for determining, as a monitor diastolic blood pressure value, the pressure of the cuff corresponding to the amplitude of the first pulse, when the candidate determining means determines, as the diastolic blood pressure candidate, the pressure of the cuff corresponding to the amplitude of the first pulse, with respect to a predetermined number of the at least one second pulse.

In the blood pressure (BP) monitor in accordance with the first aspect of the invention, the predetermined number may be one, two, or a greater number. For example, the predetermined number is three. Thus, the present BP monitor may determine a monitor diastolic BP value of a living subject at a pressure level which is higher than the diastolic BP value and which corresponds to the "third" one of the subsequent pulses determined after the initial pulse. The thus determined monitor diastolic BP value enjoys high accuracy. In addition, since the pressure level where the monitor diastolic BP value is determined is considerably low, the subject does not feel discomfort.

According to a preferred feature of the first aspect of the invention, the candidate determining means comprises judging means for judging whether the amplitude of the first pulse is not greater than a reference value which is smaller than an amplitude of each of a plurality of second pulses of the pulses, by a predetermined proportion of the amplitude of the each second pulse, the respective amplitudes of the second pulses being determined by the pulse-amplitude determining means after the amplitude of the first pulse is determined.

According to another feature of the first aspect of the invention, the cuff-pressure regulating device comprises pressure increasing means for stepwise increasing the pressure of the cuff by alternately increasing the cuff pressure and maintaining the cuff pressure at each of a plurality of different pressure values, and the pulse-amplitude determining means determines an amplitude of at least one pulse which is produced in the cuff and detected by the pressure sensor while the cuff pressure is maintained at the each pressure value. The pressure increasing means may increase the cuff pressure by a constant pressure increase amount, for each time or step, or may increase the cuff pressure by an increase amount which is variable depending upon the current cuff pressure. The pulse-amplitude determining means may determine an amplitude of a single pulse detected by the pressure sensor while the cuff pressure is maintained at each pressure value, or an average of respective amplitudes of two or more pulses detected while the cuff pressure is maintained at each pressure value. The thus determined pulse amplitude or amplitudes enjoy high accuracy because they are free from adverse influences resulting from the increasing of the cuff pressure. Therefore, the monitor diastolic BP values of the subject are determined with accuracy based on the pulse amplitudes.

According to another feature of the first aspect of the invention, the blood-pressure determining means comprises monitor means for iteratively determining the monitor diastolic blood pressure value. The monitor means may periodically determine the monitor diastolic blood pressure value at a predetermined period or interval of time (i.e., monitor cycle time).

According to another feature of the first aspect of the invention, the BP monitor further comprises abnormality identifying means for identifying an abnormality of the monitor diastolic blood pressure values iteratively determined by the monitor means.

According to another feature of the first aspect of the invention, the abnormality identifying means comprises means for identifying the abnormality based on at least one of an amount of change of a last determined value of the monitor diastolic blood pressure values from an average of the monitor diastolic blood pressure values, and a rate of change of the last determined value of the monitor diastolic blood pressure values from the average of the monitor diastolic blood pressure values.

According to another feature of the first aspect of the invention, the BP monitor further comprising a blood pressure measuring device which increases the pressure of the cuff up to a target pressure which is higher than a systolic blood pressure of the subject and measures at least one of a systolic, a mean, and a diastolic blood pressure value of the living subject based on a variation of respective amplitudes of pulses of a pulse wave which are produced in the cuff and detected by the pressure sensor during at least one of the increasing of the cuff pressure up to the target pressure and a decreasing of the cuff pressure down from the target pressure. The target pressure may be, e.g., about 180 mmHg that is estimated to be sufficiently higher than a normal systolic BP value of a human being.

According to another feature of the first aspect of the invention, the blood pressure measuring device comprises means for measuring the at least one of the systolic, the mean, and the diastolic blood pressure value of the living subject when the abnormality identifying means identifies the abnormality.

According to another feature of the first aspect of the invention, the BP monitor further comprising a display which displays the monitor diastolic blood pressure value determined by the blood-pressure determining means.

The second object may be achieved according to a second aspect of the present invention, which provides a blood pressure monitor comprising an inflatable cuff which is adapted to be wound around a body portion of a living subject to press the body portion through which an artery of the subject extends; a blood pressure measuring device which measures a blood pressure of the subject by changing a pressure in the cuff; a pressure pulse wave sensor which is adapted to be pressed against a distal section of the artery located on a distal side of the cuff wound around the body portion, so as to detect a pressure pulse wave which is produced from the distal section of the artery and is propagated thereto via a skin tissue above the distal section; relationship determining means for determining a relationship between blood pressure and magnitude of pressure pulse wave, based on the blood pressure measured by the blood pressure measuring device and a magnitude of the pressure pulse wave detected by the pressure pulse wave sensor; blood pressure determining means for successively determining at least a diastolic blood pressure of the subject according to the determined relationship based on a magnitude of a lower-peak point of each of successive first heartbeat-synchronous pulses of the pressure pulse wave detected by the pressure pulse wave sensor; cuff-pressure increasing means for increasing the pressure of the cuff at a predetermined rate; waveform-characteristic determining means for determining a characteristic of a lower-peak portion of a waveform of each of successive second heartbeat-synchronous pulses of the pressure pulse wave which are detected by the pressure pulse wave sensor when the pressure of the cuff is increased at the predetermined rate by the cuff-pressure increasing means, the lower-peak portion including a lower-peak point of the each second heartbeat-synchronous pulse; and judging means for judging whether the determined relationship is accurate, based on at least one diastolic blood pressure determined by the blood pressure determining means and a pressure of the cuff corresponding to a time when the waveform characteristics determined by the waveform-characteristic determining means significantly largely change.

In the blood pressure monitor in accordance with the second aspect of the invention, if the judging means makes a positive judgment, the relationship need not be updated. Accordingly, the blood pressure measuring device does not inflate the cuff, and the subject is prevented from being pressed by the cuff. In addition, although the pressure pulse wave sensor is set on the distal side of the cuff, the blood pressure determining means can continue to successively determine blood pressure values according to the relationship based on the pressure pulse wave detected by the pressure pulse wave sensor.

The second object may be achieved according to a third aspect of the present invention, which provides a blood pressure monitor comprising an inflatable cuff which is adapted to be wound around a body portion of a living subject to press the body portion through which an artery of the subject extends; a blood pressure measuring device which measures a blood pressure of the subject by changing a pressure in the cuff; a pressure pulse wave sensor which is adapted to be pressed against a distal section of the artery located on a distal side of the cuff wound around the body portion, so as to detect a pressure pulse wave which is produced from the distal section of the artery and is propagated thereto via a skin tissue above the distal section; relationship determining means for determining a relationship between blood pressure and magnitude of pressure pulse wave, based on the blood pressure measured by the blood pressure measuring device and a magnitude of the pressure pulse wave detected by the pressure pulse wave sensor; blood pressure determining means for determining at least a diastolic blood pressure of the subject according to the determined relationship based on a magnitude of a lower-peak point of each of successive first heartbeat-synchronous pulses of the pressure pulse wave detected by the pressure pulse wave sensor; cuff-pressure increasing means for increasing the pressure of the cuff at a predetermined rate; a cuff pulse wave sensor which detects a cuff pulse wave which is a pressure oscillation produced in the cuff; phase-difference determining means for determining a phase difference of respective lower-peak points of each of successive second heartbeat-synchronous pulses of the pressure pulse wave and a corresponding one of successive heartbeat-synchronous pulses of the cuff pulse wave, the second heartbeat-synchronous pulses of the pressure pulse wave and the heartbeat-synchronous pulses of the cuff pulse wave being detected by the pressure pulse wave sensor and the cuff pulse wave sensor, respectively, when the pressure of the cuff is increased at the predetermined rate by the cuff-pressure increasing means; and judging means for judging whether the determined relationship is accurate, based on at least one diastolic blood pressure determined by the blood pressure determining means and a pressure of the cuff corresponding to a time when the phase differences determined by the phase-difference determining means significantly largely change.

In the blood pressure monitor in accordance with the third aspect of the invention, if the judging means makes a positive judgment, the relationship need not be updated. Accordingly, the blood pressure measuring device does not inflate the cuff, and the subject is prevented from being pressed by the cuff. In addition, although the pressure pulse wave sensor is set on the distal side of the cuff, the blood pressure determining means can continue to successively determine blood pressure values according to the relationship based on the pressure pulse wave detected by the pressure pulse wave sensor.

The second object may be achieved according to a fourth aspect of the present invention, which provides a blood pressure monitor comprising an inflatable cuff which is adapted to be wound around a body portion of a living subject to press the body portion through which an artery of the subject extends; a blood pressure measuring device which measures a blood pressure of the subject by changing a pressure in the cuff; a pressure pulse wave sensor which is adapted to be pressed against a distal section of the artery located on a distal side of the cuff wound around the body portion, so as to detect a pressure pulse wave which is produced from the distal section of the artery and is propagated thereto via a skin tissue above the distal section; relationship determining means for determining a relationship between blood pressure and magnitude of pressure pulse wave, based on the blood pressure measured by the blood pressure measuring device and a magnitude of the pressure pulse wave detected by the pressure pulse wave sensor; blood pressure determining means for determining at least a mean blood pressure of the subject according to the determined relationship based on a mean magnitude of each of successive first heartbeat-synchronous pulses of the pressure pulse wave detected by the pressure pulse wave sensor; cuff-pressure increasing means for increasing the pressure of the cuff at a predetermined rate; pulse-area calculating means for calculating an area defined by each of successive second heartbeat-synchronous pulses of the pressure pulse wave which are detected by the pressure pulse wave sensor when the pressure of the cuff is increased at the predetermined rate by the cuff-pressure increasing means; half-area identifying means for identifying that the pulse areas calculated by the pulse-area calculating means have decreased to half an initial pulse area obtained before the cuff-pressure increasing means starts increasing the pressure of the cuff; and judging means for judging whether the determined relationship is accurate, based on at least one mean blood pressure determined by the blood pressure determining means and a pressure of the cuff corresponding to a time when the half-area identifying means identifies that the pulse areas calculated by the pulse-area calculating means have decreased to half the initial pulse area.

In the blood pressure monitor in accordance with the fourth aspect of the invention, if the judging means makes a positive judgment, the relationship need not be updated. Accordingly, the blood pressure measuring device does not inflate the cuff, and the subject is prevented from being pressed by the cuff. In addition, although the pressure pulse wave sensor is set on the distal side of the cuff, the blood pressure determining means can continue to successively determine blood pressure values according to the relationship based on the pressure pulse wave detected by the pressure pulse wave sensor.

The second object may be achieved according to a fifth aspect of the present invention, which provides a blood pressure monitor comprising an inflatable cuff which is adapted to be wound around a body portion of a living subject to press the body portion through which an artery of the subject extends; a blood pressure measuring device which measures a blood pressure of the subject by changing a pressure in the cuff; a pressure pulse wave sensor which is adapted to be pressed against a distal section of the artery located on a distal side of the cuff wound around the body portion, so as to detect a pressure pulse wave which is produced from the distal section of the artery and is propagated thereto via a skin tissue above the distal section; relationship determining means for determining a relationship between blood pressure and magnitude of pressure pulse wave, based on the blood pressure measured by the blood pressure measuring device and a magnitude of the pressure pulse wave detected by the pressure pulse wave sensor; blood pressure determining means for determining a blood pressure of the subject according to the determined relationship based on a magnitude of each of successive first heartbeat-synchronous pulses of the pressure pulse wave detected by the pressure pulse wave sensor; cuff-pressure regulating means for increasing the pressure of the cuff up to a predetermined value and holding the cuff pressure at the predetermined value; pulse-area calculating means for calculating an area defined by each of successive second heartbeat-synchronous pulses of the pressure pulse wave which are detected by the pressure pulse wave sensor when the cuff pressure is held at the predetermined value by the cuff-pressure regulating means; and judging means for judging whether the determined relationship is accurate, based on a ratio of the calculated area of at least one the second heartbeat-synchronous pulse of the pressure pulse wave detected by the pressure pulse wave when the cuff pressure is held at the predetermined value by the cuff-pressure regulating means, to an initial pulse area obtained before the cuff-pressure regulating means starts increasing the cuff pressure.

In the blood pressure monitor in accordance with the fifth aspect of the invention, if the judging means makes a positive judgment, the relationship need not be updated. Accordingly, the blood pressure measuring device does not inflate the cuff, and the subject is prevented from being pressed by the cuff. In addition, although the pressure pulse wave sensor is set on the distal side of the cuff, the blood pressure determining means can continue to successively determine blood pressure values according to the relationship based on the pressure pulse wave detected by the pressure pulse wave sensor.

The first object may be achieved according to a sixth aspect of the present invention, which provides a blood pressure monitor comprising an inflatable cuff which is adapted to be wound around a body portion of a living subject to press the body portion through which an artery of the subject extends; a blood pressure measuring device which measures a blood pressure of the subject by changing a pressure in the cuff; a cuff pulse wave sensor which detects a cuff pulse wave which is a pressure oscillation produced in the cuff; a distal pulse wave sensor which detects a distal pulse wave from a distal section of the artery located on a distal side of the cuff wound around the body portion; cuff-pressure increasing means for increasing the pressure of the cuff at a predetermined rate; first peak-interval determining means for determining a first interval between an upper-peak point and a lower-peak point of each of first heartbeat-synchronous pulses of the distal pulse wave which are detected by the distal pulse wave sensor when the pressure of the cuff is increased at the predetermined rate by the cuff-pressure increasing means; second peak-interval determining means for determining a second interval between an upper-peak point and a lower-peak point of each of second heartbeat-synchronous pulses of the cuff pulse wave which are detected by the cuff pulse wave sensor when the pressure of the cuff is increased at the predetermined rate by the cuff-pressure increasing means; difference determining means for determining a difference between the first interval of the each of the first heartbeat-synchronous pulses and the second interval of a corresponding one of the second heartbeat-synchronous pulses; and blood pressure determining means for determining, as a diastolic blood pressure of the subject, a pressure of the cuff corresponding to a time when the differences determined by the difference determining means significantly largely change.

In the blood pressure monitor in accordance with the sixth aspect of the invention, the upper-peak and lower-peak points of each pulse of the cuff pressure wave are not influenced by the increasing of the cuff pressure, whereas the upper-peak and lower-peak points of each pulse of the distal pulse wave are influenced by the increasing of the cuff pressure, because the distal pulse wave sensor is set on the distal side of the cuff. Therefore, the peak-interval differences are influenced by the increasing of the cuff pressure. The Inventors have found that the phase of the distal pulse wave has a certain relationship with that of the cuff pulse wave and that this relationship significantly largely changes when the cuff pressure becomes equal to a diastolic pressure of the subject. Thus, a cuff pressure corresponding to the time when the peak-interval differences significantly largely change, can be determined as a diastolic pressure of the subject. In the case where a physiological change such as arrhythmia occurs to the heart of the patient, respective waveforms of the cuff pulse wave and the distal pulse wave change in a similar manner, therefore the peak-interval differences are not influenced by this change. Thus, the diastolic BP value of the subject can be determined with high accuracy. The distal pulse wave sensor may be provided by a sensor employed for a different purpose from monitoring the blood pressure of the subject. In this case, the total number of sensors which are worn on the subject is reduced as compared with the case where an exclusive distal pulse wave sensor is employed. Although the distal pulse wave sensor is worn at a position downstream of the cuff, a measurement using the distal pulse wave sensor, different from the blood pressure measurement, can be continued without being interrupted due to the inflation of the cuff, because in a BP monitoring operation the cuff pressure is not increased to values higher than the diastolic pressure of the subject.

According to a preferred feature of the sixth aspect of the invention, the distal pulse sensor comprises a pressure pulse wave sensor which is adapted to be pressed against the distal section of the artery via a skin tissue above the distal section, so as to detect a pressure pulse wave which is produced from the distal section and is propagated thereto via the skin tissue.

According to another feature of the sixth aspect of the invention, the distal pulse senior comprises a photoelectric pulse wave sensor which emits a plurality of lights having different wavelengths toward the distal section of the artery via a skin tissue above the distal section, and detects a photoelectric pulse wave representing respective intensities of the lights reflected from the distal section via the skin tissue or transmitted through the body portion. The photoelectric pulse wave sensor may be employed for measuring a peripheral blood circulation or a blood oxygen saturation of a living subject. The manner of measurement of peripheral blood circulation is disclosed in, e.g., Japanese Patent Application laid open for inspection purposes under Publication No. 5(1993)-115445, and the manner of measurement of blood oxygen saturation is disclosed in, e.g., Japanese Patent Application laid open for inspection purposes under Publication No. 50(1975)-128387.

The second object may be achieved according to a seventh aspect of the present invention, which provides a blood pressure monitor comprising an inflatable cuff which is adapted to be wound around a body portion of a living subject to press the body portion through which an artery of the subject extends; a blood pressure measuring device which measures a blood pressure of the subject by changing a pressure in the cuff; a pressure pulse wave sensor which is adapted to be pressed against a distal section of the artery located on a distal side of the cuff wound around the body portion, so as to detect a pressure pulse wave which is produced from the distal section of the artery and is propagated thereto via a skin tissue above the distal section; relationship determining means for determining a relationship between blood pressure and magnitude of pressure pulse wave, based on the blood pressure measured by the blood pressure measuring device and a magnitude of the pressure pulse wave detected by the pressure pulse wave sensor; blood pressure determining means for determining at least a diastolic blood pressure of the subject according to the determined relationship based on a magnitude of a lower-peak point of each of successive first heartbeat-synchronous pulses of the pressure pulse wave detected by the pressure pulse wave sensor; cuff-pressure increasing means for increasing the pressure of the cuff at a predetermined rate; a cuff pulse wave sensor which detects a cuff pulse wave which is a pressure oscillation produced in the cuff; first peak-interval determining means for determining a first interval between an upper-peak point and a lower-peak point of each of first heartbeat-synchronous pulses of the distal pulse wave which are detected by the distal pulse wave sensor when the pressure of the cuff is increased at the predetermined rate by the cuff-pressure increasing means; second peak-interval determining means for determining a second interval between an upper-peak point and a lower-peak point of each of second heartbeat-synchronous pulses of the cuff pulse wave which are detected by the cuff pulse wave sensor when the pressure of the cuff is increased at the predetermined rate by the cuff-pressure increasing means; difference determining means for determining a difference between the first interval of the each of the first heartbeat-synchronous pulses and the second interval of a corresponding one of the second heartbeat-synchronous pulses; and judging means for judging whether the determined relationship is accurate, based on at least one diastolic blood pressure determined by the blood pressure determining means and a pressure of the cuff corresponding to a time when the differences determined by the difference determining means significantly largely change.

In the blood pressure monitor in accordance with the seventh aspect of the invention, if the judging means makes a positive judgment, the relationship need not be updated. Accordingly, the blood pressure measuring device does not inflate the cuff, and the subject is prevented from being pressed by the cuff. In addition, although the pressure pulse wave sensor is set on the distal side of the cuff, the blood pressure determining means can continue to successively determine blood pressure values according to the relationship based on the pressure pulse wave detected by the pressure pulse wave sensor. Moreover, the accuracy of the relationship is judged by increasing the cuff pressure up to a value around the diastolic BP value of the patient, which does not cause the patient to feel discomfort.

According to a preferred feature of the seventh aspect of the invention, the blood pressure monitor further comprises a control device which controls, when the judging means makes a negative judgment, the blood pressure measuring means to measure another blood pressure of the subject, controls the pulse wave sensor to detect another magnitude of the pressure pulse wave sensor, and controls the relationship determining means to determine another relationship between blood pressure and magnitude of pressure pulse wave, based on the another blood pressure measured by the blood pressure measuring device and the another magnitude of the pressure pulse wave detected by the pressure pulse wave sensor.

BRIEF DESCRIPTION OF THE DRAWINGS

The above and optional objects, features, and advantages of the present invention will better be understood by reading the following detailed description of the preferred embodiments of the invention when considered in conjunction with the accompanying drawings, in which:

FIG. 3 is a flow chart representing a main routine which is executed by a control device of the BP monitor of FIG. 1;

FIG. 4 is a flow chart representing a BP monitor routine as a step of the flow chart of FIG. 3;

FIG. 6 is a graph showing the envelope of pulse amplitudes obtained by changing cuff pressure applied to a living subject having a normal blood pressure, and the envelope of pulse amplitudes obtained by changing cuff pressure applied to a living subject having a low blood pressure;

DETAILED DESCRIPTION OF THE PREFERRED EMBODIMENTS

Referring to FIGS. 1 through 4 and FIGS. 5A and 5B, there will be described a blood pressure (BP) monitor to which the present invention is applied.

Figure 1:
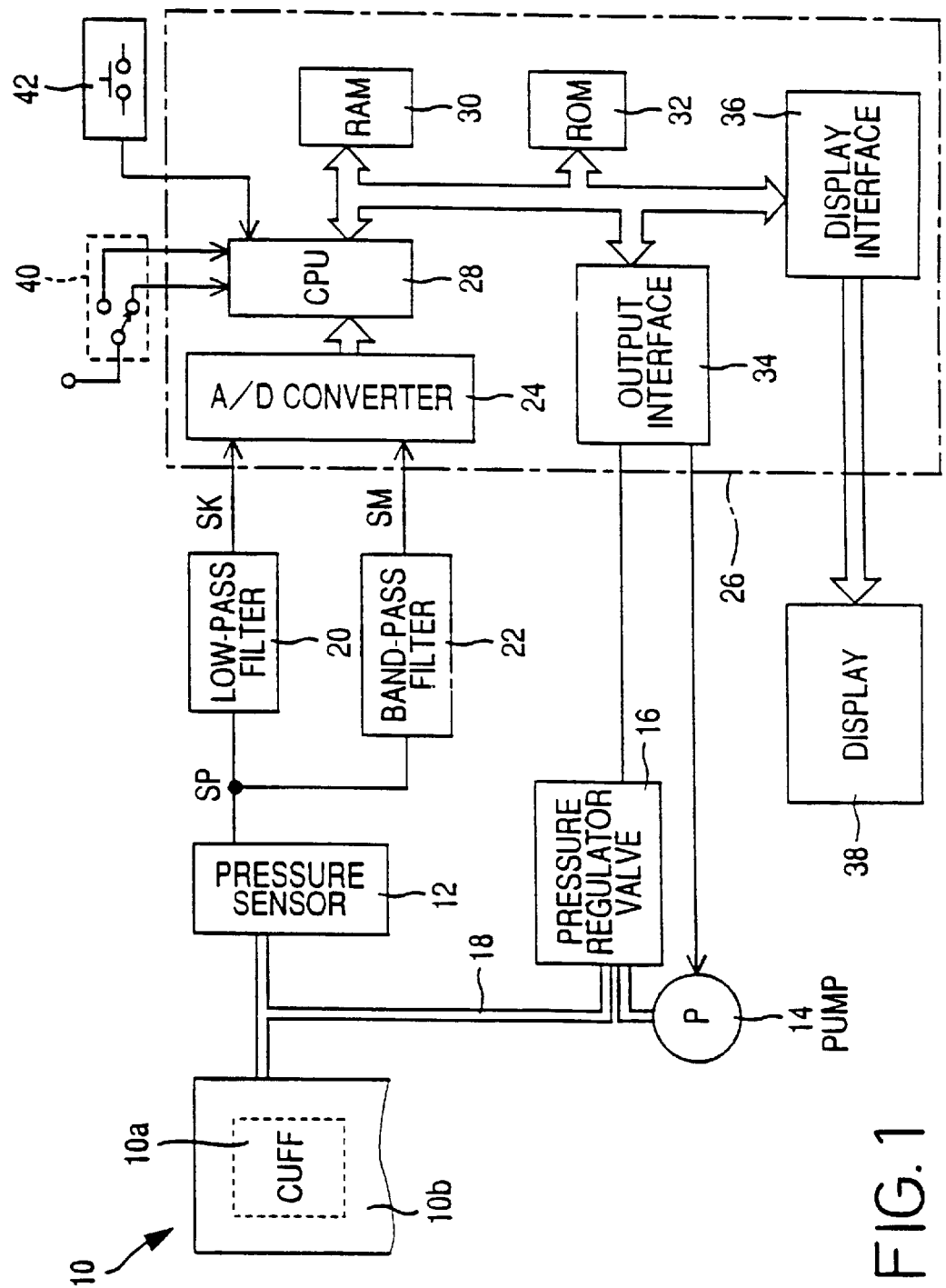
FIG. 1 is a diagrammatic view of a blood pressure (BP) monitor embodying the present invention.

In FIG. 1, reference numeral 10 designates an inflatable cuff which is adapted to be wound around an upper arm of a living subject, such as a patient. The cuff 10 is provided by an inflatable bag 10a formed of a resilient sheet such as a rubber sheet or a vinyl sheet, and a non-stretchable arm belt 10b in which the bag 10a is accommodated. The bag 10a is connected via air piping 18 to a pressure sensor 12, an air pump 14, and a pressure regulator valve 16.

The pressure sensor 12 includes a pressure-sensing semiconductor element which detects an air pressure in the cuff 10 (i.e., bag 10a), generates a pressure signal, SP, representing the detected cuff pressure, and supplies the pressure signal SP to each of a low-pass filter 20 and a band-pass filter 22. The low-pass filter 20 extracts, from the pressure signal SP, a direct-current (DC) component representing a static pressure, $P_c$, of the cuff 10, and supplies a cuff-pressure signal, SK, representing the static pressure $P_c$, to an analog-to-digital (A/D) converter 24. The band-pass filter 22 extracts, from the pressure signal SP, an alternate-current (AC) or frequency (e.g., 1 to 10 Hz) component representing pulses of a pulse wave which are produced in the cuff 10. The band-pass filter 22 supplies a pulse-wave signal, SM, representing the pulse wave, to the A/D converter 24. The pulse wave is a pressure oscillation which is transmitted from the arteries (e.g., brachial artery) of the living subject to the cuff 10 in synchronism with the heartbeat of the subject and is produced in the cuff 10.

The band-pass filter 22 functions as a pulse-wave sensor, and has a frequency characteristic that the band width thereof is sufficiently narrow to be able to extract, freely from noise such as motion artifact noise, the respective amplitudes of pulses of a pulse wave, i.e., pressure oscillation that is produced in the cuff 10 in synchronism with the heartbeat of the living subject, while the pressure of the cuff 10 is slowly decreased at the rate of 2 to 3 mmHg/sec. The A/D converter 24 includes a multiplexer which processes the two input signals SK, SM by time sharing, and has the function of concurrently converting the two analog signals into digital signals SK, SM, which are supplied to a central processing unit (CPU) 28 of a control device 26.

The control device 26 is provided by a microcomputer including the CPU 28, a random access memory (RAM) 30, a read only memory (ROM) 32, an output interface 34, and a display interface 36. The CPU 28 processes the input signals SK, SM supplied from the A/D converter 24, by utilizing a temporary-storage function of the RAM 30, according to control programs pre-stored in the ROM 32. The CPU 28 controls the air pump 14 and the pressure regulator valve 16 via the output interface 34, and controls a display 38 via the display interface 36. The display 38 includes an image display panel (not shown) which displays an image, such as BP values and waveforms, consisting of a number of picture elements, and a printer (not shown) which records, on a recording sheet of paper, using an ink, the image currently displayed on the image display panel. In the present embodiment, the air pump 14, the pressure regulator valve 16, and the control device 26 cooperate with one another to provide a cuff-pressure regulating device 52 (FIG. 2) which will be described later.

A mode switch 40 is manually operable by a user for selectively establishing a BP measure mode and a BP monitor mode. The mode switch 40 supplies a mode signal indicative of the selected mode, to the CPU 28. A Start/Stop switch 42 is manually operable by the user for inputting a start command or a stop command to start or stop an operation of the present BP monitor, and supplies a command signal indicative of the input command, to the CPU 28.

Figure 2:
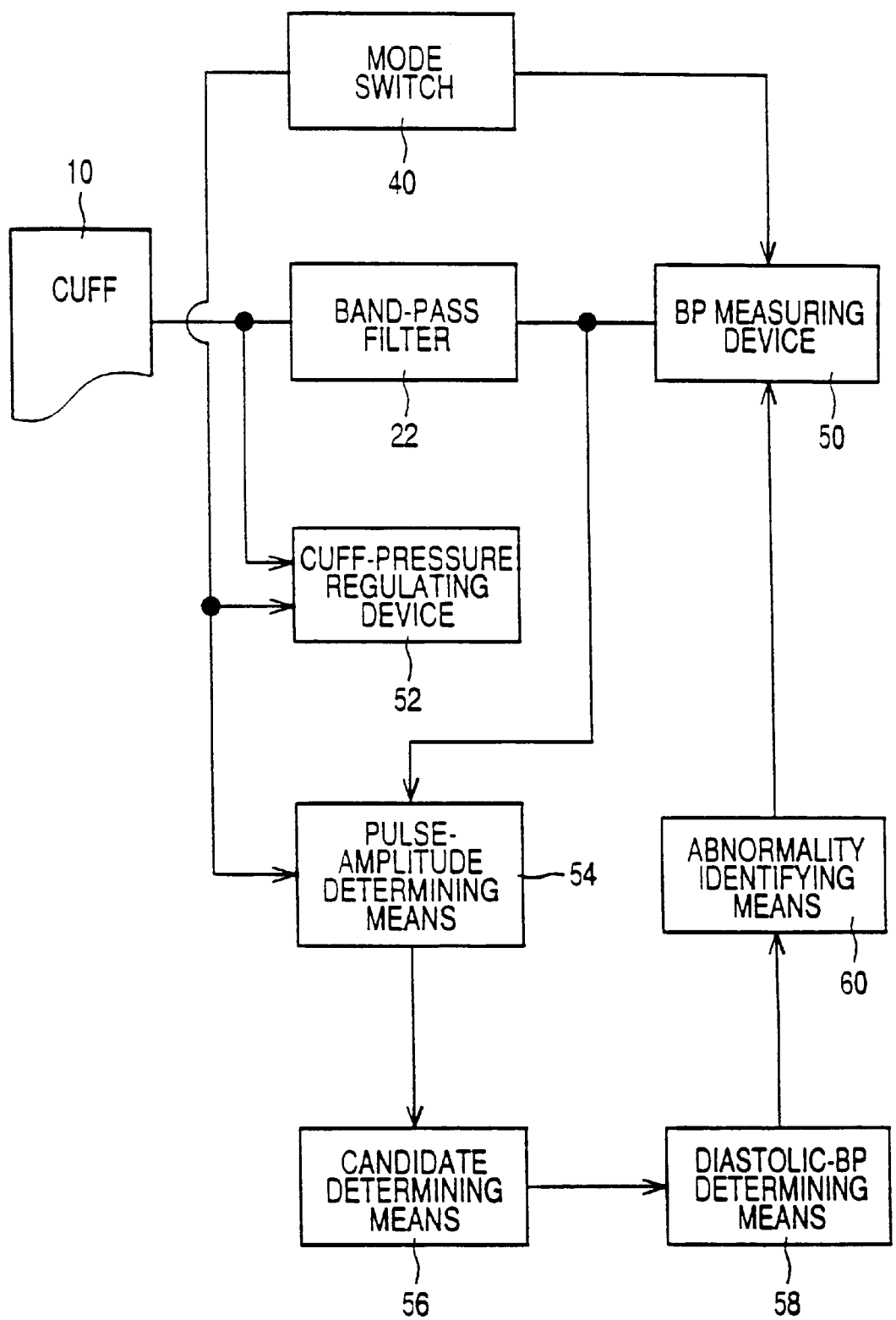
FIG. 2 is an illustrative view for explaining various functions of the BP monitor of FIG. 1.

FIG. 2 illustratively shows the various functions of the present BP monitor. When the mode switch 40 is operated to select the BP measure mode, the cuff-pressure regulating device 52 is operated to increase the pressure of the cuff 10 (hereinafter, referred to as the "cuff pressure $P_c$") up to a target pressure higher than a systolic BP value of the subject. While the cuff pressure is increased, or subsequently decreased from the target pressure at a low rate of 2 to 3 mmHg/sec, a BP measuring device 50 carries out an oscillometric BP measuring method in which a BP value of the subject is measured based on the variation of respective amplitudes, $A_n$ (n are natural numbers), of a series of pulses of a pulse wave which is detected from the cuff 10. The BP measuring device 50 is provided by the pressure sensor 12, the low-pass filter 20, and the control device 26. The BP measuring device 50 performs a BP measurement in the case where the operation of the BP monitor is started in the BP measure mode. The BP measuring device 50 also performs a BP measurement when abnormality identifying means 60 (described later) identifies an abnormal change of monitor diastolic BP values determined by diastolic-BP determining means 58 (described later). The control device 26 functions as both the diastolic-BP determining means 58 and the abnormality identifying means 60.

In the BP monitor mode, the cuff-pressure regulating device 52 operates, at a predetermined interval of time, for increasing the cuff pressure $P_c$ at a predetermined rate of change. Pulse-amplitude determining means 54 determines, by calculation, respective amplitudes, $A_m$ (m are natural numbers), of pulses of a pulse wave which is produced in the cuff 10 in synchronism with the heartbeat of the subject while the cuff pressure is increased by the cuff-pressure regulating device 52. Candidate determining means 56 judges whether an amplitude $A_m$ (m≦i−1) of each of prior pulses determined by the pulse-amplitude determining means 54 is not greater than a reference value, $A_a$ (=$A_m$×(1−R), where m=i and 0<R<1), which is smaller than an amplitude $A_m$ (m=i) of a subsequent pulse determined by the pulse-amplitude determining means 54, by a predetermined proportion, R, of the amplitude $A_m$ of the subsequent pulse. The amplitude of each of the prior pulses is determined before the amplitude of the subsequent pulse is determined. If a positive judgment is made, the candidate determining means 56 determines, as a diastolic BP candidate, $P_{ck}$, of the subject, a cuff pressure $P_c$ detected when each prior pulse is detected in the cuff 10. The control device 26 functions as both the pulse-amplitude determining means 54 and the candidate determining means 56. The diastolic-BP determining means 58 determines, as a monitor diastolic BP value, $MBP_{DIA}$, of the subject, the cuff pressure $P_c$ corresponding to the amplitude of a prior pulse, if the candidate determining means 56 determines, as a diastolic BP candidate, the cuff pressure $P_c$ corresponding to the amplitude of that prior pulse, with respect to each of a predetermined number, $N_0$, of the subsequent pulses.

The abnormality identifying means 60 identifies an abnormality of the monitor diastolic BP values $MBP_{DIA}$ determined by the diastolic-BP determining means 58, such as an abrupt decrease of the blood pressure of the subject. If the identifying means 60 identifies an abnormality, the BP measuring device 50 is immediately operated for carrying out an oscillometric BP measurement.

Next, there will be described the operation of the present BP monitor by reference to the flow charts of FIGS. 3 and 4.

First, at Step S1, the CPU 28 judges, based on the command signal supplied from the Start/Stop switch 42, whether the Start/Stop switch 43 has been operated to input a start command to start the operation of the BP monitor. If a negative judgment is made at Step S1, the control of the CPU 28 repeats Step S1 while waiting for a positive judgment to be made at Step S1. Meanwhile, if a positive judgment is made, the control of the CPU 28 proceeds with Step S2 to judge whether the mode switch 40 has been operated to select the BP monitor mode. In the case where the BP measure mode is in use, a negative judgment is made at Step S2, so that the control of the CPU 28 goes to Step S3, i.e., BP measure routine according to which a known oscillometric BP measurement is carried out to measure a systolic, a diastolic, and a mean BP value, $BP_{SYS}$, $BP_{DIA}$, $BP_{MEAN}$, of the subject. When the BP measurement is finished, the pressure regulator valve 16 is opened to quickly deflate the cuff 10, thereby releasing the upper arm of the subject from the cuff pressure $P_c$, i.e., pressing force of the cuff 10. Step S3 is followed by Step S4 to store the measured BP values in the RAM 30 and operate the display 38 to indicate numerals representing the measured BP values.

More specifically described, in the oscillometric BP measurement effected at Step S3, the air pump 14 and the pressure regulator valve 16 are operated to quickly increase the cuff pressure $P_c$ up to a predetermined target pressure, $P_{cm}$, e.g., 180 mmHg. Subsequently, the air pump 14 is stopped and the degree of opening of the regulator valve 16 is regulated, so that a slow deflation of the cuff 10 is started. That is, the cuff pressure $P_c$ is decreased at a low rate of 2 to 3 mmHg/sec which is suitable for BP measurements. During this slow cuff-pressure decrease, the control device 26 determines BP values according to a well known oscillometric BP determining algorithm. That is, the CPU 28 determines, as a systolic BP value $BP_{SYS}$, a cuff pressure at the time when the pulse amplitudes $A_n$ significantly change in a phase in which the amplitudes $A_n$ increase; determines, as a mean BP value $BP_{MEAN}$, a cuff pressure at the time when the amplitudes $A_n$ take a maximum value, i.e., when a pulse having a maximum amplitude is produced; and determines, as a diastolic BP value $BP_{DIA}$, a cuff pressure at the time when the pulse amplitudes $A_n$ significantly change in a phase in which the amplitudes $A_n$ decrease.

In the case where the mode switch 40 has been operated to select the BP monitor mode, a positive judgment is made at Step S2 and accordingly the control of the CPU 28 goes to Step S5 to judge whether a timer has counted up a predetermined monitor cycle time from the time when a monitor diastolic BP value $MBP_{DIA}$ had been determined at Step S6 in the preceding control cycle in accordance with the main routine of FIG. 3. The monitor cycle time may fall in the range of from several minutes to ten and several minutes. If a negative judgment is made at Step S5, the CPU 28 repeats Step S5 until a positive judgment is made. Meanwhile, if a positive judgment is made at Step S5, the control of the CPU 28 goes to Step S6, i.e., BP monitor routine of FIG. 4.

At Step S6-1 of FIG. 4, the CPU 28 judges whether the CPU 28 has received, from the band-pass filter 22, a pulse-wave signal SM representing one pulse of a pulse wave. If a negative judgment is made at Step S6-1, the current control cycle in accordance with the routine of FIG. 4 is ended. On the other hand, if a positive judgment is made at Step S6-1, the control of the CPU 28 goes to Step S6-2 to increase the cuff pressure $P_c$ by a predetermined pressure increase amount, $\Delta P_c$, and subsequently to Step S6-3 to determine, by calculation, an amplitude $A_m$ of the pulse received at Step S6-1 and store, in an appropriate area of the RAM 30, the determined amplitude $A_m$ together with the cuff pressure $P_c$ at the time when the pulse is detected through the band-pass filter 22. The cuff pressure $P_c$ is read from the cuff-pressure signal SK supplied from the low-pass filter 20. While Steps S6-2 and S6-3 are repeated, the cuff pressure $P_c$ is increased at a predetermined rate of change, more specifically, stepwise by the respective pressure amounts $\Delta P_c$, as shown in FIG. 5. While the cuff pressure $P_c$ is held for a short duration at each of the pressure steps, the CPU 28 reads in one pulse, determines the amplitude $A_m$ of the pulse, and stores the pulse amplitude $A_m$ in the RAM 30. Step S6-3 corresponds to the pulse-amplitude determining means 54.

At Step S6-4, the CPU 28 judges whether the amplitude $A_m$ (m≦i−1) of each of the prior pulses determined at Step S6-3 in the prior control cycles before the current control cycle is not greater than a reference value $A_a$ (e.g., 0.7×$A_m$) which is smaller than the amplitude $A_m$ (m=i) of the current pulse determined at Step S6-3 in the current control cycle, by a predetermined proportion R (e.g., 30% (R=0.3)) of the amplitude $A_m$ of the current pulse. If a positive judgment is made, the CPU 28 determines, as a diastolic BP candidate $P_{ck}$ of the subject, the cuff pressure $P_c$ corresponding to the pulse amplitude $A_m$ of each prior pulse. While the cuff pressure $P_c$ is increased up to a mean BP value $BP_{MEAN}$ of the subject, the pulse amplitudes $A_m$ continue to increase as indicated at broken line in FIG. 5A. For example, in the case where the pulse amplitude $A_2$ is determined at Step S6-3, the only prior amplitude $A_1$ is compared with 0.7×(the amplitude $A_2$). If the amplitude $A_1$ is greater than 0.7×(the amplitude $A_2$), the cuff pressure $P_{c1}$ corresponding to the amplitude $A_1$ is not determined as a diastolic BP candidate $P_{ck}$. In the example shown in FIG. 5B, a negative judgment is made at Step S6-4 for each of the amplitudes $A_1$ to $A_4$. Once a negative judgment is made for a pulse amplitude $A_m$ at Step S6-4, the CPU 28 never makes a judgment for that amplitude at Step S6-4 in the following control cycles.

On the other hand, if the CPU 28 makes a positive judgment at Step S6-4, the control of the CPU 28 goes to Step S6-5 to determine the cuff pressure $P_c$ corresponding to the pulse amplitude $A_m$, as a diastolic BP candidate $P_{ck}$, and store the pressure $P_c$ in an appropriate area of the RAM 30. For example, in the case where the pulse amplitude $A_6$ is determined at Step S6-3, the prior amplitude $A_5$ is compared with 0.7×(the amplitude $A_6$) and, if the amplitude $A_5$ is not greater than 0.7×(the amplitude $A_6$), the cuff pressure $P_{c5}$ corresponding to the amplitude $A_5$ is determined as a diastolic BP candidate $P_{ck}$. Thus, a positive judgment is made at Step S6-4 for the amplitude $A_5$. Regarding the example shown in FIG. 5B, a positive judgment is made for the amplitude $A_5$, when the amplitude $A_5$ is compared with the amplitude $A_7$ in the next cycle, and with the amplitude $A_8$ in the cycle after that next cycle. Steps S6-4 and S6-5 correspond to the candidate determining means 56.

Step S6-5 is followed by Step S6-6 to judge, regarding each of the prior amplitudes $A_m$, whether a number, N, of the positive judgments made for each prior amplitude $A_m$ at Step S6-4 becomes not smaller than a reference number, $N_0$, e.g., 3. If a positive judgment is made for any of the prior amplitudes $A_m$, a positive judgment is finally made at Step S6-5. For example, in the example shown in FIG. 5B, when the amplitude $A_8$ is determined at Step S6-3, a positive judgment is made for the amplitude $A_5$ and a negative judgment is made for each of the amplitudes $A_6$ and $A_7$. Accordingly, a positive judgment is finally made at Step S6-6. The reference number $N_0$ is empirically determined as being suitable for obtaining a diastolic BP value. In the case where the above-indicated pressure increase amount $\Delta P_c$ is about 5 mmHg, the reference number $N_0$ is determined at 3.

If a negative judgment is finally made at Step S6-6, i.e., if a negative judgment is made for all the prior amplitudes $A_m$, the control of the CPU 28 goes back to Step S6-1. On the other hand, if a positive judgment is finally made at Step S6-6, the control goes to Step S6-7 to determine, as a monitor diastolic BP value $MBP_{DIA}$, the cuff pressure $P_c$ corresponding to the pulse amplitude $A_m$ for which three positive judgments are made at Step S6-4. The thus determined cuff pressure $P_c$ is stored in the RAM 30. Regarding the example shown in FIG. 5B, the cuff pressure $P_{c5}$ is determined as a monitor diastolic BP value $MBP_{DIA}$. In the present embodiment, Steps S6-6 and S6-7 correspond to the diastolic-BP determining means 58. Step S6-7 is followed by Step S6-8 to display the newly determined monitor diastolic BP value $MBP_{DIA}$ in place of the old value $MBP_{DIA}$ determined in Step S6 in the preceding control cycle in accordance with the main routine of FIG. 3.

After the monitor diastolic BP value $MBP_{DIA}$ is determined at Step S6, the control of the CPU 28 goes to Step S7 to judge whether the Start/Stop switch 42 is operated to stop the BP monitoring operation. If a positive judgment is made at Step S7, the control goes back to Step S1. On the other hand, if a negative judgment is made at Step S8, the control goes to Step S8 to judge whether an abnormality has occurred to the monitor diastolic BP values $MEP_{DIA}$. For example, the CPU 28 identifies an abnormality of the diastolic BP values $MBP_{DIA}$, if an amount, or a rate, of change of the current value $MBP_{DIA}$ from a moving average of prior values $MBP_{DIA}$ exceeds a reference value, which indicates that the blood pressure of a living subject has abruptly decreased. Step S8 corresponds to the abnormality identifying means 60.

If a negative judgment is made at Step S8, the control goes back to Step S5 and repeats Steps S5 to S8. Meanwhile, if a positive judgment is made at Step S8, the control of the CPU 28 goes to Step S9 to carry out an oscillometric BP measurement using the cuff 10 like at Step S3. Step S9 is followed by Step S10 to operate the display 38 to display the measured BP values $BP_{SYS}$, $BP_{MEAN}$, $BP_{DIA}$.

Figure 5A:
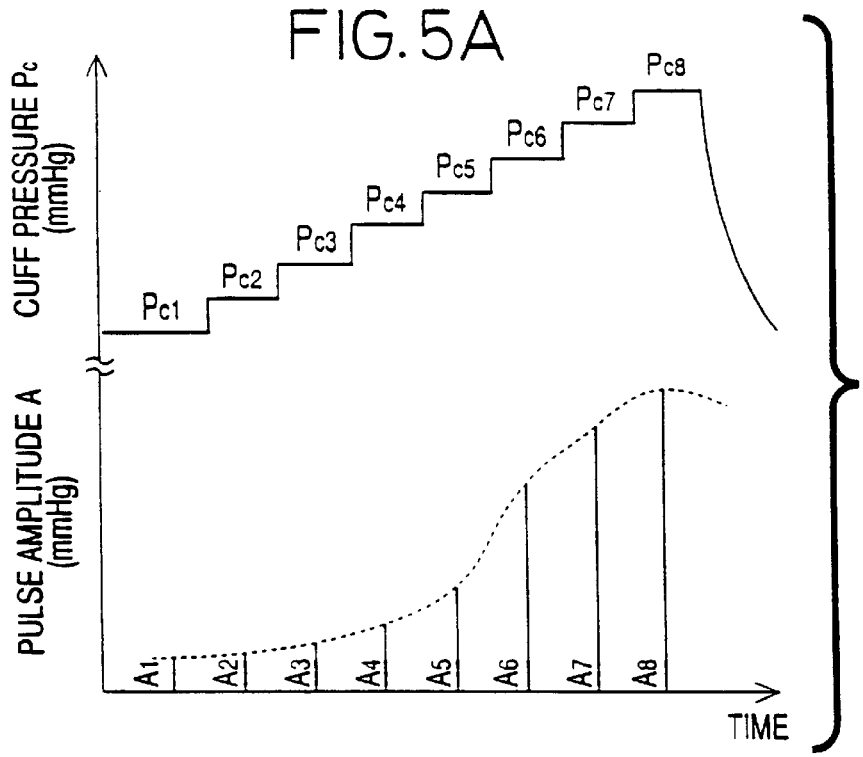
FIG. 5A is a time chart showing a relationship between time and cuff pressure, $P_c$, or pulse amplitude, $A_m$.
Figure 5B:
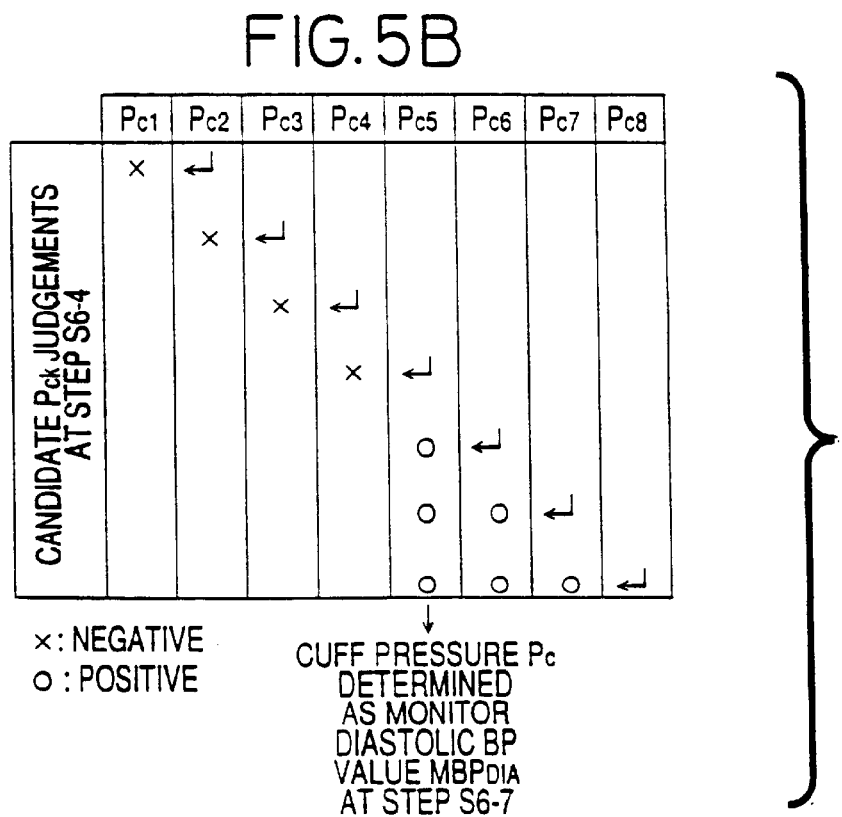
FIG. 5B is a table showing a manner in which a cuff pressure, $P_c$, is determined as a monitor diastolic blood pressure, $MBP_{DIA}$.

As is apparent from the foregoing description, the present BP monitor operates such that in the BP monitor mode the amplitudes $A_m$ of pulses of a pulse wave which are produced in the cuff 10 while the cuff pressure $P_c$ is increased by the cuff-pressure regulating device 52, are determined by the pulse-amplitude determining means 54. In addition, the candidate determining means 56 judges whether the amplitude $A_m$ (m≦i−1) of each of the prior pulses determined in the prior control cycles before the current control cycle is not greater than the reference value $A_a$ which is smaller than the amplitude $A_m$ (m=i) of the current pulse determined in the current control cycle, by the predetermined proportion R of the amplitude $A_m$ of the current pulse and, if a positive judgment is made, determines, as a diastolic BP candidate $P_{ck}$ of the subject, the cuff pressure $P_c$ corresponding to the amplitude $A_m$ of each prior pulse. The diastolic-BP determining means 58 judges, regarding each of the prior amplitudes $A_m$, whether the number N of the positive judgments made for each prior amplitude $A_m$ becomes not smaller than the reference number $N_0$ and, if a positive judgment is made for any of the prior amplitudes $A_m$, determines, as a monitor diastolic BP value $MBP_{DIA}$, the cuff pressure $P_c$ corresponding to the prior amplitude $A_m$ for which the predetermined number $N_0$ of positive judgments are made. The present BP monitor has been developed based on the fact that a diastolic BP value $BP_{DIA}$ does not correspond to a pulse having an amplitude not smaller than an amplitude, $A_{max} \times (1-R)$, smaller than a maximum amplitude, $A_{max}$, of the last pulse that is detected in the current control cycle, by the predetermined proportion R of the amplitude $A_{max}$ of the last pulse. The last or current pulse has a maximum amplitude $A_{max}$ of all the amplitudes $A_m$ of the prior pulses which have been detected prior to the last or current pulse while the cuff pressure $P_c$ is increased, as indicated in FIG. 5A. In addition, the present BP monitor has been developed based on the fact that an amplitude of a pulse correctly corresponding to a diastolic BP value $BP_{DIA}$ does not change even if the cuff pressure $P_c$ is increased.

Therefore, the present BP monitor can determine a monitor diastolic BP value at a pressure level higher than the diastolic BP value by only the product of the pressure increase amount $\Delta P_c$ and the reference number $N_0$. This monitor diastolic BP value enjoys high accuracy. In addition, since the pressure level where the BP value is determined is considerably low, the living subject does not feel discomfort.

In the present embodiment, the cuff-pressure regulating device 52 stepwise increases the cuff pressure $P_c$, by alternately increasing it by the increment amount $\Delta P_c$ and holding it at each increased level. The pulse-amplitude determining means 54 determines, by calculation, the amplitude $A_m$ of the pulse which is produced when the cuff pressure $P_c$ is held at each increased level. The thus determined pulse amplitude $A_m$ enjoys high accuracy because it is free from the adverse influence resulting from the increasing of the cuff pressure $P_c$. Therefore, the monitor BP values are determined with accuracy based on the pulse amplitudes $A_m$.

In addition, in the present embodiment, when the abnormality identifying means 60 identifies an abnormality of the monitor diastolic BP values $MBP_{DIA}$, the BP monitor automatically carries out an oscillometric BP measurement by increasing the cuff pressure $P_c$ up to a high level which is estimated to be higher than a systolic BP value of a living subject. Thus, the BP monitor provides accurate BP values upon identification of an abnormality of the subject. Therefore, a doctor or a nurse can take an appropriate medical treatment on the subject.

Although in the illustrated embodiment the pressure $P_c$ of the cuff 10 is stepwise increased at a predetermined rate in the BP monitor mode, it is possible that the cuff pressure $P_c$ be continuously increased at a predetermined rate.

While in the illustrated embodiment the pressure increase amount $\Delta P_c$ is a constant value, it is possible that the pressure increase amount $\Delta P_c$ be variable depending upon the current cuff pressure $P_c$.

Although in the illustrated embodiment the predetermined proportion R used at Step S6-4 is a constant value, it is possible that the CPU 28 determine a value R based on the variation of the amplitudes of pulses of a pulse wave obtained in the oscillometric BP measurement effected at Step S3. In the latter case, the BP monitor can determine a value R suitable for each individual subject.

While in the illustrated embodiment the reference number $N_0$ used at Step S6-6 is a constant value, it is possible that the CPU 28 determine a number $N_0$ based on the variation of the amplitudes of pulses of a pulse wave obtained in the oscillometric BP measurement effected at Step S3. In the latter case, the BP monitor can determine a number $N_0$ suitable for each individual subject.

In the illustrated embodiment, the BP measuring device 50 performs an oscillometric BP measurement at Step S3 when the operation of the BP monitor is started in a state in which the BP measure mode has been selected, or the abnormality identifying means 60 identifies an abnormality of the monitor diastolic BP values determined by the diastolic-BP determining means 58. However, it is possible to adapt the BP measuring device 50 to periodically perform an oscillometric BP measurement at a predetermined cycle time, i.e., at a predetermined interval of time.

Referring next to FIGS. 7 to 12, there will be described a continuous blood pressure (BP) monitor 100 as a second embodiment of the present invention. The BP monitor 100 may be used to monitor BP values of a patient who is undergoing, or has undergone, a surgical operation.

Figure 7:
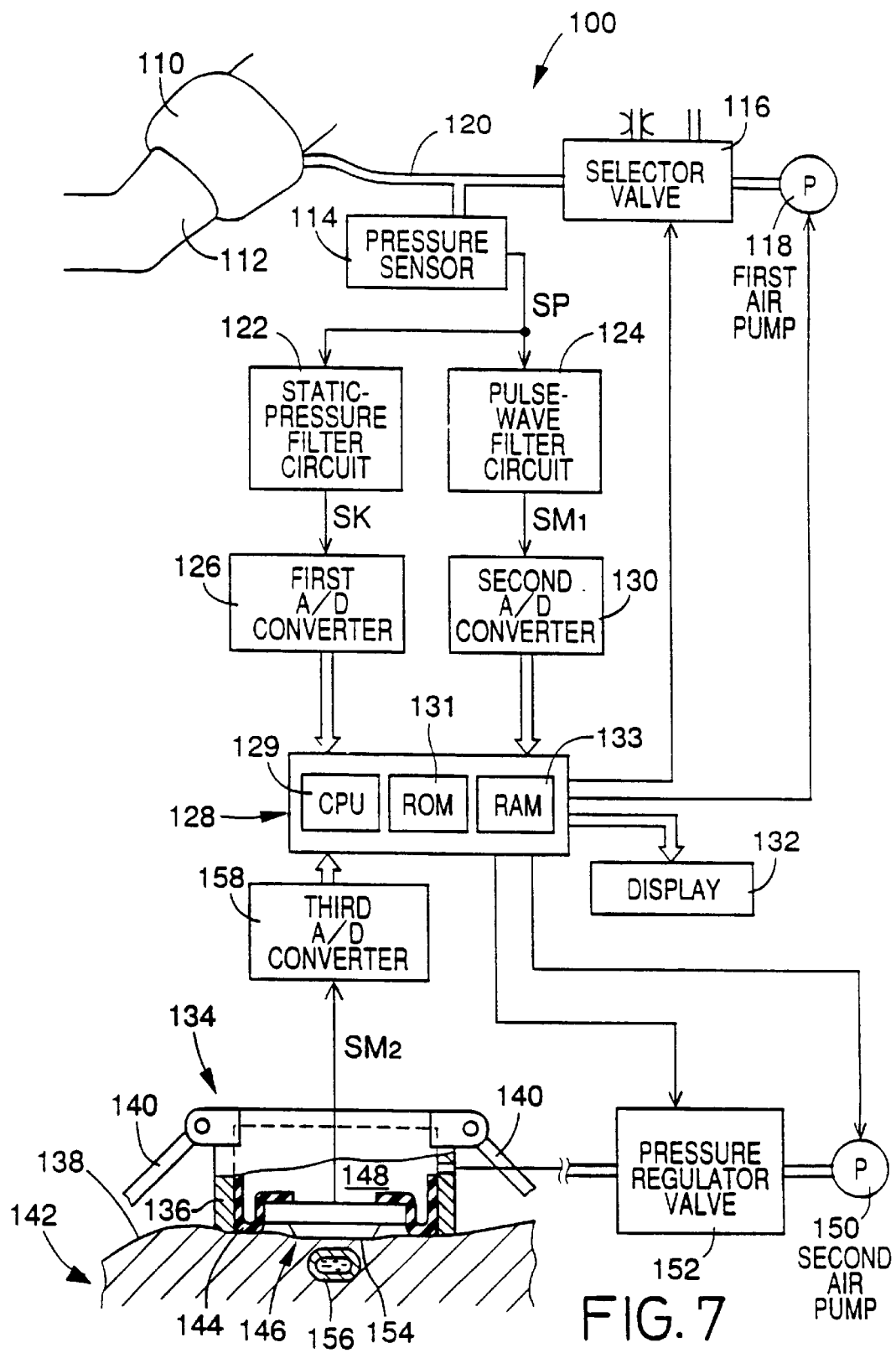
FIG. 7 is a diagrammatic view of a continuous BP monitor as a second embodiment of the present invention.

In FIG. 7, the BP monitor 100 includes an inflatable cuff 110 including a rubber bag and a band-like cloth bag in which the rubber bag is accommodated. The cuff 110 is wound around, e.g., an upper arm 112 of a patient. The cuff 110 is connected via piping 120 to a pressure sensor 114, a selector valve 116, and a first air pump 118. The selector valve 116 is selectively placed, under control of an electronic control device 128, in a first state in which the valve 116 permits pressurized air to be supplied from the air pump 118 to the cuff 110 to increase quickly the air pressure of the cuff 110 (hereinafter, referred to as the "cuff pressure"), a second state in which the valve 116 causes the cuff 110 to be deflated slowly, and a third state in which the valve 116 causes the cuff 110 to be deflated quickly.

The pressure sensor 114 detects the cuff pressure (i.e., air pressure in the cuff 110), and generates a pressure signal, SP, representing the detected cuff pressure. The pressure signal SP is supplied to each of a static-pressure filter circuit 122 and a pulse-wave filter circuit 124. The static-pressure filter circuit 122 includes a low-pass filter which extracts, from the pressure signal SP, a cuff-pressure signal, SK, representative of a static or direct-current component of the pressure signal SP. The cuff-pressure signal SK is supplied via a first analog-to-digital (A/D) converter 126 to the control device 128.

The pulse-wave filter circuit 124 includes a band-pass filter which extracts, from the pressure signal SP, a pulse-wave signal, $SM_1$, representative of an oscillating or alternating-current component of the pressure signal SP. The pulse-wave signal $SM_1$ is supplied via a second A/D converter 130 to the control device 128. The alternating-current component represented by the pulse-wave signal $SM_1$ corresponds to an oscillatory pressure wave, i.e., pulse wave which is produced from a brachial artery (not shown) of the patient in synchronism with the heartbeat of the patient and is propagated via skin tissue to the cuff 110. This pulse wave is referred to as the "cuff pulse wave (CPW)" to be distinguished from a "pressure pulse wave (PPW)" which will be described later. In the present embodiment, the cuff 110, the pressure sensor 114, and the pulse-wave filter circuit 124 cooperate with one another to provide a cuff pulse wave sensor.

The control device 128 is provided by a microcomputer including a central processing unit (CPU) 129, a read only memory (ROM) 131, a random access memory (RAM) 133, and an input and output (I/O) port (not shown). The CPU 129 processes input signals, including the signals SK, $SM_1$, by utilizing a temporary-storage function of the RAM 133, according to control programs pre-stored in the ROM 131. In addition, the CPU 129 supplies drive signals via the I/O port to drive circuits (not shown) associated with the selector valve 116 and the air pump 118, respectively. Thus, the CPU 129 controls respective operations of the valve 116 and the pump 118. For example, when an oscillometric BP measurement using the cuff 110 is carried out to calibrate the present BP monitor 100, the CPU 129 controls the valve 116 and the pump 118 to increase quickly the cuff pressure up to a predetermined target value and subsequently decrease the cuff pressure at a low rate of 2 to 3 mmHg/sec. Based on the variation of the cuff pulse wave represented by the pulse-wave signal $SM_1$ provided by the pulse-wave filter circuit 124 during the low-rate decreasing of the cuff pressure, the CPU 129 determines a systolic, a mean, and a diastolic BP value of the patient, according to a known oscillometric BP measuring method. In addition, the CPU 129 controls a display 132 to display the thus determined BP values.

A pressure-pulse-wave (PPW) detecting probe 134 includes a container-like sensor housing 136, and a fastening band 140 connected to the sensor housing 136. With the help of the fastening band 140, the PPW detecting probe 134 is detachably attached to a wrist 142 of the same arm 112 of the patient on which the cuff 110 is worn, such that an opening of the sensor housing 136 is opposed to a body surface 138 of the patient. A PPW sensor 146 is secured via an elastic diaphragm 144 to inner surfaces of the sensor housing 136 such that the PPW sensor 146 is movable relative to the housing 136 and is advanceable through the opening of the housing 136 toward the body surface 138 of the patient. The sensor housing 136 and the diaphragm 144 cooperate with each other to define a pressure chamber 148, which is supplied with pressurized air from a second air pump 150 via a pressure regulator valve 152. Thus, the PPW sensor 146 is pressed on the body surface 138 with a pressing force, $P_{HD}$, corresponding to an air pressure in the chamber 148. In the present embodiment, the pressing forces of the PPW sensor 146 applied to the body surface 138 or a radial artery 156 are indicated in terms of pressure values (mmHg) in the chamber 148. The sensor housing 136, the diaphragm 144, the pressure chamber 148, the second air pump 150, the pressure regulator valve 152, etc. cooperate with one another to provide a pressing device which presses the PPW sensor 146 against the radial artery 156 via the body surface or skin tissue 138.

Figure 8:
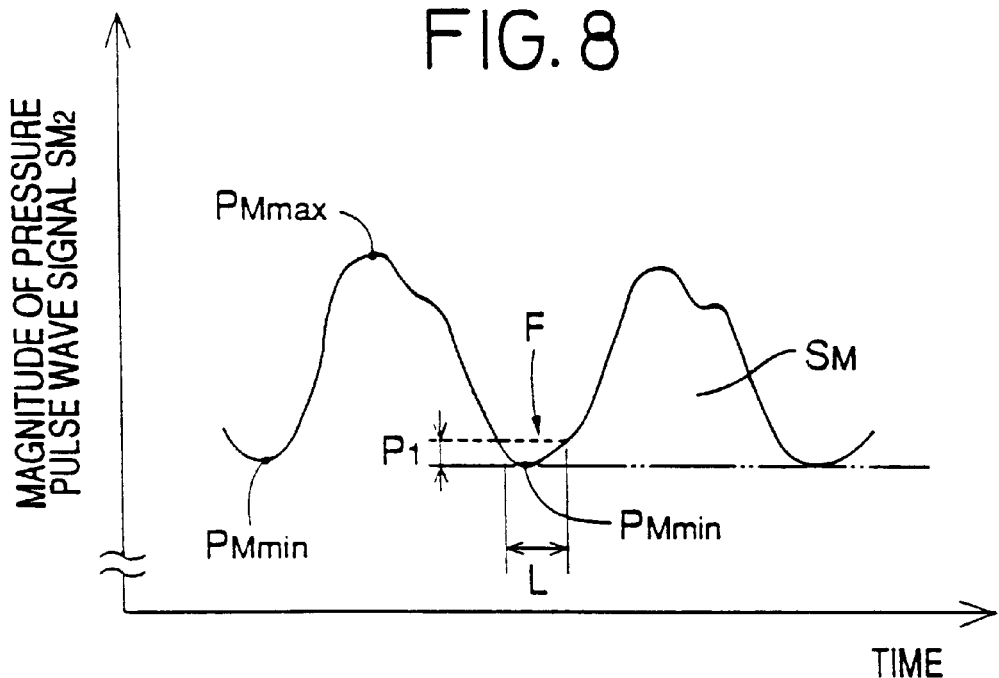
FIG. 8 is a graph showing an example of a pressure pulse wave (PPW) detected by a PPW sensor of the BP monitor of FIG. 7.

The PPW sensor 146 includes a semiconductor chip formed of a monocrystalline silicon which has a press surface 154, and a number of pressure-sensing semiconductor elements (not shown) which are arranged, in the press surface 154, in an array at a regular interval of distance (about 0.2 mm), such that the array of pressure-sensing elements extends in the direction of width of the radial artery 156. When the PPW sensor 146 is pressed against the radial artery 156 via the body surface 138 of the wrist 142, the PPW sensor 146 detects an oscillatory pressure wave, i.e., pressure pulse wave (PPW) which is produced from the radial artery 156 in synchronism with the heartbeat of the patient and is propagated via the body surface 138 to the PPW sensor 146. The PPW sensor 146 generates a PPW signal, $SM_2$, representing the detected PPW, and supplies the PPW signal $SM_2$ to the control device 128 via a third A/D converter 158. An example of the PPW (i.e., PPW signal $SM_2$) detected by the PPW sensor 146 is illustrated in the graph of FIG. 8.

The CPU 129 of the control device 128 processes the input signals, including the PPW signal $SM_2$, by utilizing the temporary-storage function of the RAM 133, according to the control programs pre-stored in the ROM 131, and supplies drive signals to drive circuits (not shown) associated with the second air pump 150 and the pressure regulator valve 152, respectively. Thus, the CPU 129 controls respective operations of the pump 150 and the valve 152 to regulate the air pressure of the pressure chamber 148 applied to the PPW sensor 146, i.e., the pressing force $P_{HD}$ of the PPW sensor 146 applied to the radial artery 156 via the body surface or skin tissue 138.

When a continuous BP monitoring operation is carried out, the CPU 129 determines an optimum pressing force, $P_{HDO}$, of the PPW sensor 146 applied to the radial artery 156, based on the PPW (signal $SM_2$) detected by the PPW sensor 146 while the pressure of the pressure chamber 148 is slowly changed, and controls the pressure regulator valve 152 to maintain the pressure of the chamber 148 at the determined optimum pressing force $P_{HDO}$. In addition, the CPU 129 determines a relationship between BP values and PPW magnitudes $P_M$ (i.e., voltage values of the signal $SM_2$), based on a systolic and a diastolic BP value, $BP_{SYS}$, $BP_{DIA}$, measured using the cuff 110 according the oscillometric BP measuring method, and a maximum and a minimum magnitude, $P_{Mmax}$, $P_{Mmin}$, of one heartbeat-synchronous pulse of the PPW detected by the PPW sensor 146 being pressed on the body surface 138 with the optimum pressing force $P_{HDO}$. According to the thus determined relationship, the CPU 129 determines a systolic and a diastolic BP value (i.e., monitor BP values), $MBP_{SYS}$, $MBP_{MEAN}$, $MBP_{DIA}$, of the patient, based on a maximum magnitude (i.e., upper-peak magnitude) $P_{Mmax}$, a mean magnitude (described later), $P_{Mmean}$, and a minimum magnitude (i.e., lower-peak magnitude), $P_{Mmin}$, of each of successive heartbeat-synchronous pulses of the PPW detected by the PPW sensor 146 being pressed with the optimum pressing force $P_{HDO}$. Subsequently, the CPU 129 controls the display 132 to successively display, for each heartbeat-synchronous pulse, the thus determined monitor BP values $MBP_{SYS}$, $MBP_{MEAN}$, $MBP_{DIA}$, in digits, and continuously display the waveform of the PPW detected by the PPW sensor 146. This waveform represents the instantaneous monitor BP values MBP of the patient.

Figure 9:
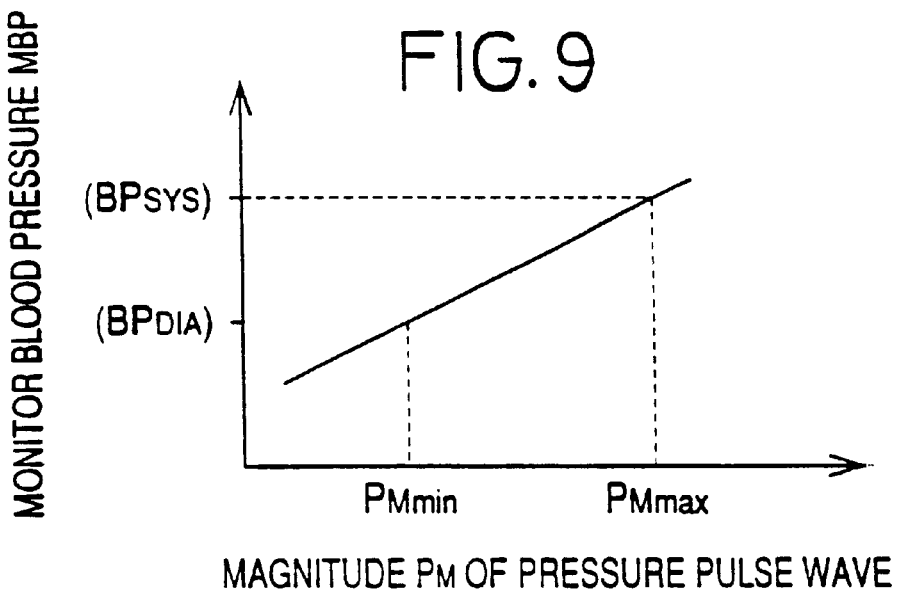
FIG. 9 is a graph showing a relationship determined by a control device of the BP monitor of FIG. 7.

FIG. 9 shows an example of a relationship between BP values MBP (monitor BP values) and PPW magnitudes $P_M$ that is determined by the control device 128 or the CPU 129. This relationship is expressed by the following linear function:

$$MBP = A \cdot P_M + B$$

where A is a constant corresponding to the slope of the linear function and B is a constant corresponding to the intercept of the axis of ordinate indicative of the monitor BP values MBP.

Figure 10:
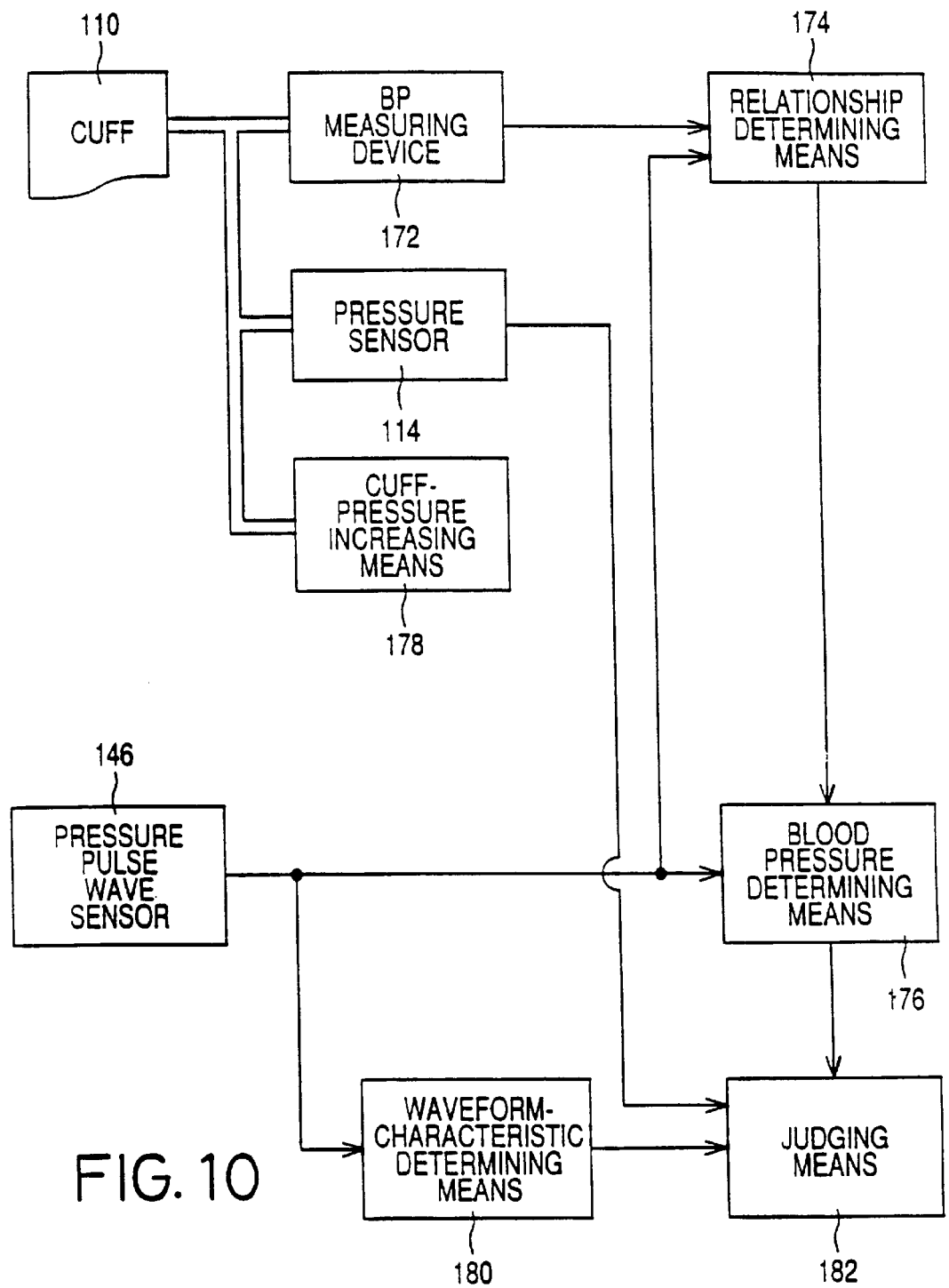
FIG. 10 is an illustrative view for explaining various functions of the control device of the BP monitor of FIG. 7.

FIG. 10 illustrates various functions of the electronic control device 128 of the continuous BP monitor 100. The pressing pressure of the cuff 110 is detected by the pressure sensor 114. The static-pressure filter circuit 122 cooperates with the control device 128 to provide a BP measuring device 172 which measures, according to an oscillometric BP measuring method (JIS T 1115; JIS is Japanese Industrial Standard), a systolic BP value $BP_{SYS}$, a mean BP value $BP_{MEAN}$, and a diastolic BP value $BP_{DIA}$ of a living subject based on the variation of respective amplitudes of heartbeat-synchronous pulses of the cuff pulse wave (CPW) detected by the CPW sensor 114, 124, 130 while the pressure of the cuff 110 is slowly increased or decreased at the rate of 2 to 3 mmHg/sec. The cuff pulse wave is represented by the pulse-wave signal $SM_1$ obtained through the pulse-wave filter circuit 124. The PPW sensor 146 is worn on the wrist 142 of the same arm 112 of the patient on which the cuff 110 is worn, and detects the PPW produced from the radial artery 156 downstream of the brachial artery being pressed by the cuff 110. The control device 128 functions as a relationship determining means 174 which determines a $MBP$-$P_M$ relationship between monitor BP values MBP and PPW magnitudes $P_M$ that is expressed by the linear function shown in FIG. 9, based on the PPW detected by the PPW sensor 146 and the BP values measured by the BP measuring device 172. The control device 128 also functions as a monitor-BP (MBP) determining means 176 which successively determines, according to the $MBP$-$P_M$ relationship, a monitor BP value MBP of the subject based on a magnitude of each of heartbeat-synchronous pulses of the PPW detected by the PPW sensor 146. The selector valve 116 and the first air pump 118 cooperate with the control device 128 to provide a cuff-pressure regulating device 178 which regulates the air pressure of the cuff 110 (i.e., cuff pressure) that is detected by the pressure sensor 114. The cuff-pressure regulating device 178 changes the cuff pressure according to a well-known procedure, so that the BP measuring device 172 can measure BP values of the patient using the cuff 10 and the relationship determining means 174 calibrates the $MBP$-$P_M$ relationship based on the BP values measured using the cuff 110. For example, the regulating device 178 increases the cuff pressure up to a target value, e.g., 180 mmHg, which is higher than an estimated systolic BP value of the patient and subsequently decreases the cuff pressure slowly at the rate of 2 to 3 mmHg/sec, during a measurement period in which BP values of the patient are determined by the BP measuring device 172 according to a well-known oscillometric BP determining algorithm. After the BP measuring operation, the regulating device 178 quickly deflates the cuff 110. In addition, the cuff-pressure regulating device 178 provides a cuff-pressure increasing means 178 which continuously or stepwise increases the cuff pressure at a predetermined rate.

Moreover, the control device 128 functions as a waveform-characteristic determining means 180 which determines a characteristic of a lower-peak portion of a waveform of each of successive heartbeat-synchronous pulses of the pressure pulse wave (PPW) which are detected by the PPW sensor 146 when the cuff pressure is increased at the predetermined rate by the cuff-pressure increasing means 178. The lower-peak portion of the waveform of each pulse includes a lower-peak point of each pulse. In addition, the control device 128 functions as a judging means 182 which judges whether the relationship determined by the relationship determining means 174 is accurate, based on at least one diastolic BP value $BP_{DIA}$ determined by the blood pressure determining means 176 and a cuff pressure corresponding to a time when the waveform characteristics detected by the waveform-characteristic determining means 180 significantly largely change.

Next, there will be described the operation of the BP monitor 100 constructed as described above, by reference to the flow chart of FIG. 11 representing a control program pre-stored in the ROM 131.

First, at Step S101, the CPU 129 of the control device 128 controls the second air pump 150 and the pressure regulator valve 152 to increase slowly the pressure of the pressure chamber 148, and determines, as an optimum pressing force $P_{HDO}$, a pressure $P_{HD}$ of the chamber 148 when the PPW sensor 146 detects a maximum pulse having the greatest amplitude of respective amplitudes of all the pulses detected thereby during the slow increasing of the pressure of the chamber 148. Subsequently, the CPU 129 maintains or holds the pressure of the chamber 148 at the thus determined optimum pressing force $P_{HDO}$. Thus, the optimum pressing force $P_{HDO}$ is applied to the PPW sensor 146 to press the radial artery 156 via the body surface 138.

Next, the control of the CPU 129 proceeds with Step S102 to judge whether a relationship as shown in FIG. 9 has been determined for a particular patient on which the cuff 110 is worn. If a positive judgment is made at Step S102, the control of the CPU 129 goes to Step S103. Since, however, initially a negative judgment is made at Step S102, the control goes to Step S107 corresponding to the BP measuring device 172. Specifically described, the selector valve 116 is switched to the first state and the first air pump 118 is operated, so that the cuff pressure is increased up to a target pressure (e.g., 180 mmHg) higher than an estimated systolic BP value of the patient. Subsequently, the air pump 118 is stopped and the selector valve 116 is switched to the second state, so that the cuff pressure is decreased at a predetermined low rate (e.g., about 3 mmHg/sec). Based on the variation of respective amplitudes of heartbeat-synchronous pulses of the cuff-pulse-wave (CPW) signal $SM_1$ obtained during this slow decreasing of the cuff pressure, the CPU 129 determines a systolic, a mean, and a diastolic BP value $BP_{SYS}$, $BP_{MEAN}$, $BP_{DIA}$ of the patient according to a known oscillometric BP determining algorithm. More specifically, the CPU 129 determines, as the systolic BP value $BP_{SYS}$, a cuff pressure at the time when the pulse amplitudes significantly largely increase, determines, as the diastolic BP value $BP_{DIA}$, a cuff pressure at the time when the pulse amplitudes, significantly largely decrease, and determines, as the mean BP value $BP_{MEAN}$, a cuff pressure at the time when the pulse amplitudes become maximum. In addition, the CPU 129 determines a pulse rate of the patient based on the time interval between respective upper-peak points of two successive heartbeat-synchronous pulses of the CPW signal $SM_1$. The thus measured BP values and pulse rate are stored in the RAM 133 and displayed by the display 132. Then, the selector valve 116 is switched to the third state, so that the cuff pressure is quickly decreased or deflated.

Subsequently, the control of the CPU 129 goes to Step S108 to determine a relationship between monitor BP value MBP and magnitude $P_M$ of pressure pulse wave (i.e., voltage of the pressure-pulse-wave (PPW) signal $SM_2$) as shown in FIG. 9. More specifically, the CPU 129 newly reads in one heartbeat-synchronous pulse of the PPW signal $SM_2$ supplied from the PPW sensor 146, determines a maximum and a minimum magnitude $P_{Mmax}$, $P_{Mmin}$ of the one pulse, and determines the previously-indicated linear function based on the systolic and diastolic BP values $BP_{SYS}$, $BP_{DIA}$ of the patient measured at Step S107 and the thus determined maximum and minimum magnitudes $P_{Mmax}$, $P_{Mmin}$ of the one pulse of the PPW signal $SM_2$. Step S108 corresponds to the relationship determining means 174.

After the MBP-$P_M$ relationship shown in FIG. 9 is determined at Step S108, the control of the CPU 129 goes to Step S109 and the following steps to carry out a continuous BP monitoring operation. First, at Step S109, the CPU 129 judges whether the CPU 129 has read in one heartbeat-synchronous pulse of the PPW signal $SM_2$ supplied from the PPW sensor 146 being pressed at the optimum pressing force $P_{HDO}$. If a negative judgment is made at Step S109, the CPU 129 waits for detecting one pulse of the PPW signal $SM_2$. Meanwhile, if a positive judgment is made at Step S109, the control of the CPU 129 goes to Step S110 to determine a maximum (upper-peak) magnitude $P_{Mmax}$ and a minimum (lower-peak) magnitude $P_{Mmin}$ of the one pulse of the PPW signal $SM_2$. In addition, the CPU 129 determines a mean magnitude, $P_{Mmean}$, of the one pulse in a known manner. For example, the CPU 129 determines, as the mean magnitude $P_{Mmean}$ of one pulse, a signal-related one of the varycentric coordinates of an area defined by the waveform of the one pulse and a base line passing through the lower-peak point of the one pulse, the base line being indicated at two-dot chain line in FIG. 8. The pulse area is calculated by first subtracting the magnitude of the lower-peak point from the magnitude of each sampling point on the waveform of the one pulse of the signal $SM_2$ and then summing up the thus obtained values. Step S110 is followed by Step S111 to determine a systolic, a mean, and a diastolic BP value $MBP_{SYS}$, $MBP_{MEAN}$, $MBP_{DIA}$ (monitor BP values) of the patient, based on the maximum, mean, and minimum magnitudes $P_{Mmax}$, $P_{Mmean}$, $P_{Mmin}$ of the one pulse of the PPW signal $SM_2$ determined at Step S110, according to the MBP-$P_M$ relationship determined at Step S108. The CPU 129 controls the display 132 to display, on its image display panel, not only the thus determined monitor BP values MBP but also the waveform of the one pulse that is continuous with the respective waveforms of the prior pulses. Steps S110 and S111 correspond to the monitor-BP determining means 176.

Subsequently, the control of the CPU 129 goes to Step S112 to judge, based on a timer, whether a predetermined period of 10 to 20 minutes has passed after the current MBP-$P_M$ relationship is determined at Step S108. If a negative judgment is made at Step S112, the control goes back to Step S109 and the following steps to continue the continuous BP monitoring routine. Thus, the present BP monitor 100 successively determines, for each heartbeat-synchronous pulse of the signal $SM_2$, a systolic, a mean, and a diastolic BP value $MBP_{SYS}$, $MBP_{MEAN}$, $MBP_{DIA}$ of the patient and displays the determined BP values on the display 132. On the other hand, if a positive judgment is made at Step S112, the CPU 129 resets the timer to zero, and the control of the CPU 129 goes back to Step S102.

Figure 12:
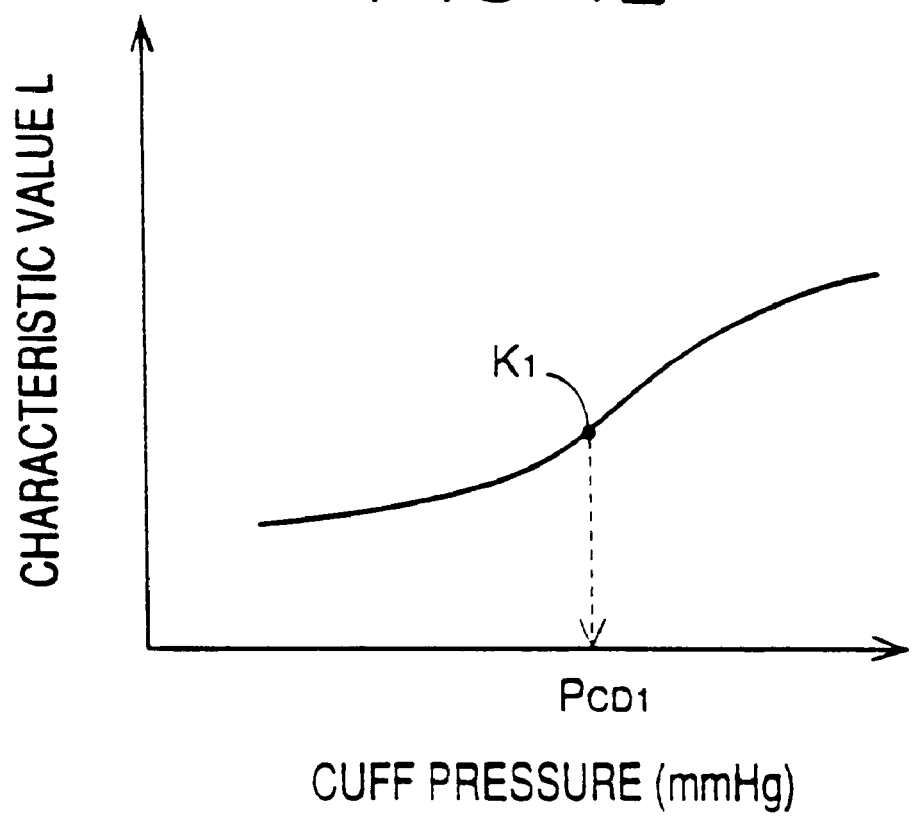
FIG. 12 is a graph showing a relationship between waveform characteristic L and cuff pressure that is determined by the control device of the BP monitor of FIG. 7.

In the current control cycle, a positive judgment is made at Step S102 because a MBP-$P_M$ relationship has been determined at Step S108 in the preceding control cycle. Then, the control of the CPU 129 goes to Step S103 to continuously or stepwise increase the cuff pressure from atmospheric pressure at a predetermined rate of 5 to 20 mmHg/sec and determine a characteristic of a lower-peak portion, F (FIG. 8), of the waveform of each of successive heartbeat-synchronous pulses of the signal $SM_2$ which is detected by the PPW sensor 146 when the cuff pressure is increased at the predetermined rate. This characteristic may be a length, L, of the lower-peak portion F defined by the magnitude $P_{Mmin}$ of the lower-peak point and a magnitude, $P_1$, greater by a predetermined amount than the magnitude $P_{Mmin}$, as illustrated in FIG. 8. Step S103 corresponds to the cuff-pressure increasing means 178 and the waveform-characteristic determining means 180. Step S103 is followed by Step S104 to judge whether the CPU 129 has identified a point or a time when the characteristic values L have significantly largely changed. For example, the CPU 129 differentiates the characteristic values L by subtracting, from each value $L_i$, the preceding value $L_{i-1}$ and determines, as an inflection point, $K_1$, a point corresponding to the greatest differential, as illustrated in FIG. 12.

When the cuff pressure takes values between the systolic and diastolic BP values of the patient, the lower-peak portion of the waveform of each pulse of the signal $SM_2$ is cut off, because the transmission of the PPW (i.e., blood flow) from the upstream side of the cuff 110 to the downstream side of the same is partially interrupted by the cuff 110. As the cuff pressure increases, the respective lengths of the cut-off portions of the pulses increase and accordingly the respective lengths L of the lower-peak portions of the pulses increase. Therefore, the above-indicated point $K_1$ is indicative of a time when the cuff pressure is equal to an actual or true diastolic BP value of the patient. Initially, a negative judgment is made at Step, S104, and the control of the CPU 129 goes back to Step S103. If a positive judgment is made at Step S104 while Steps S103 and S104 are repeated, the control goes to Step S105 to determine a cuff pressure, $P_{CD1}$, corresponding to the point $K_1$ identified at Step S104 and store it in the RAM 133. The cuff pressure $P_{CD1}$ is indicative of a true diastolic BP value of the patient. Step S105 functions as a diastolic BP determining means.

Step S105 is followed by Step S106 to judge whether the current MBP-$P_M$ relationship determined at Step S108 is accurate, based on the last diastolic BP value $MBP_{DIA}$ determined at Step S111 and the cuff pressure $P_{CD1}$ (i.e., true diastolic BP value) stored at Step S105. For example, the CPU 129 judges whether the absolute value of the difference of the last diastolic BP value $MBP_{DIA}$ and the cuff pressure $P_{CD1}$, i.e., $|MBP_{DIA}-P_{CD1}|$, is not greater than a reference value, $\Delta P_1$. This reference value is employed for guaranteeing the accuracy of the MBP-$P_M$ relationship: The reference value is, e.g., 5 mmHg. However, in the case where there is a difference between the cuff pressure $P_{CD1}$ and the diastolic BP value $BP_{DIA}$ measured at Step S107, the first difference $|MBP_{DIA}-P_{CD1}|$ is compared with a modified reference value obtained in advance by subtracting, from the reference value $\Delta P1$, the second difference between the cuff pressure $P_{CD1}$ and the diastolic BP value $BP_{DIA}$ measured using the cuff 110. Step S106 corresponds to the relationship-accuracy judging means 186.

If a positive judgment is made at Step S106, the current MBP-$P_M$ relationship is accurate and appropriate, therefore need not be updated. Therefore, the control of the CPU 129 skips Steps S107 and S108 and goes to Step S109 and the following steps, i.e., the continuous BP monitoring routine. On the other hand, if a negative judgment is made at Step S106, the control goes to Steps S107 and S108 to carry out an oscillometric BP measurement and determine a new MBP-$P_M$ relationship and subsequently goes to the continuous BP monitoring routine.

As is apparent from the foregoing description relating to the second embodiment shown in FIGS. 7 to 12, the CPU 129 of the control device 128 determines, at Step S103, a length L of a lower-peak portion F of the waveform of each of successive heartbeat-synchronous pulses of the PPW signal $SM_2$ which is detected while the cuff pressure is increased at a predetermined rate. At Step S105, the CPU 129 determines a cuff pressure $P_{CD1}$ corresponding to a point $K_1$ or time when the determined lengths L significantly largely change. At Step S106, the CPU 129 judges whether the current MBP-$P_M$ relationship determined at Step S108 is accurate, based on the determined cuff pressure $P_{CD1}$ and the last diastolic BP value $MBP_{DIA}$ last determined at Step S111. If a positive judgment is made at Step S106, an oscillometric BP measuring operation is not carried out at Step S107 and the current relationship is not updated at Step S108, i.e., is maintained. Thus, the patient is prevented from being pressed by the cuff 110. In addition, although the PPW sensor 146 is worn at a position downstream of the cuff 110, the continuous BP monitoring operation is continued at Steps S109–S111, without being interrupted due to the inflation of the cuff 110.

In the second embodiment, since the judgment about whether the current MBP-$P_M$ relationship is accurate is made based on the cuff pressure $P_{CD1}$ and the last monitor diastolic BP value $MBP_{DIA}$ determined at Step S111, it is more accurate than a judgment made based on a monitor diastolic BP value $MBP_{DIA}$ determined at Step S111 a predetermined time before, or the last diastolic BP value $BP_{DIA}$ measured at Step S107.

Referring next to FIGS. 13 through 16, there will be described a third embodiment of the present invention. The third embodiment relates to a continuous BP monitor 200 having the same hardware construction as that of the second embodiment shown in FIG. 7. The same reference numerals as used in the second embodiment are used to designate the corresponding elements or parts of the third embodiment and the description thereof is omitted.

Figure 13:
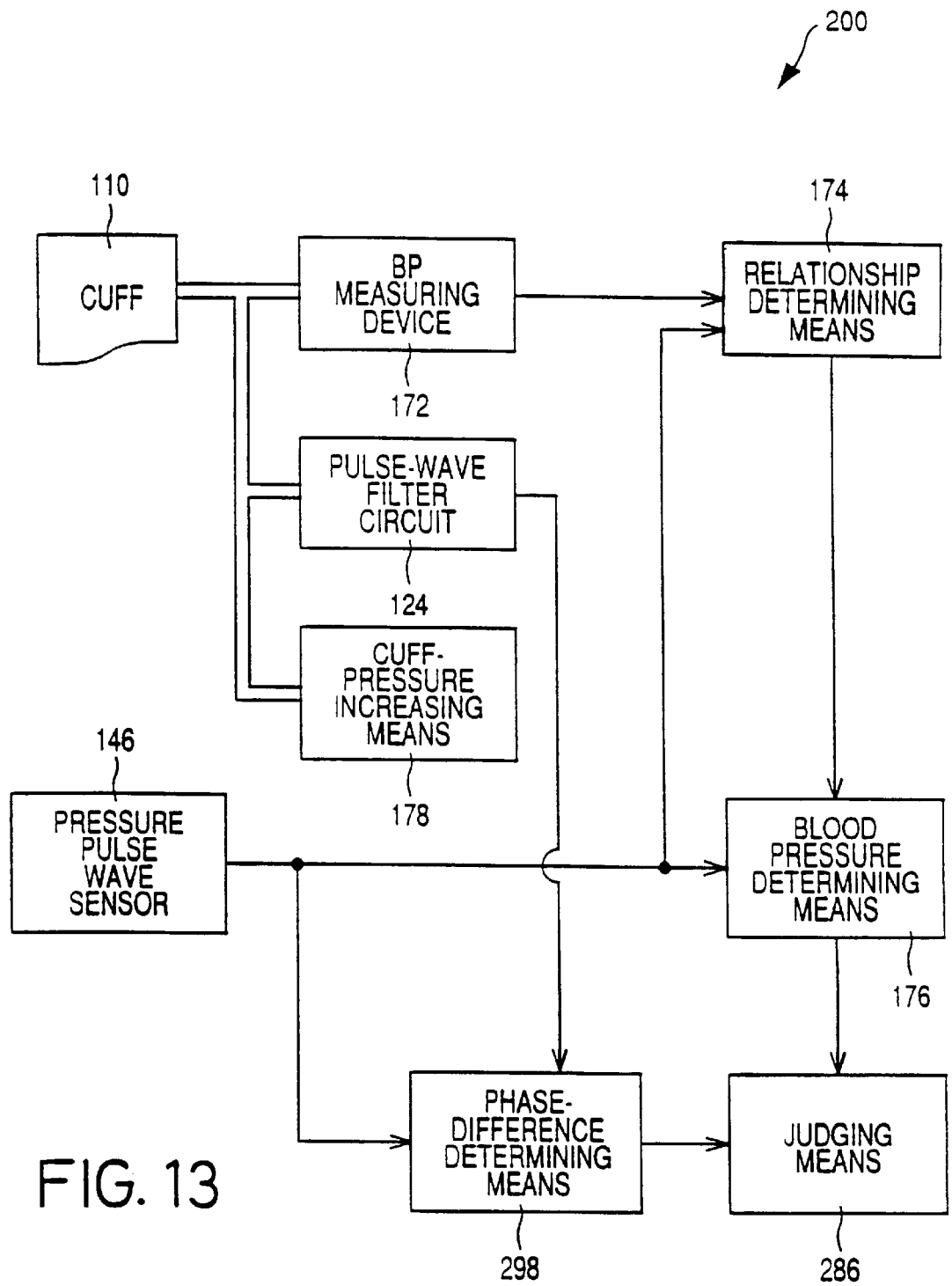
FIG. 13 is an illustrative view corresponding to FIG. 10, for explaining various functions of a control device of a continuous BP monitor as a third embodiment of the present invention.
Figure 15:
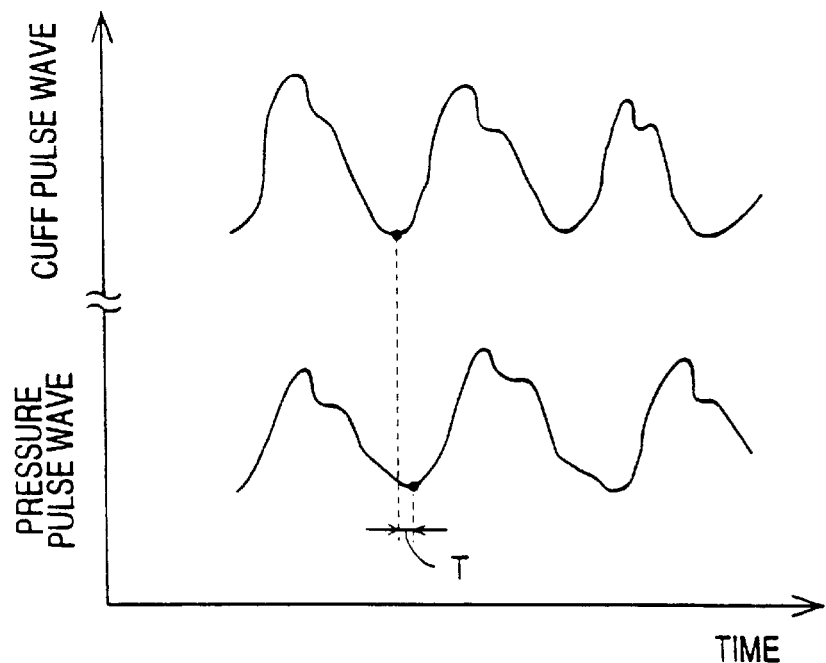
FIG. 15 is a graph showing an example of a cuff pulse wave (CPW) detected by a CPW sensor, and an example of a pressure pulse wave (PPW) detected by a PPW sensor, of the BP monitor of FIG. 13.

However, as shown in FIG. 13, the BP monitor 200 has different functions from those of the BP monitor 100 as the second embodiment. A control device 128 of the BP monitor 200 functions as a phase-difference determining means 298 which determines a phase difference, T (msec), of respective lower-peak points of each of successive heartbeat-synchronous pulses of a PPW signal $SM_2$ and a corresponding one of successive heartbeat-synchronous pulses of a CPW $SM_1$, as illustrated in the graph of FIG. 15. Those pulses of the signal $SM_2$ and those pulses of the signal $SM_1$ are detected by a PPW sensor 146 and a CPW sensor 114, 124, 130, respectively, when a pressure of a cuff 110 is increased at a predetermined rate by a cuff-pressure increasing means 178. The control device 128 also functions as a judging means 286 which judges whether an MBP-$P_M$ relationship determined by a relationship determining means 174 is accurate, based on one or more diastolic blood pressure values determined by a monitor-BP determining means 176 and a cuff pressure corresponding to a point, $K_2$, (FIG. 16) or a time when the phase differences T determined by the phase-difference determining means 298 significantly largely change.

Figure 11:
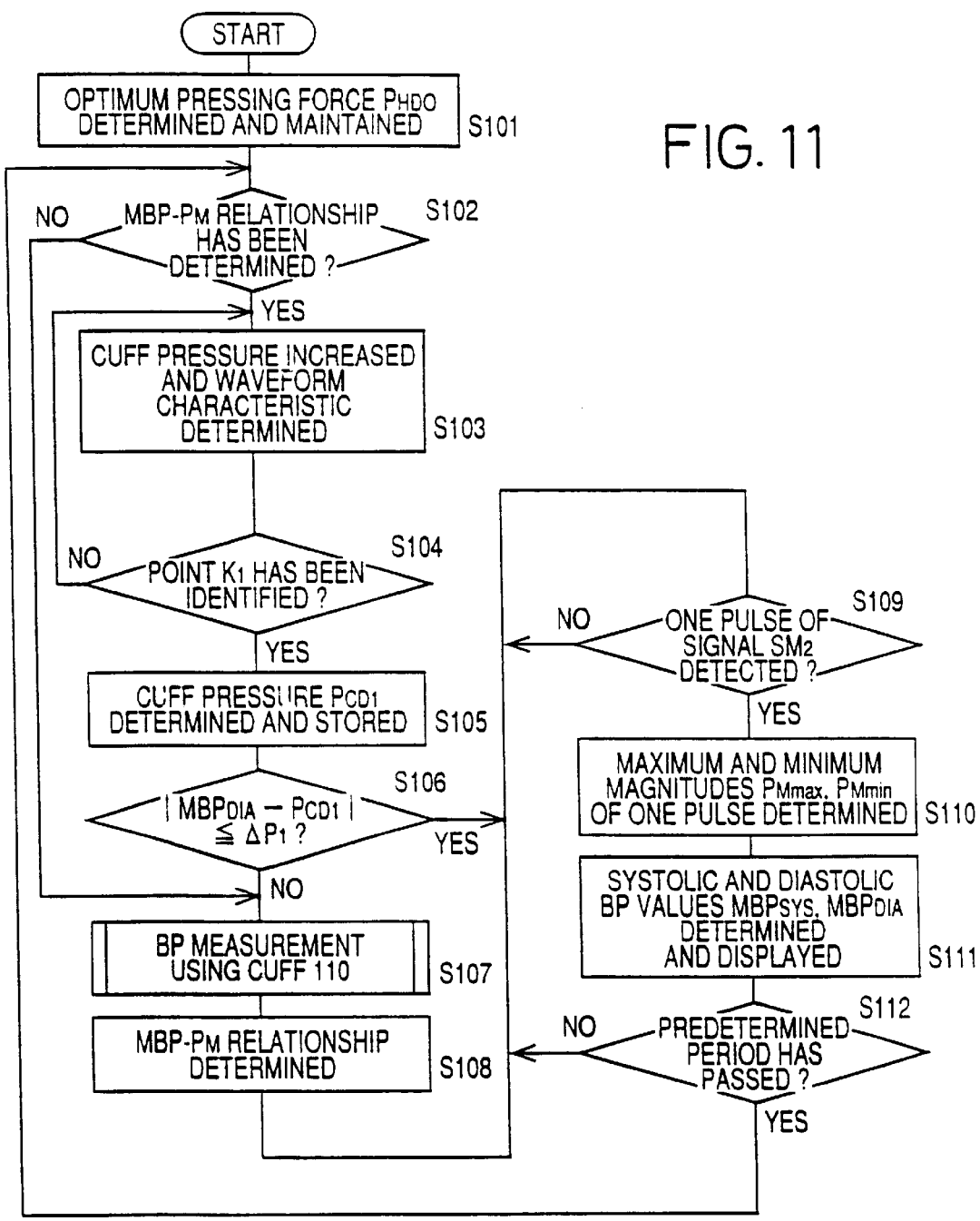
FIG. 11 is a flow chart representing a control routine according to which the BP monitor of FIG. 7 operates.
Figure 14:
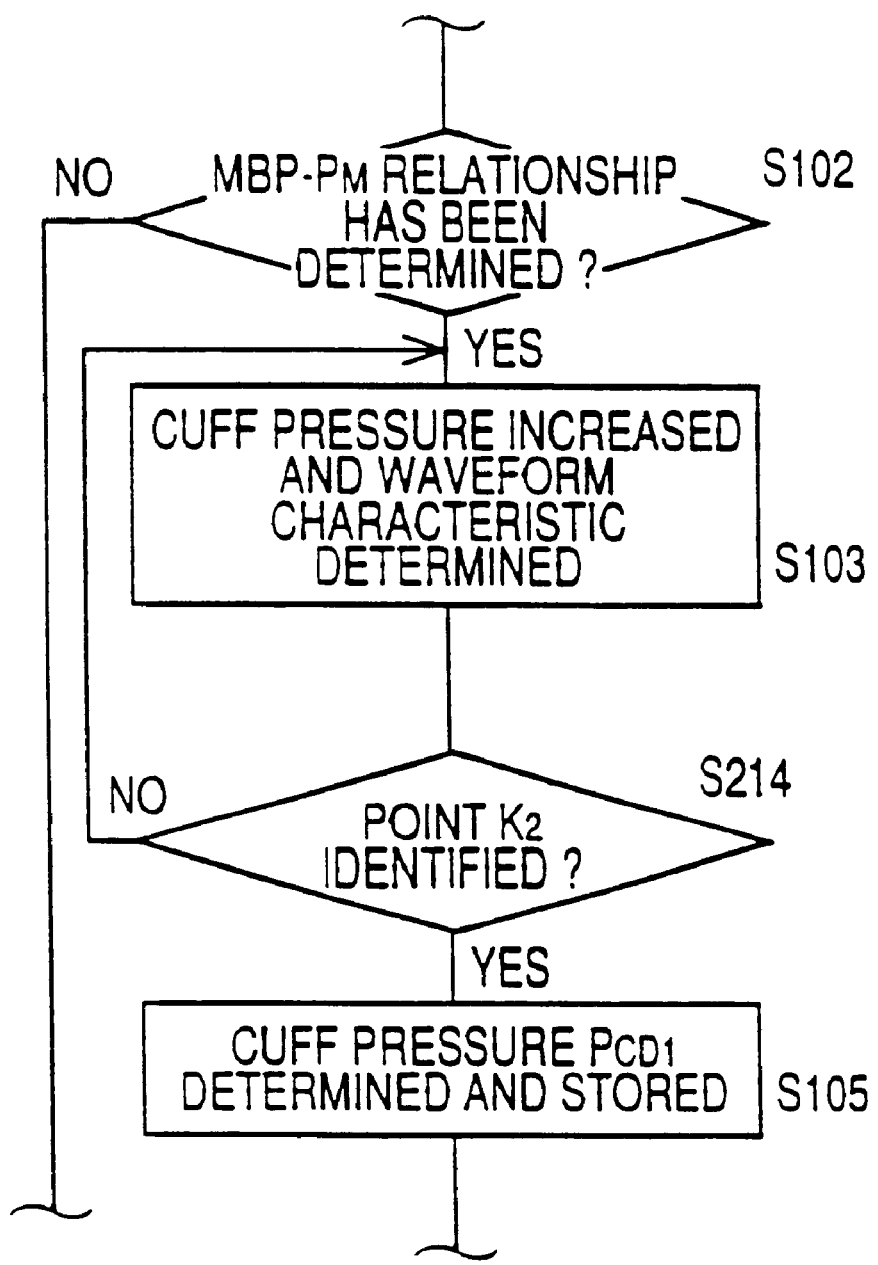
FIG. 14 is a flow chart corresponding to FIG. 11, representing a control routine according to which the BP monitor of FIG. 13 operates.

FIG. 14 shows a flow chart representing a control program according to which the control device 128 controls the operation of the present BP monitor 200. The flow chart of FIG. 14 is different from that of FIG. 11 only in that Step S104 of FIG. 11 is replaced by Step S214 of FIG. 14 that corresponds to the phase-difference determining means 298. At Step S103, a CPU 129 controls the cuff-pressure increasing means 178 to start increasing the cuff pressure.

Figure 16:
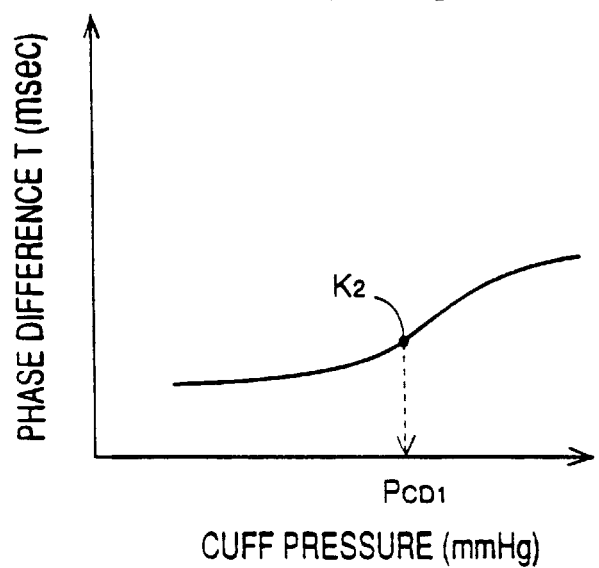
FIG. 16 is a graph showing a relationship between phase different T and cuff pressure that is determined by the control device of the BP monitor of FIG. 13.

At Step S214, first, the PPW sensor 146 and the CPW sensor 114, 124, 130 obtain the PPW signal $SM_2$ and the CPW signal $SM_1$, respectively, and the CPU 129 determines a phase difference T of respective lower-peak points of each of successive heartbeat-synchronous pulses of the PPW signal $SM_2$ and a corresponding one of successive heartbeat-synchronous pulses of the CPW $SM_1$, as shown in FIG. 15. Then, the CPU 129 judges whether the CPU 129 has identified a point or a time when the phase differences T have significantly largely changed. For example, the CPU 129 differentiates the phase-difference values T by subtracting, from each value $T_i$, the preceding value $T_{i-1}$ and determines, as an inflection point, $K_2$, a point corresponding to the greatest differential, as illustrated in FIG. 16. When the cuff pressure takes values between the systolic and diastolic BP values of the patient, the lower-peak portion of the waveform of each pulse of the PPW signal $SM_2$ is cut off, as described above. The point $K_2$ is indicative of a time when the cuff pressure is equal to an actual or true diastolic BP value of the patient. If a positive judgment is made at Step S214, the control goes to Step S105 to determine a cuff pressure $P_{CD1}$ corresponding to the point $K_2$ identified at Step S214 and store it in a RAM 133. Thus, the cuff pressure $P_{CD1}$ is indicative of an actual diastolic BP value of the patient. Step S105 is followed by Step S106 to judge whether the current MBP-$P_M$ relationship determined at Step S108 is accurate, based on the last diastolic BP value $MBP_{DIA}$ determined at Step S111 and the cuff pressure $P_{CD1}$ stored at Step S105. For example, the CPU 129 judges whether the absolute value of the difference of the last diastolic BP value $MBP_{DIA}$ and the cuff pressure $P_{CD1}$, i.e., $|MBP_{DIA}-P_{CD1}|$, is not greater than a reference value, $\Delta P_1$. This reference value is, e.g., 5 mmHg.

As is apparent from the foregoing description relating to the third embodiment shown in FIGS. 13 to 16, the CPU 129 of the control device 128 determines, at Step S214, a phase difference T of respective lower-peak points of each of the pulses of the PPW signal $SM_2$ and a corresponding one of the pulses of the PPW signal $SM_1$ which are obtained by the PPW sensor 146 and the CPW sensor 114, 124, 130 while the cuff pressure is increased at a predetermined rate at Step S103. At Step S105, the CPU 129 determines a cuff pressure $P_{CD1}$ corresponding to a point $K_2$ or time when the determined phase differences T significantly largely change. At Step S106, the CPU 129 judges whether the current MBP-$P_M$ relationship determined at Step S108 is accurate, based on the determined cuff pressure $P_{CD1}$ and the last diastolic BP value $MBP_{DIA}$ last determined at Step S111. If a positive judgment is made at Step S106, an oscillometric BP measuring operation is not carried out at Step S107 and the current relationship is maintained without being updated at Step S108. Thus, the patient is prevented from being pressed by the cuff 110. In addition, although the PPW sensor 146 is worn at a position downstream of the cuff 110, a continuous BP monitoring operation may be continued at Steps S109–S111 without being interrupted due to the inflation of the cuff 110.

Figure 17:
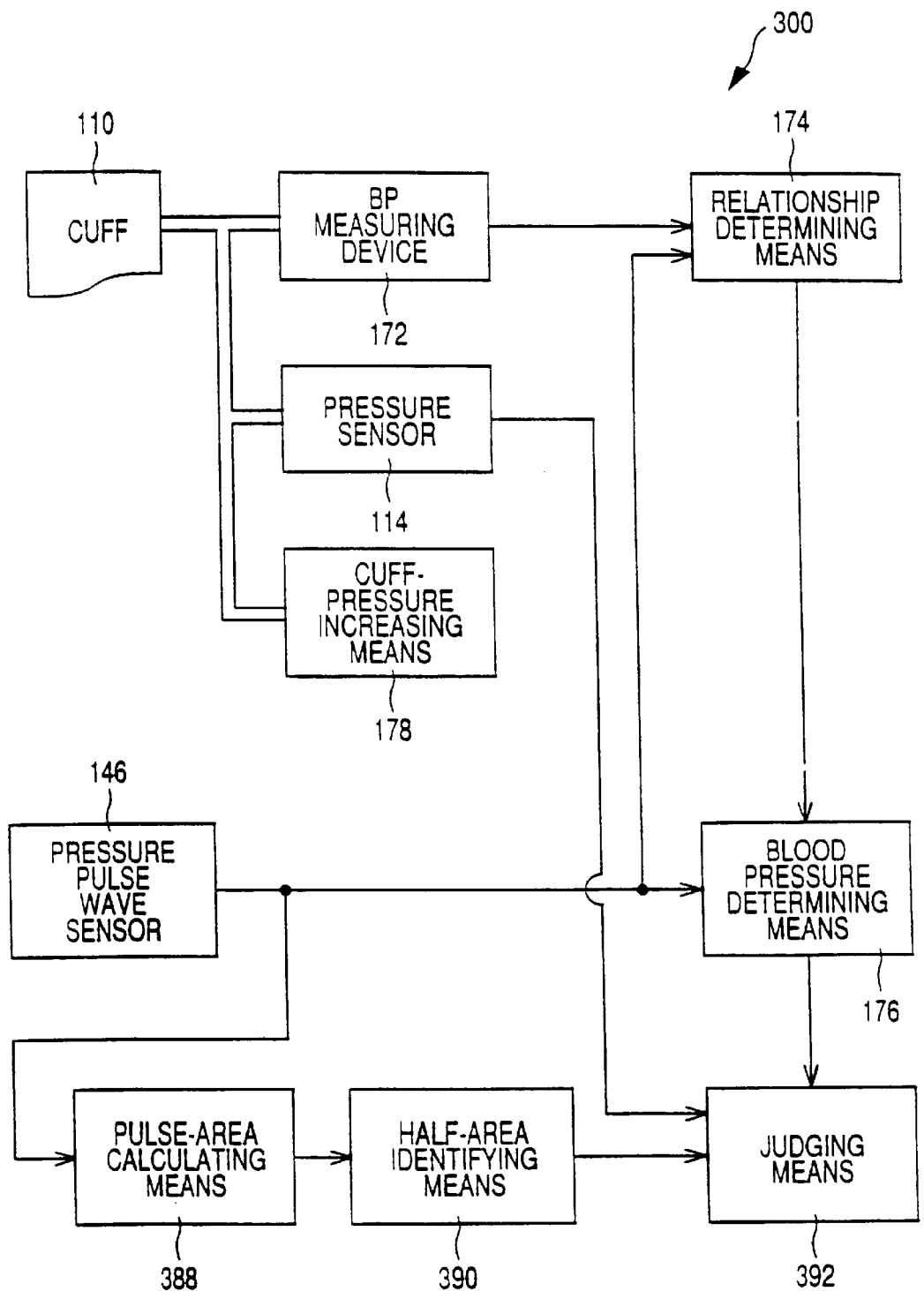
FIG. 17 is an illustrative view corresponding to FIG. 10, for explaining various functions of a control device of a continuous BP monitor as a fourth embodiment of the present invention.
Figure 18:
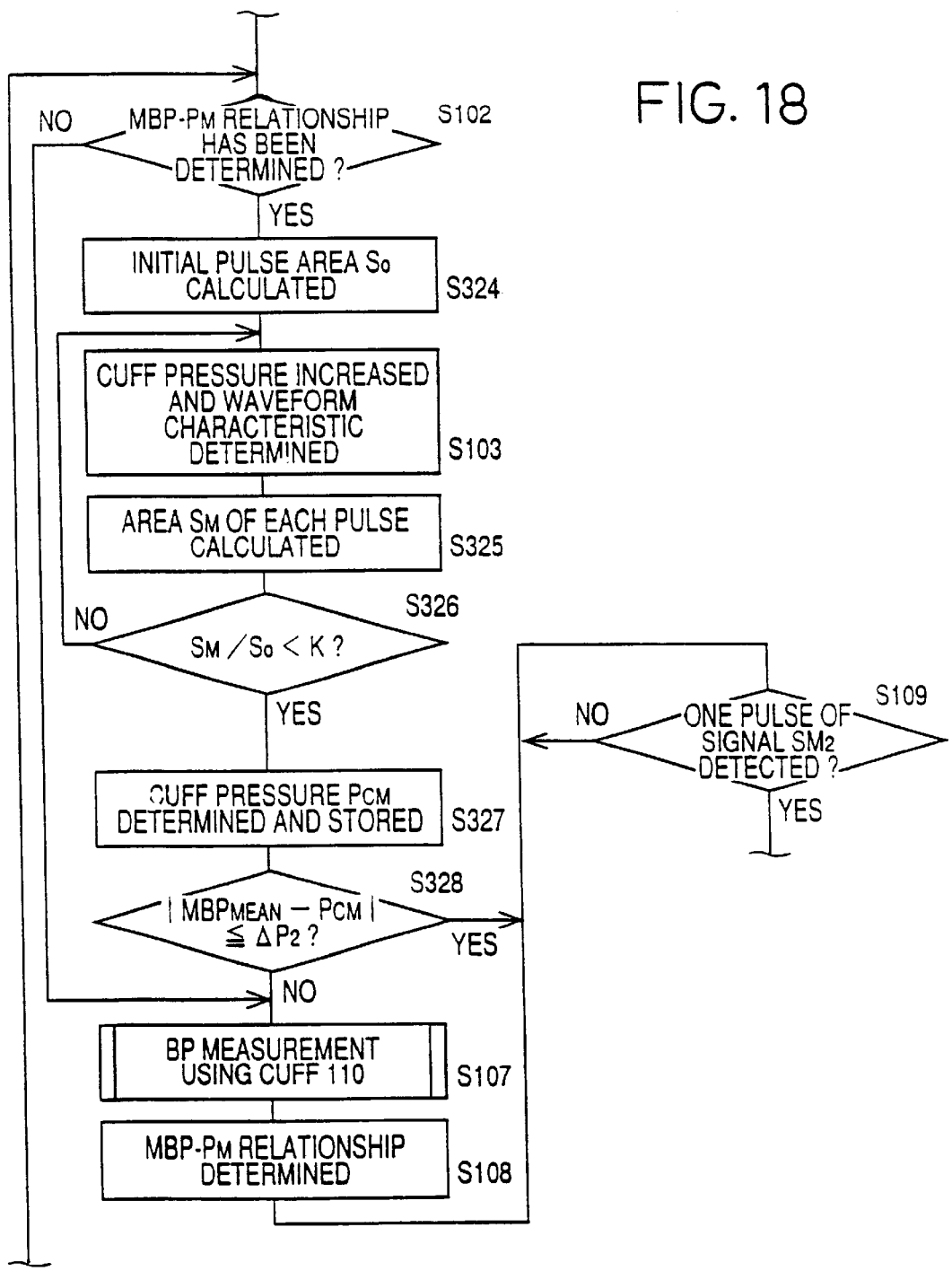
FIG. 18 is a flow chart corresponding to FIG. 11, representing a control routine according to which the BP monitor of FIG. 17 operates.

Referring to FIGS. 17 and 18, there will be described a fourth embodiment of the present invention. The fourth embodiment relates to a continuous BP monitor 300 having the same hardware construction as that of the second embodiment shown in FIG. 7. The same reference numerals as used in the second embodiment are used to designate the corresponding elements or parts of the fourth embodiment and the description thereof is omitted.

However, as shown in FIG. 17, the BP monitor 300 has different functions from those of the BP monitor 100 as the second embodiment. A control device 128 of the BP monitor 300 functions as a pulse-area calculating means 388 which calculates an area, $S_M$, defined by each of successive heartbeat-synchronous pulses of a PPW signal $SM_2$ which is obtained by a PPW sensor 146 when a pressure of an inflatable cuff 110 is increased at a predetermined rate by a cuff-pressure increasing means 178. The control device 128 also functions as a half-area identifying means 390 which identifies that the pulse areas $S_M$ calculated by the pulse-area calculating means 388 have decreased to half an initial pulse area, $S_0$, measured before the cuff-pressure increasing means 178 starts increasing the cuff pressure; and a judging means 392 which judges whether a MBP-$P_M$ relationship determined by a relationship determining means 174 is accurate, based on one or more mean BP values $MBP_{MEAN}$ determined by a monitor-BP determining means 176 and a cuff pressure corresponding to a time when the pulse areas $S_M$ have decreased to half the initial pulse area $S_0$.

FIG. 18 shows a flow chart representing a control program according to which the control device 128 controls the operation of the present BP monitor 300. The flow chart of FIG. 18 is different from that of FIG. 11 in that in FIG. 18, Step S324 is inserted between Steps S102 and S103 of FIG. 11 and Steps S325, S326, S327, and S328 replace Steps S104, S105, and S106 of FIG. 11.

At Step S324, a CPU 129 of the control device 128 calculates an area $S_0$ defined by one heartbeat-synchronous pulse of the signal $SM_2$ produced by the PPW sensor 146 before the cuff pressure is increased at Step S103. For example, the pulse area $S_0$ is defined by the waveform of one pulse and a base line, indicated at two-dot chain line in FIG. 8, which passes through the lower-peak point of the one pulse. The pulse area $S_0$ is calculated by first subtracting the magnitude of the lower-peak point from the magnitude of each sampling point on the waveform of the one pulse of the signal $SM_2$ and then summing up the thus obtained values.

After the increasing of the cuff pressure at a predetermined rate is started at Step S103, the CPU 129 calculates, at Step S325, an area $S_M$ of each of heartbeat-synchronous pulses of the PPW signal $SM_2$ obtained while the cuff pressure is increased, in the same manner as that employed at Step S324. Step S325 corresponds to the pulse-area calculating means 388.

Step S325 is followed by Step S326 to calculate a ratio, $S_M/S_0$, of each pulse area $S_M$ to the initial pulse area $S_0$ and judge whether the ratio $S_M/S_0$ has decreased down to smaller than a reference value, K, which is selected at, e.g., ½ providing a basis for judging whether the cuff pressure has increased up to a value equal to a mean BP value of the patient. Step S326 corresponds to the half-area identifying means 390.

If a negative judgment is made at Step S326, Steps S103, S325 and S326 are repeated. Meanwhile, if a positive judgment is made at Step S326, the control of the CPU 129 goes to Step S327 to determine a cuff pressure, $P_{CM}$, at the time when the pulse areas $S_M$ have decreased to half the initial pulse area $S_0$. This cuff pressure $P_{CM}$ is equal to an actual mean BP value of the patient. The cuff pressure $P_{CM}$ is stored in a RAM 133. Step S327 functions as a mean BP value determining means.

Step S327 is followed by Step S328 to judge whether the current MBP-$P_M$ relationship determined at Step S108 is accurate, based on the last mean BP value $MBP_{MEAN}$ determined at Step S111 and the cuff pressure $P_{CM}$ (i.e., actual mean BP value) stored at Step S327. For example, the CPU 129 judges whether the absolute value of the difference of the last mean BP value $MBP_{MEAN}$ and the cuff pressure $P_{CM}$, i.e., $|MBP_{MEAN}-P_{CM}|$, is not greater than a reference value, $\Delta P_2$. This reference value is employed for guaranteeing the accuracy of the MBP-$P_M$ relationship. The reference value is, e.g., 5 mmHg. However, in the case where there is a difference between the cuff pressure $P_{CM}$ and the mean BP value $BP_{MEAN}$ measured at Step S107, the first difference $|MBP_{MEAN}-P_{CM}|$ is compared with a modified reference value obtained in advance by subtracting, from the reference value $\Delta P_2$, the second difference between the cuff pressure $P_{CM}$ and the mean BP value $BP_{MEAN}$ measured using the cuff 110. Step S328 corresponds to the relationship-accuracy judging means 392.

If a positive judgment is made at Step S328, the current MBP-$P_M$ relationship is accurate and appropriate, therefore need not be updated. Therefore, the control of the CPU 129 skips Steps S107 and S108 and goes to Step S109 and the following steps to continue the continuous BP monitoring routine. On the other hand, if a negative judgment is made at Step S328, the control goes to Steps S107 and S108 to carry out an oscillometric BP measurement and determine a new MBP-$P_M$ relationship and subsequently resumes the continuous BP monitoring routine.

As is apparent from the foregoing description relating to the fourth embodiment shown in FIGS. 17 and 18, the CPU 129 of the control device 128 determines, at Step S325, an area $S_M$ of each of heartbeat-synchronous pulses of the PPW signal $SM_2$ obtained by the PPW sensor 146 while the cuff pressure is increased at a predetermined rate at Step S103. At Step S326, the CPU 129 judges whether the pulse areas $S_M$ have decreased to half the initial pulse area $S_0$ and determines, at Step S327, a cuff pressure $P_{CM}$ corresponding to a time when the pulse areas $S_M$ have become half. At Step S328, the CPU 129 judges whether the current MBP-$P_M$ relationship determined at Step S108 is accurate, based on the determined cuff pressure $P_{CM}$ and the last mean BP value $MBP_{MEAN}$ last determined at Step S111. If a positive judgment is made at Step S328, an oscillometric BP measuring operation is not carried out at Step S107 and the current relationship is maintained without being updated at Step S108. Thus, the patient is prevented from being pressed by the cuff 110. In addition, although the PPW sensor 146 is worn at a position downstream of the cuff 110, a continuous BP monitoring operation may be continued at Steps S109–S111, without being interrupted due to the inflation of the cuff 110.

Figure 19:
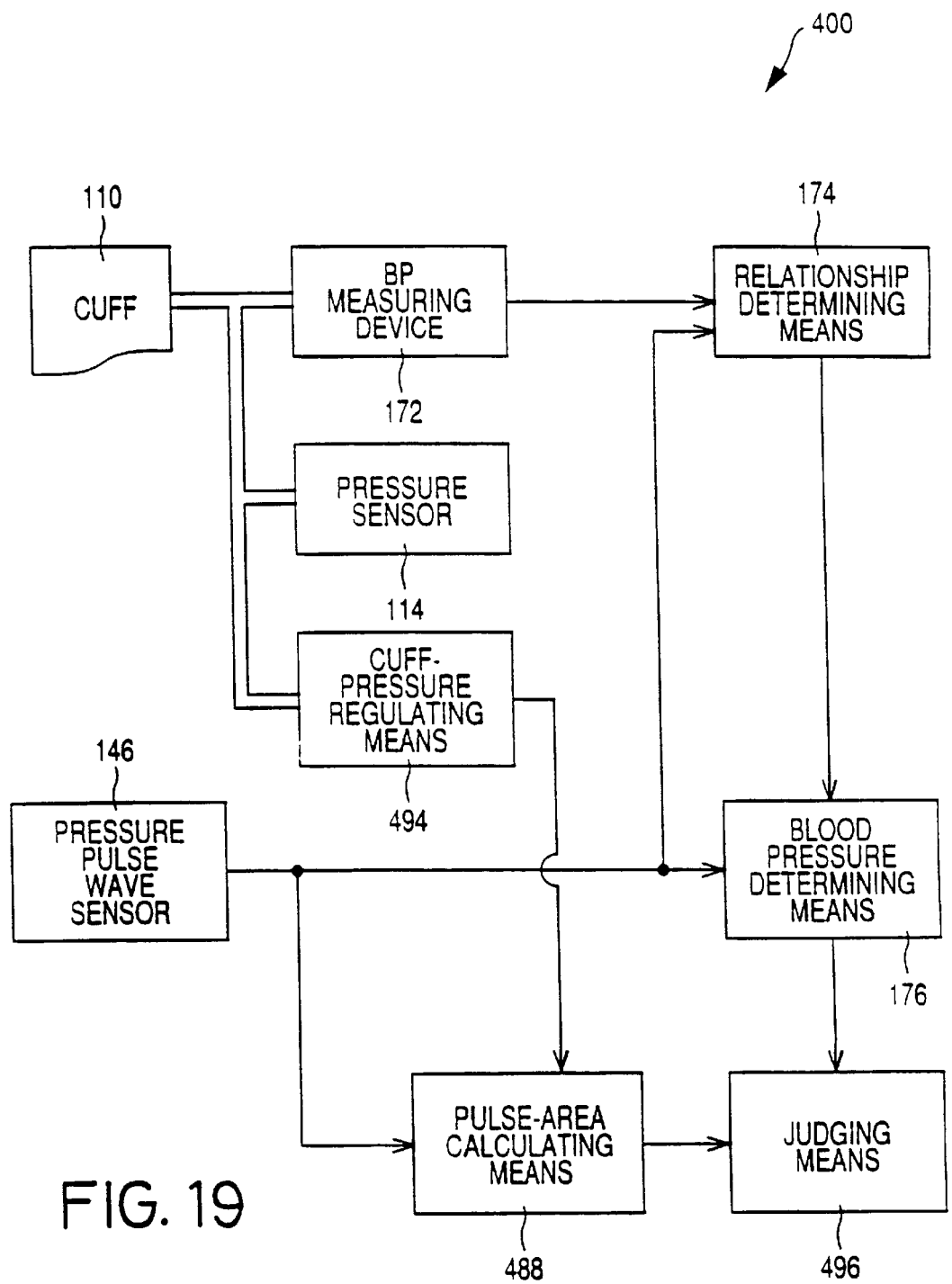
FIG. 19 is an illustrative view corresponding to FIG. 10, for explaining various functions of a control device of a continuous BP monitor as a fifth embodiment of the present invention.
Figure 20:
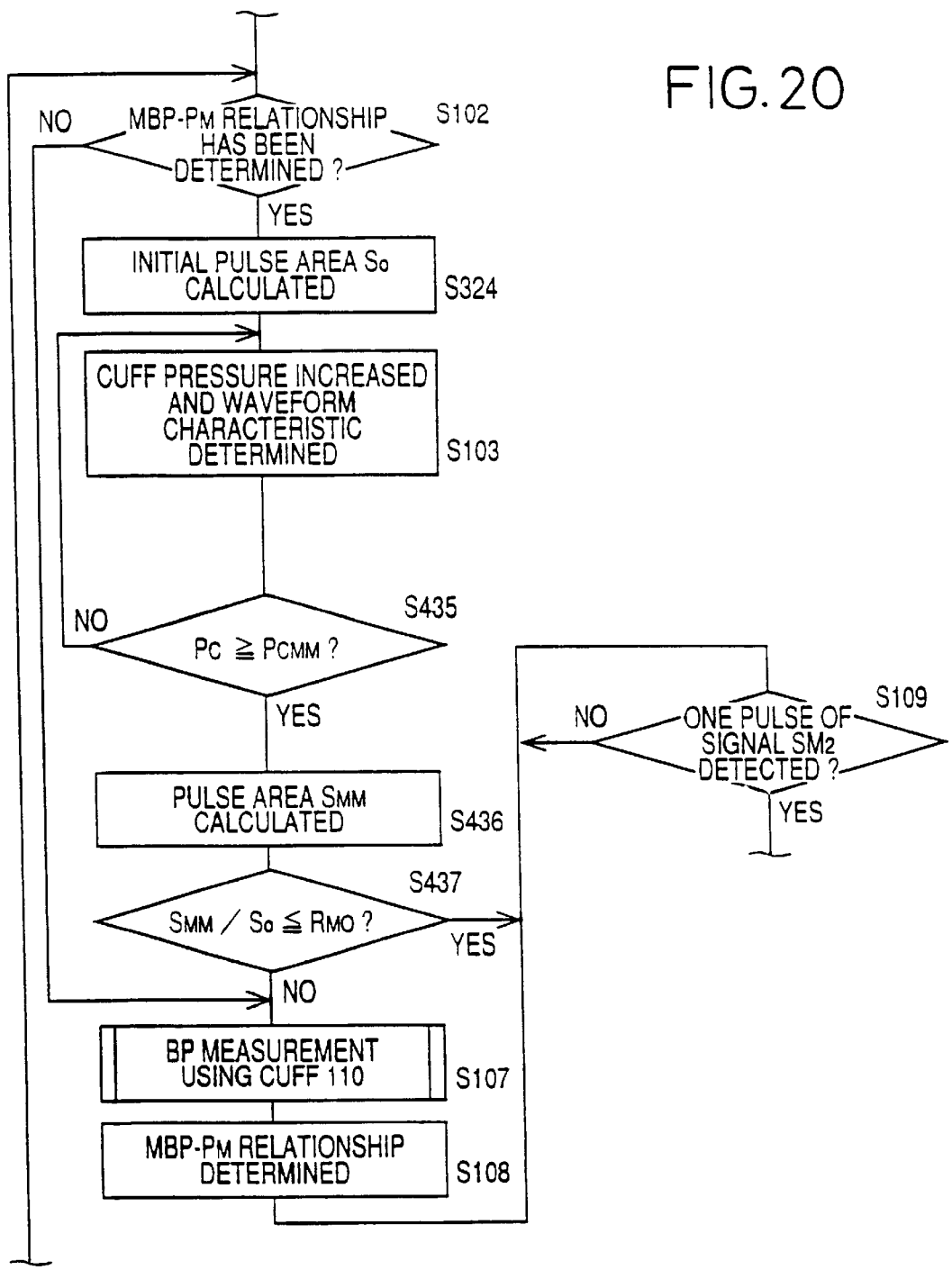
FIG. 20 is a flow chart corresponding to FIG. 11, representing a control routine according to which the BP monitor of FIG. 19 operates.

Referring to FIGS. 19 and 20, there will be described a fifth embodiment of the present invention. The fifth embodiment relates to a continuous BP monitor 400 having the same hardware construction as that of the second embodiment shown in FIG. 7. The same reference numerals as used in the second embodiment are used to designate the corresponding elements or parts of the third embodiment and the description thereof is omitted.

However, as shown in FIG. 19, the BP monitor 400 has different functions from those of the BP monitor 100 as the second embodiment. A control device 128 of the BP monitor 400 functions as a cuff-pressure regulating means 494 which increases a pressure of a cuff 110 up to a predetermined target pressure, $P_{CMM}$, and holds the cuff pressure at the target value $P_{CMM}$. The control device 128 also functions as a pulse-area calculating means 488 which calculates an area, $S_{MM}$, defined by each of successive heartbeat-synchronous pulses of a PPW signal $SM_2$ which is obtained by a PPW sensor 146 when the cuff pressure is held at the target value $P_{CMM}$ by the cuff-pressure regulating means 494. The control device 128 also functions as a judging means 496 which judges whether a MBP-$P_M$ relationship determined by a relationship determining means 174 is accurate, based on one or more pulse areas $S_{MM}$ calculated by the pulse-area calculating means 488.

FIG. 20 shows a flow chart representing a control program according to which the control device 128 controls the operation of the present BP monitor 400. The flow chart of FIG. 20 is different from that of FIG. 11 in that in FIG. 20, Step S324 is inserted between Steps S102 and S103 of FIG. 11 and Steps S435, S436, and S437 replace Steps S104, S105, and S106 of FIG. 11. Step S324 of FIG. 20 is the same as Step S324 of FIG. 18, i.e., is provided for calculating an initial pulse area $S_0$. At Step S103, the increasing of the cuff pressure is started and, at Step S435, a CPU 129 of the control device 128 judges whether the cuff pressure has reached a predetermined target value $P_{CMM}$. For example, the target value is predetermined to be higher than the last mean BP value $MBP_{MEAN}$ determined at Step S111, by an excess value, β, of, e.g., 5 to 10 mmHg. Steps S103 and S435 correspond to the cuff-pressure regulating means 494.

At an early stage, negative judgments are made at Step S435. Meanwhile, a positive judgment is made at Step S435 while Steps S103 and S435 are repeated. Then, the cuff pressure is held at the target value $P_{CMM}$ and the control goes to Step S436 to calculate an area $S_{MM}$ of each of heartbeat-synchronous pulses of the PPW signal $SM_2$ produced by the PPW sensor 146 while the cuff pressure is maintained at the target value $P_{CMM}$. Step S436 corresponds to the pulse-area calculating means 488. Step S436 is followed by Step S437 to judge whether a ratio, $S_{MM}/S_0$, of each pulse area $S_{MM}$ to the initial pulse area $S_0$ is not greater than a predetermined reference value, $R_{MO}$. The reference value $R_{MO}$ is predetermined such that in the case where the mean BP value of the patient plus the excess value β amounts to a value falling within the range of the target value $P_{CMM}\pm 5$ mmHg, the ratio $S_{MM}/S_0$ is not greater than the reference value $R_{MO}$.

If a positive judgment is made at Step S437, the current MBP-$P_M$ relationship is accurate and need not be updated. Therefore, the control of the CPU 129 skips Steps S107 and S108 and goes to Step S109 and the following steps to continue the continuous BP monitoring routine. On the other hand, if a negative judgment is made at Step S437, the control goes to Steps S107 and S108 to carry out an oscillometric BP measurement and determine a new MBP-$P_M$ relationship and subsequently resumes the continuous BP monitoring routine.

As is apparent from the foregoing description relating to the fifth embodiment shown in FIGS. 19 and 20, the CPU 129 of the control device 128 calculates, at Step S436, an area $S_{MM}$ of each of heartbeat-synchronous pulses of the PPW signal $SM_2$ obtained by the PPW sensor 146 while the cuff pressure is held at the target value $P_{CMM}$ at Step S435. At Step S437, the CPU 129 judges whether the current MBP-$P_M$ relationship determined at Step S108 is accurate, based on the ratio $S_{MM}/S_0$ of each pulse area $S_{MM}$ to the initial pulse area $S_0$. If a positive judgment is made at Step S437, an oscillometric BP measuring operation is not carried out at step S107 and the current relationship is maintained without being updated at Step S108. Thus, the patient is prevented from being pressed by the cuff 110. In addition, although the PPW sensor 146 is worn at a position downstream of the cuff 110, a continuous BP monitoring operation may be continued at Steps S109–S111, without being interrupted due to the inflation of the cuff 110.

Figure 21:
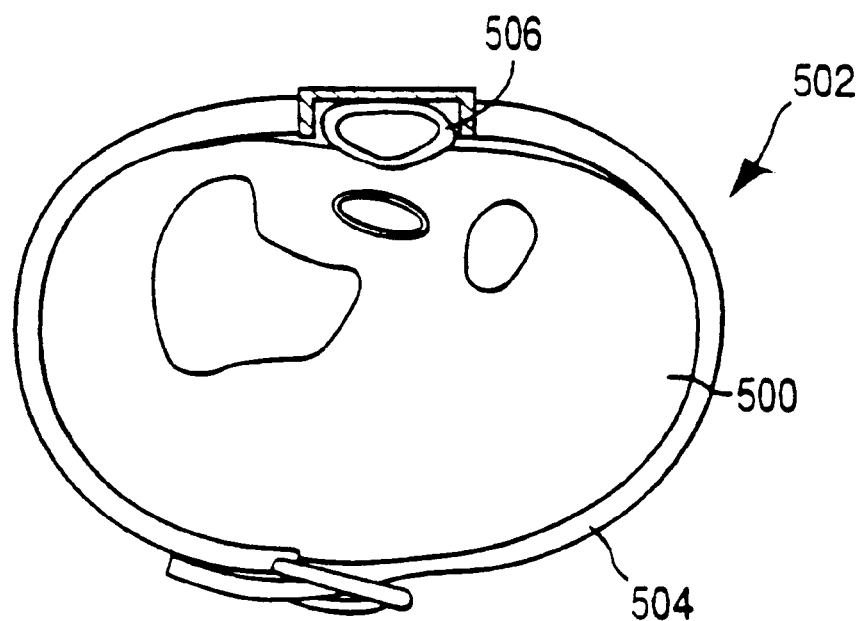
FIG. 21 is a cross-section view of a cuff pulse wave (CPW) sensor employed by a continuous BP monitor as a sixth embodiment of the present invention.

In the third embodiment shown in FIGS. 13–16, the BP monitor 200 may additionally include an exclusive cuff pulse wave (CPW) sensor 502 as shown in FIG. 21. In this sixth embodiment, the CPW sensor 502 is set on a wrist 500 different from a wrist 142 on which the PPW sensor 146 is set. The CPW sensor 502 includes a belt 504 which is adapted to be wound around the wrist 500, and a small inflatable bag 506 which is secured to an inner surface of the belt 504 and is inflatable inwardly. In use, the CPW sensor 502 is set on the wrist 500 such that the bag 506 is positioned right above a radial artery located between a tendon and a radius bone in the wrist 500. In this case, the bag 506 can advantageously press, when being inflated, the radial artery without being interfered with by the tendon and/or the radius. An air-supply device and a pressure sensor (not shown) are connected to the bag 506.

In each of the second to fifth embodiments, the BP measuring device 172 performs, at Step S107, an oscillometric BP measuring method in which one or more BP values are determined based on the variation of respective amplitudes of heartbeat-synchronous pulses of the cuff pulse wave (i.e., CPW signal $SM_1$) obtained while the cuff pressure is changed. However, it is possible to employ, in place of the oscillometric method, a Korotkoff-sound method in which one or more BP values are determined based on the first detection and/or last detection (i.e., disappearance) of Korotkoff sounds detected by a microphone while the cuff pressure is changed.

While in each of the second to sixth embodiments the judging means 182, 286, 392, 496 uses only the last diastolic or mean BP value $MBP_{DIA}$, $MBP_{MEAN}$ determined by the monitor-BP determining means 176, for evaluating the accuracy of the MBP-$P_M$ relationship, it is possible to use, for the same purpose, an average of a plurality of last diastolic or mean BP values $MBP_{DIA}$, $MBP_{MEAN}$ determined based on a plurality of last pulses detected by the PPW sensor 146. In the latter case, even if an abnormal lower-peak or mean magnitude of a PPW pulse may be detected due to, e.g., a physical motion of the patient, the adverse influence of that magnitude to the judgment of the judging means 182, 286, 392, 496 is effectively reduced.

Although in each of the second to sixth embodiments the calibration of the MBP-$P_M$ relationship is carried out at Steps S107 and S108 at the predetermined period employed at Step S112, it is possible to replace Step S112 by a step where the CPU 129 judges whether monitor BP values MBP determined by the BP determining means 176 have abnormally changed. In the latter case, if a positive judgment is made at that step, the control of the CPU 129 goes back to Step S102.

Referring next to FIGS. 22 through 25, there will be described a seventh embodiment of the present invention.

The seventh embodiment relates to a continuous BP monitor 600 having the same hardware construction as that of the second embodiment shown in FIG. 7. The same reference numerals as used in the second embodiment are used to designate the corresponding elements or parts of the seventh embodiment and the description thereof is omitted.

Figure 22:
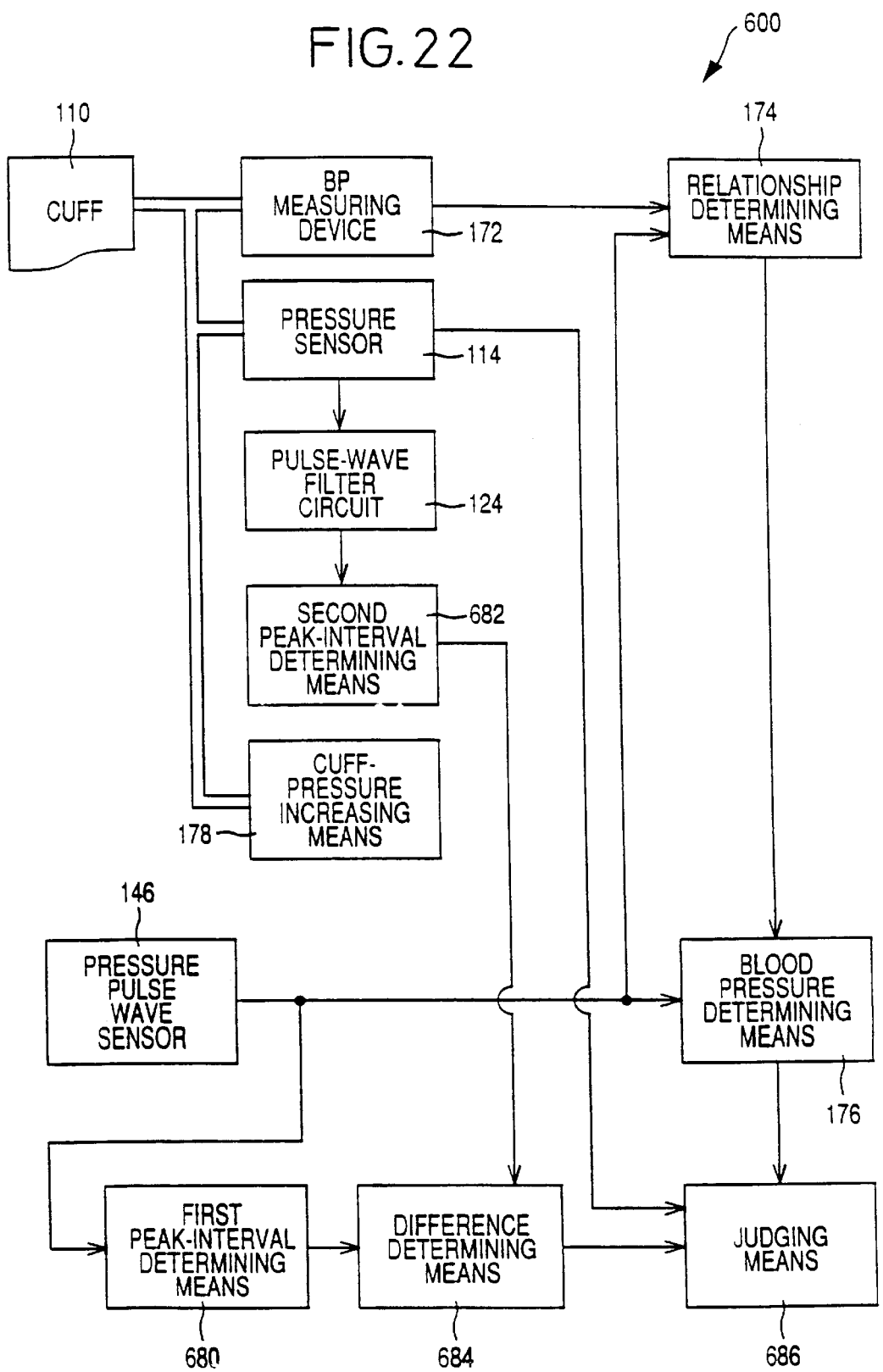
FIG. 22 is an illustrative view corresponding to FIG. 10, for explaining various functions of a control device of a continuous BP monitor as a seventh embodiment of the present invention.

However, as shown in FIG. 22, the BP monitor 600 has different functions from those of the BP monitor 100 as the second embodiment. A control device 128 of the BP monitor 600 functions as a first peak-interval determining means 680 which determines a first interval, $D_i$ (FIG. 23), between an upper-peak point and a lower-peak point of each of successive heartbeat-synchronous pulses of a distal pulse wave, i.e., PPW signal $SM_2$ which is detected by a PPW sensor 146 when the pressure of an inflatable cuff 110 is increased at a predetermined rate by a cuff-pressure increasing means 178; as a second peak-interval determining means 682 which determines a second interval, $d_i$, between an upper-peak point and a lower-peak point of each of successive heartbeat-synchronous pulses of a cuff pulse wave, i.e., CPW signal $SM_1$ which is detected by a cuff pulse wave sensor 114, 124, 130 including a pulse-wave filter circuit 124, when the pressure of the cuff 110 is increased at the predetermined rate by the cuff-pressure increasing means 178; as a difference determining means 684 which determines a difference between the first interval of each of the successive heartbeat-synchronous pulses of the pressure pulse wave (PPW) and the second interval of a corresponding one of the successive heartbeat-synchronous pulses of the cuff pulse wave (CPW); and a judging means 686 which judges whether the relationship determined by a relationship determining means 174 is accurate, based on one or more diastolic BP values $MBP_{DIA}$ determined by a monitor-BP determining means 176 and a cuff pressure corresponding to a point, $K_3$ (FIG. 25), or time when the differences determined by the difference determining means 684 significantly largely change.

Figure 24:
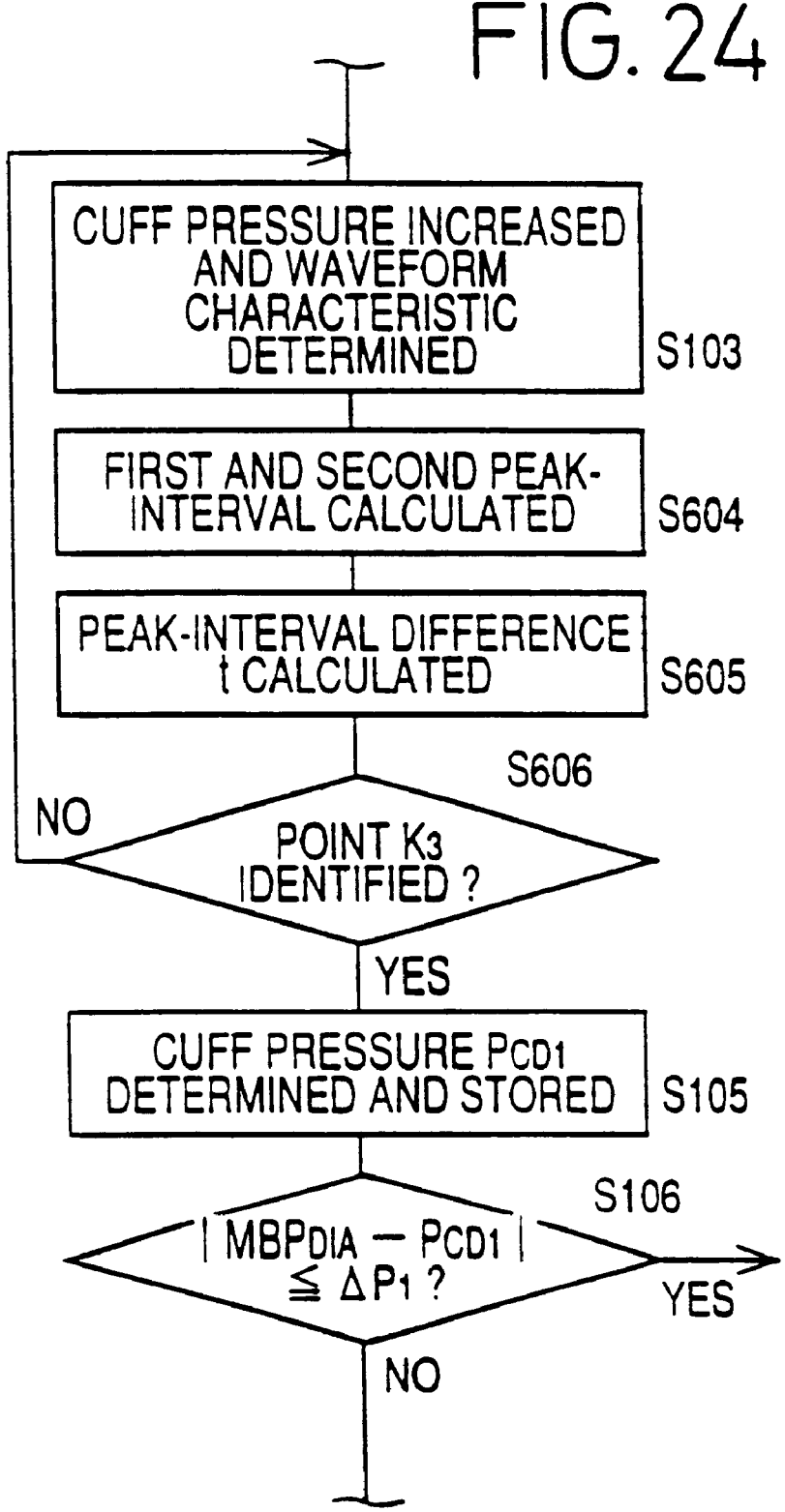
FIG. 24 is a flow chart corresponding to FIG. 11, representing a control routine according to which the BP monitor of FIG. 22 operates.

FIG. 24 shows a flow chart representing a control program according to which the control device 128 controls the operation of the present BP monitor 600. The flow chart of FIG. 24 is different from that of FIG. 11 in that Step S104 of FIG. 11 is replaced by Steps S604, S605, and S606 of FIG. 24.

At Step S103, a CPU 129 of the control device 128 controls the cuff-pressure increasing means 178 to start increasing the cuff pressure from atmospheric pressure at a predetermined rate of, e.g., 5 to 20 mmHg/sec. At Step S604, first, the PPW sensor 146 and the CPW sensor 114, 124, 130 obtain the PPW signal $SM_2$ and the CPW signal $SM_1$ as shown in a top and a bottom of the graph of FIG. 23, respectively, and the CPU 129 determines a time interval $D_i$ (i=1, 2, ... ) between an upper-peak point, $P_{M2max}$, and a lower-peak point, $P_{M2min}$, of each of successive heartbeat-synchronous pulses of the PPW and a time interval $d_i$ (i=1, 2, ... ) between an upper-peak point, $P_{M1max}$, and a lower-peak point, $P_{M1min}$, of each of successive heartbeat-synchronous pulses of the CPW. Step S604 corresponds to the first and second peak-interval determining means 680, 682.

Figure 25:
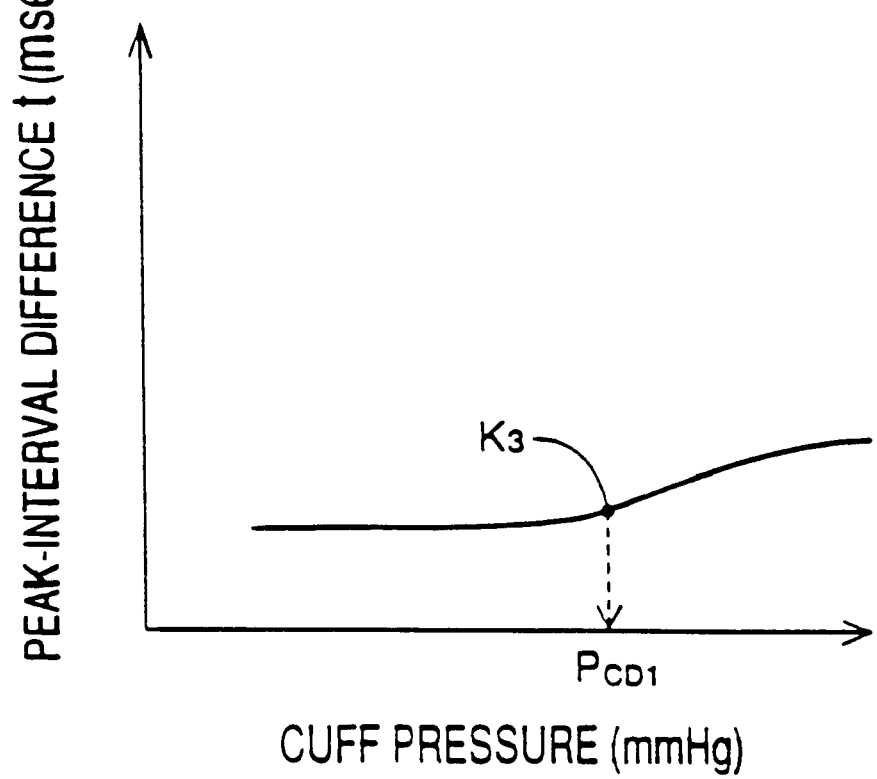
FIG. 25 is a graph showing a relationship between peak-interval difference t and cuff pressure that is determined by the control device of the BP monitor of FIG. 22.

Step S604 is followed by Step S605 to calculate a difference, $t_i$ (=$d_i$−$D_i$, msec), between the first interval $D_i$ of each of the heartbeat-synchronous pulses of the PPW and the second interval $d_i$ of a corresponding one of the heartbeat-synchronous pulses of the CPW which is produced in synchronism with that each pulse of the PPW in response to the same heartbeat. Step S605 corresponds to the difference determining means 684. Step S605 is followed by Step S606 to judge whether the CPU 129 has identified a time when the differences $t_i$ have significantly largely changed. For example, the CPU 129 differentiates the difference values $t_i$ and determines a point, $K_3$, corresponding to the greatest differential, as illustrated in FIG. 25. When the cuff pressure takes values between the systolic and diastolic BP values of the patient, the lower-peak portion of the waveform of each pulse of the PPW signal $SM_2$ is cut off. The point $K_3$ is indicative of a time when the cuff pressure is equal to an actual diastolic BP value of the patient. If a positive judgment is made at Step S606, the control goes to Step S105 to determine a cuff pressure $P_{CD1}$ corresponding to the point $K_3$ identified at Step S606 and store it in a RAM 133. Thus, the cuff pressure $P_{CD1}$ is indicative of an actual diastolic BP value of the patient. In the present embodiment, Step S105 corresponds to a diastolic pressure determining means.

Step S105 is followed by Step S106 to judge whether the current MBP-$P_M$ relationship determined at Step S108 is accurate or appropriate, based on the last diastolic BP value $MBP_{DIA}$ determined at Step S111 and the cuff pressure $P_{CD1}$ stored at Step S105. For example, the CPU 129 judges whether the absolute value of the difference of the last diastolic BP value $MBP_{DIA}$ and the cuff pressure $P_{CD1}$, i.e., $|MBP_{DIA} - P_{CD1}|$, is not greater than a reference value, $\Delta P_1$. This reference value is, e.g., 5 mmHg. Step S106 corresponds to the judging means 686.

As is apparent from the foregoing description relating to the seventh embodiment shown in FIGS. 22 to 25, the CPU 129 of the control device 128 determines, at Step S604, a time interval $D_i$ between an upper-peak point $P_{M2max}$ and a lower-peak point $P_{M2min}$ of each of successive heartbeat-synchronous pulses of the PPW and a time interval $d_i$ between an upper-peak point $P_{M1max}$ and a lower-peak point $P_{M1min}$ of each of successive heartbeat-synchronous pulses of the CPW. The PPW and the CPW are detected by the PPW sensor 146 and the CPW sensor 114, 124, 130, respectively, when the cuff pressure is increased at a predetermined rate at Step S103. At Step S605, the CPU 129 calculates a peak-interval difference $t_i$ between the first interval $D_i$ of each of the heartbeat-synchronous pulses of the PPW and the second interval $d_i$ of a corresponding one of the heartbeat-synchronous pulses of the CPW which is produced in synchronism with that each pulse of the PPW in response to the same heartbeat. At Step S105, the CPU 129 determines, as a diastolic BP value of the patient, a cuff pressure $P_{CD1}$ corresponding to the point $K_3$ is identified at Step S606. At Step S106, the CPU 129 judges whether the MBP-$P_M$ relationship determined at Step S108 is accurate, based on the last diastolic BP value $MBP_{DIA}$ determined at Step S111 and the cuff pressure $P_{CD1}$ stored at Step S105.

If a positive judgment is made at Step S106, an oscillometric BP measuring operation is not carried out at Step S107 and the current relationship is maintained without being updated at Step S108. Thus, the patient is prevented from being pressed by the cuff 110. In addition, although the PPW sensor 146 is worn at a position downstream of the cuff 110, a continuous BP monitoring operation may be continued at Steps S109–S111, without being interrupted due to the inflation of the cuff 110.

Figure 23:
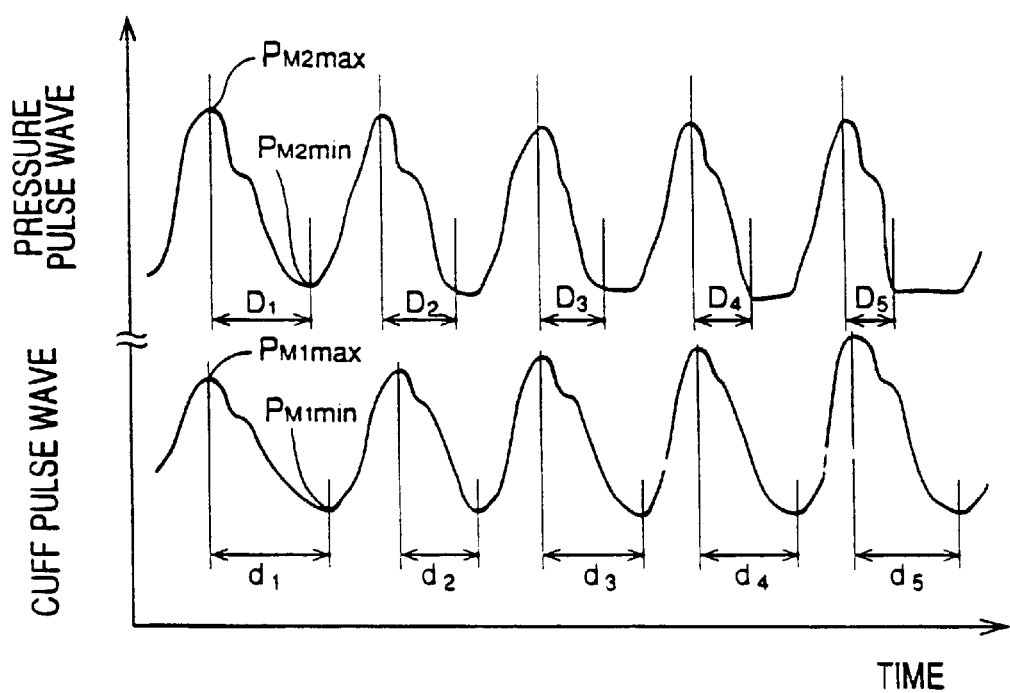
FIG. 23 is a graph showing an example of a cuff pulse wave (CPW) detected by a CPW sensor, and an example of a pressure pulse wave (PPW) detected by a PPW sensor, of the BP monitor of FIG. 22.

In the seventh embodiment, the upper-peak and lower-peak points of each pulse of the CPW are not influenced by the increasing of the cuff pressure, whereas the upper-peak and lower-peak points of each pulse of the PPW are influenced by the increasing of the cuff pressure, as shown in FIG. 23, because the PPW sensor 146 is set on the distal side of the cuff 110. Therefore, the peak-interval differences $t_i$ are influenced by the increasing of the cuff pressure. Thus, a cuff pressure corresponding to the point $K_3$ where the differences $t_i$ significantly largely change, is equal to a diastolic BP value of the patient. Accordingly, the accuracy of the MBP-$P_M$ relationship can be judged by increasing the cuff pressure up to a value around the diastolic BP value of the patient, which does not cause the patient to feel discomfort. In addition, in the case where a physiological change such as arrhythmia occurs to the heart of the patient, respective waveforms of the CPW and the PPW change in a similar manner, so that the peak-interval differences $t_i$ are not influenced by this change. Thus, the accuracy of the MBP-$P_M$ relationship can be judged with high reliability.

In the seventh embodiment, since the judgment about whether the MBP-$P_M$ relationship is accurate is made based on the cuff pressure $P_{CD1}$ and the last diastolic BP value $MBP_{DIA}$ determined at Step S111, it is more accurate than a judgment made based on a diastolic BP value $MBP_{DIA}$ determined at Step S111 a predetermined time before, or the last diastolic BP value $BP_{DIA}$ measured at Step S107.

Figure 26:
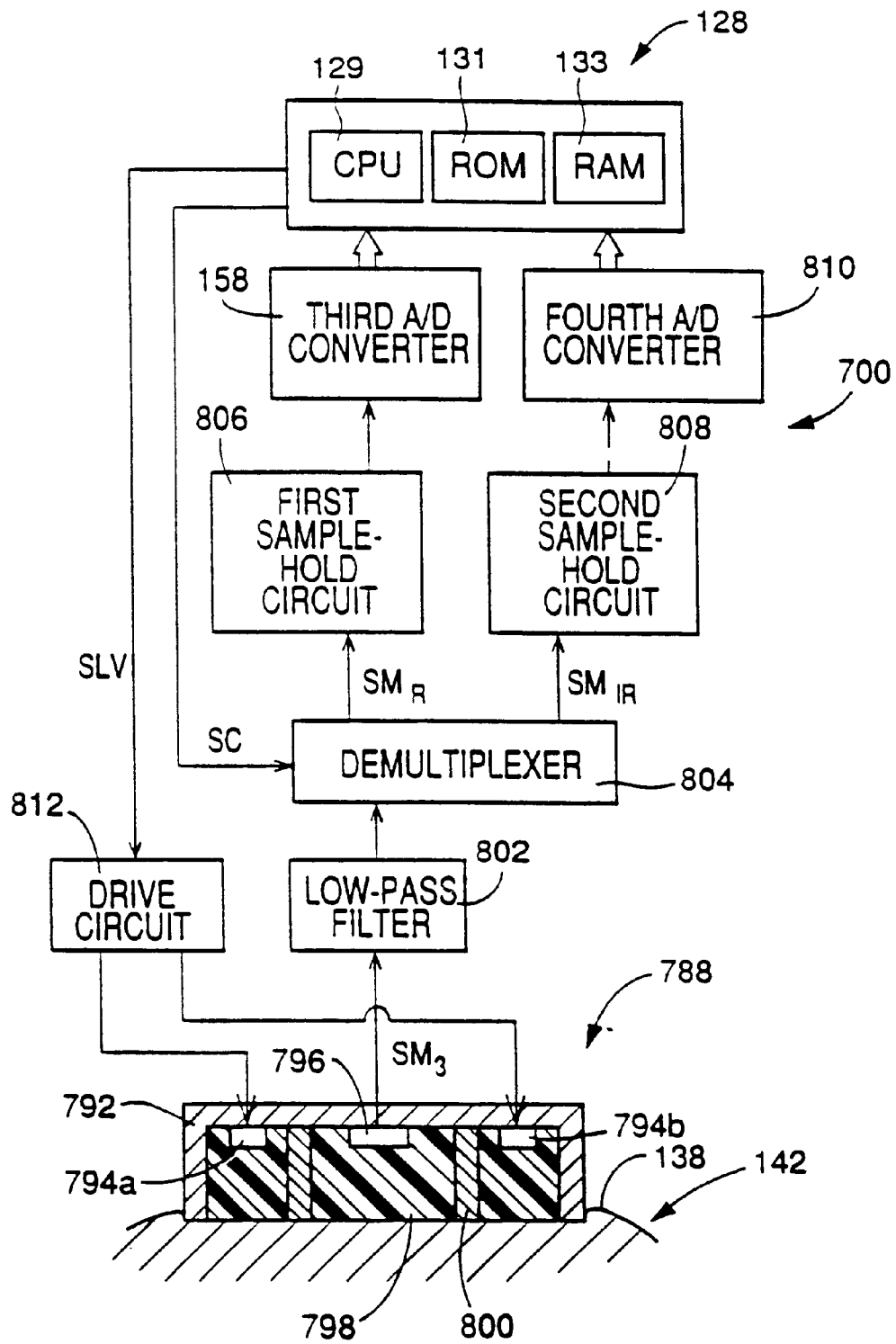
FIG. 26 is a diagrammatic view corresponding to FIG. 7, showing a part of a BP monitor as an eighth embodiment of the present invention.
Figure 27:
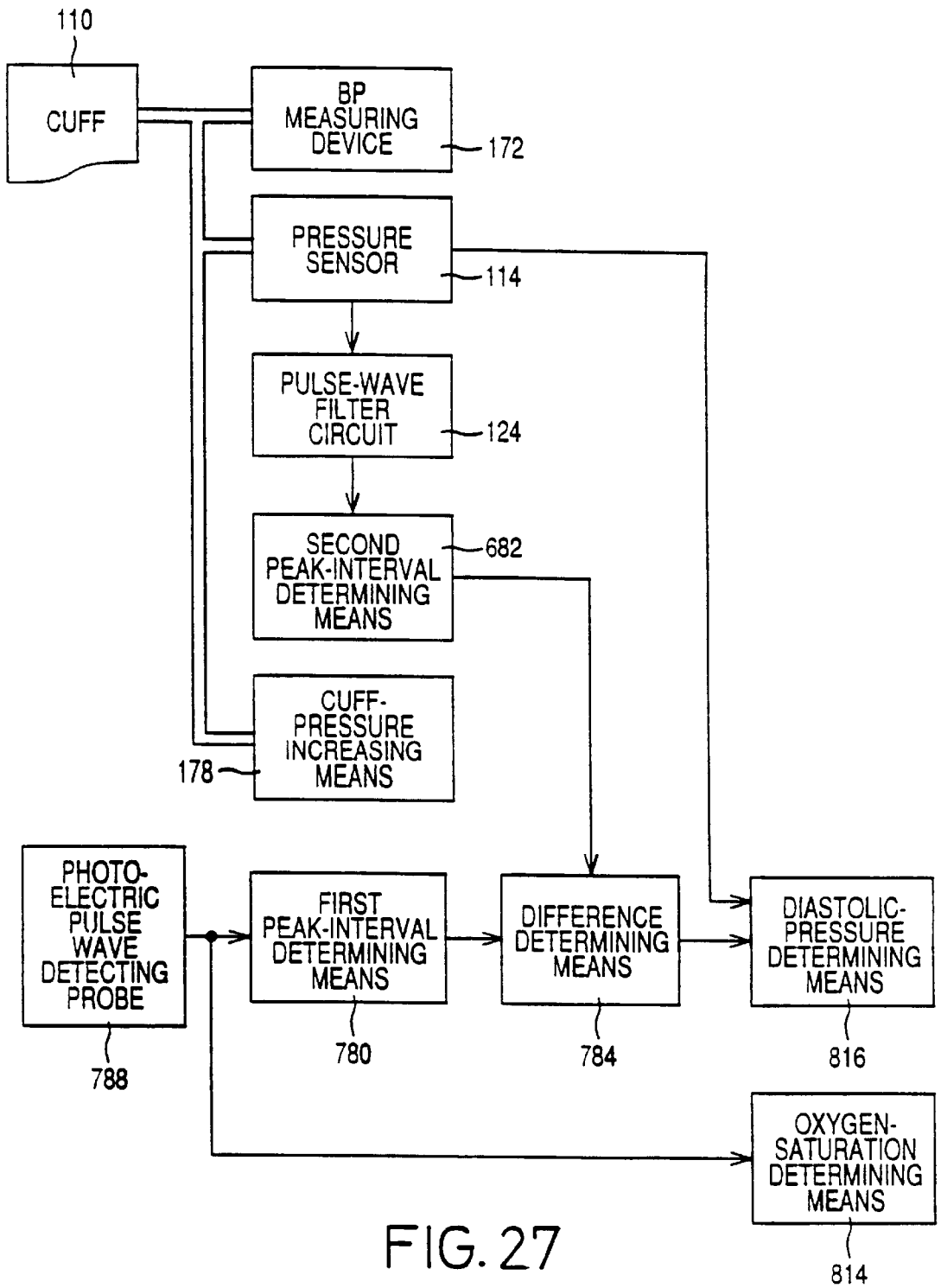
FIG. 27 is an illustrative view corresponding to FIG. 10, for explaining various functions of a control device of the BP monitor of FIG. 26.
Figure 28:
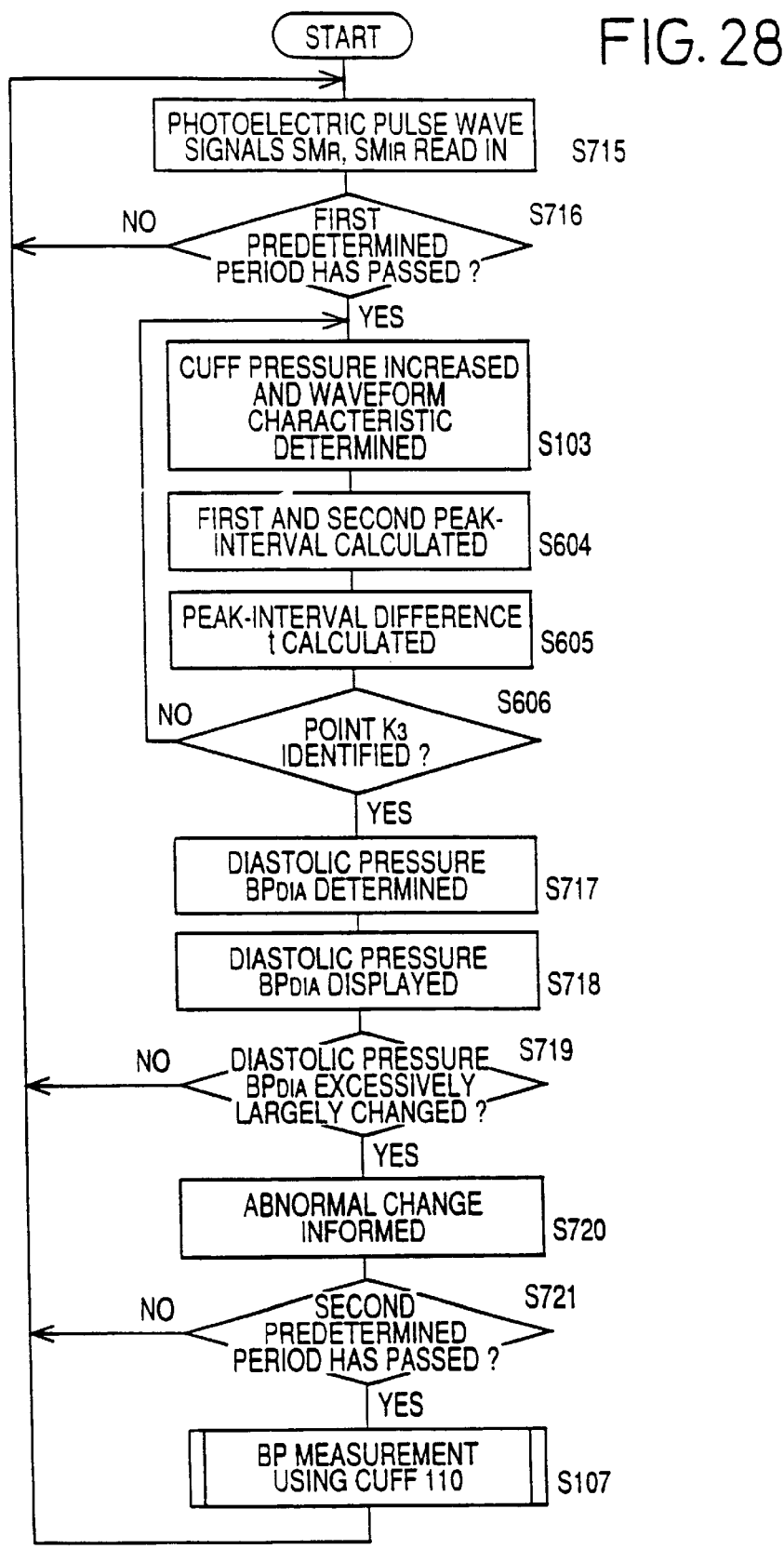
FIG. 28 is a flow chart representing a control routine according to which the BP monitor of FIG. 26 operates.

Referring next to FIGS. 26 through 28, there will be described an eighth embodiment of the present invention. The eighth embodiment relates to a BP monitor 700 having a hardware construction basically similar to that of the second embodiment shown in FIG. 7 and including a photoelectric pulse wave detecting probe 788 in place of the PPW detecting probe 134 of the second embodiment. The same reference numerals as used in the second embodiment are used to designate the corresponding elements or parts of the eighth embodiment and the description thereof is omitted.

The probe 788 is held, with the help of a band (not shown), in close contact with a body surface 138 of a wrist 142 of a patient located on a distal side of an inflatable cuff 110 being wound around an upper arm 112 of so the patient. The probe 788 includes a container-like cylindrical housing 792 having a circular bottom wall and a circular opening; a plurality of first light emitting elements 794a (e.g., light emitting diodes (LEDs)) and a plurality of second light emitting elements 794b which are secured to an outer annular portion of the bottom wall of the housing 792; a light detecting element (e.g., photo diode or photo transistor) which is secured to a central portion of the bottom wall of the housing 792; a transparent resin 798 which covers the light emitting elements 794 (794a, 794b) and the light detecting element 796 and fills the spaces left in the housing 792; and a cylindrical light-shading member 800 which prevents the lights emitted from the light emitting members 794 and reflected by the body surface 138, from being received by the light detecting element 796.

The first light emitting elements 794a emit a red light having, e.g., a 660 nm wavelength, and the second light emitting elements 794b emit an infra-red light having, e.g., a 800 nm wavelength. Various pairs of lights each pair of which have different wavelengths may be employed in place of the 660 nm and 800 nm wavelength lights, so long as one light of each pair exhibits significantly different absorption factors with respect to hemoglobin and oxygenated hemoglobin, respectively, and the other light exhibits substantially the same absorption factors with respect to the two sorts of hemoglobin, respectively. The first light emitting elements 794a and the second light emitting elements 794b alternately and periodically emit the red and infrared lights, respectively, such that each light emission lasts a predetermined, very short duration of time. The red and infrared lights emitted from the first and second light emitting elements 794a, 794b are reflected from a blood-vessel bed under the body surface 138, and the reflected lights are detected by the common light detecting element 796.

The light detector 796 generates a photoelectric pulse wave signal (electric signal), $SM_3$, whose magnitude corresponds to the detected intensity of a reflected red or infrared light, to a low-pass filter 802 via an amplifier (not shown). The magnitude of the signal $SM_3$ is variable because of the pulsation of blood in the blood vessels under the body surface 138. The low-pass filter 802 clears the signal $SM_3$ of noise whose frequencies are higher than the frequency of the blood pulsation, and supplies the cleared signal $SM_3$ to a demultiplexer 804. The demultiplexer 804 is selectively placed in a first and a second state thereof according to a switch signal, SC, (described below), supplied from a control device 128, in synchronism with the alternate and periodic light emissions from the first and second light emitters 794a, 794b. More specifically described, when the first light emitters 794a emit a red light, the demultiplexer 804 is placed in the first state in which the demultiplexer 804 permits an electric signal, $SM_R$, representing the detected intensity of the reflected red light, to be supplied to an input and output (I/O) port (not shown) of the control device 128 via a first sample-hold circuit 806 and a third A/D converter 158; and when the second light emitters 794b emit an infrared light, the demultiplexer 804 is placed in the second state in which the demultiplexer 804 permits an electric signal, $SM_{IR}$, representing the detected intensity of the reflected infrared light, to be supplied to the I/O port of the control device 128 via a second sample-hold circuit 808 and a fourth A/D converter 810. The first and second sample-hold circuits 806, 808 supply the signals $SM_R$, $SM_{IR}$ to the third and fourth A/D converters 158, 810, respectively, such that the circuits 806, 808 continue to hold the signals $SM_R$, $SM_{IR}$ received in a current cycle until the converters 158, 810 complete the respective analog to digital conversions of the signals $SM_R$, $SM_{IR}$ which in the preceding cycle the circuits 806, 808 have supplied to the converters 158, 810, respectively. In the present embodiment, the photoelectric pulse wave detecting probe 788 provides a distal pulse wave sensor which is adapted to be set on the distal side of the cuff 110.

In the present embodiment, a first and a second A/D converter 126, 130, a display 132, etc. are connected to the control device 128, like in the second embodiment shown in FIG. 7. However, the second air pump 150 or the pressure regulator valve 152 is not employed.

A CPU 129 of the control device 128 generates a light-emission control signal, SLV, to a drive circuit 812 so that the first and second light emitters 794a, 794b alternately and periodically emit the red and infrared lights, respectively. In synchronism with the alternate and periodic light emissions from the first and second light emitters 794a, 794b, the CPU 129 generates the switch signal SC to the demultiplexer 804 so as to place correspondingly the demultiplexer 804 in the first or second state. Thus, the photoelectric pulse wave signal $SM_3$ is separated by the demultiplexer 804 such that the red-light signal $SM_R$ is supplied to the first sample-hold circuit 806 and the infrared-light signal $SM_{IR}$ is supplied to the second sample-hold circuit 808.

In addition, the CPU 129 processes the input signals $SM_R$, $SM_{IR}$ supplied from the third and fourth A/D converters 158, 810, according to a control program pre-stored in a ROM 131, and determines an oxygen saturation of the blood flowing through the blood vessels under the body surface 138, based on the respective waveforms of the signals $SM_R$, $SM_{IR}$. The CPU 129 commands the display 132 to display the determined blood oxygen saturation. The manner of determination of the blood oxygen saturation employed in the present embodiment is the same as that disclosed in, e.g., U.S. Pat. No. 5,131,391 assigned to the Assignee of the present application. The disclosure of this patent is incorporated herein by reference. In short, the CPU 129 determines a blood oxygen saturation of a patient based on a ratio, A/B, according to a predetermined relationship between ratio A/B and blood oxygen saturation, where $A=(V_{dR}-V_{sR})/(V_{dR}+V_{sR})$, and $B=(V_{dIR}-V_{sIR})/(V_{dIR}+V_{sIR})$. The signal $SM_3$ has a waveform similar to that shown in the top of the graph of FIG. 23. The values $V_{dR}$, $V_{sR}$ are an upper-peak and a lower-peak magnitude of each pulse of the red-light signal $SM_R$, and the values $V_{dIR}$, $V_{sIR}$ are an upper-peak and a lower-peak magnitude of each pulse of the infrared-light signal $SM_{IR}$.

As shown in FIG. 27, the BP monitor 700 has different functions from those of the BP monitor 100 as the second embodiment. A control device 128 of the BP monitor 700 functions as a second peak-interval determining means 682 that is the same as the means 682 of the BP monitor 600 shown in FIG. 22. The second peak-interval determining means 682 determines a second interval between an upper-peak point and a lower-peak point of each pulse of a CPW signal $SM_1$ supplied from a pulse-wave filter circuit 124.

The CPU 129 also functions as an oxygen-saturation determining means 814 which determines a blood oxygen saturation of a patient based on the photoelectric pulse wave signal $SM_3$ supplied from the probe 788. Moreover, the CPU 129 functions as a first peak-interval determining means 780 which determines a first interval between an upper-peak point and a lower-peak point of each pulse of the signal $SM_3$; and a difference determining means 784 which determines a difference, t, between the first interval of each of the successive heartbeat-synchronous pulse of the photoelectric pulse wave and the second interval of a corresponding one of the successive heartbeat-synchronous pulses of the cuff pulse wave; and a diastolic-pressure determining means 816 which determines, as a diastolic pressure of the patient, a cuff pressure CD1 corresponding to a point $K_3$ or time when the differences t determined by the difference determining means 784 significantly largely change.

FIG. 28 shows a flow chart representing a control program according to which the control device 128 controls the operation of the present BP monitor 700. Steps S103 and Step S107 of the flow chart of FIG. 28 are the same as Steps S103 and Step S107 of the flow chart of FIG. 11, and Steps S604, S605, and S606 of the flow chart of FIG. 28 are the same as Steps S604, S605, and Step S606 of the flow chart of FIG. 24, and the description of those steps is omitted, if appropriate.

Initially, at Step S715, the CPU 129 reads in each heartbeat-synchronous pulse of the red-light signal $SM_R$ and each heartbeat-synchronous pulse of the infra-red signal $SM_{IR}$, from the photoelectric pulse wave detecting probe 788. On one hand, those pulses are used for determining a blood oxygen saturation of the patient as described above and, on the other hand, the same pulses are processed according to Step S716 and the following steps of the flow chart of FIG. 28.

At Step S716, the CPU 129 judges whether a predetermined first period has passed after a diastolic pressure $BP_{DIA}$ is determined at Step S717 in the preceding control cycle. The first period may be predetermined (e.g., selected) at an appropriate time by an operator. If a negative judgment is made at Step S716, the control of the CPU 129 goes back to Step S715 to read in the signals $SM_R$, $SM_{IR}$. Meanwhile, if a positive judgment is made at Step S716, the control of the CPU 129 proceeds with Steps S103, S604, S605, and S606 that are the same as Steps S103, S604, S605, and S606 of the flow chart of FIG. 24, except that in the eighth embodiment the signal $SM_3$ ($SM_R$ or $SM_{IR}$) is employed in place of the PPW signal $SM_2$.

If a point $K_3$ is identified as shown in FIG. 25 and a positive judgment is made at Step S606, the control of the CPU 129 goes to Step S717 to determine, as a diastolic pressure $BP_{DIA}$ of the patient, a cuff pressure $P_{CD1}$ corresponding to the point $K_3$, i.e., time when the peak-interval differences $t_i$ determined at Step S605 significantly largely change. Step S717 is followed by Step S718 to command the display 132 to display the determined diastolic pressure $BP_{DIA}$.

Subsequently, the control of the CPU 129 goes to Step S719 to judge whether the diastolic-pressure value $BP_{DIA}$ determined at Step S718 in the current control cycle is higher than a reference value which is predetermined to be higher by an excess value than a moving average of a predetermined number of prior diastolic-pressure values $BP_{DIA}$ determined in the same number of prior control cycles. If a positive judgment is made at Step S719, the control goes to Step S720 to command the display 132 to display an informing message that the diastolic pressure $BP_{DIA}$ of the patient is abnormal. On the other hand, if a negative judgment is made at Step S719, the control goes back to Step S715. Step S720 is followed by Step S721 to judge whether a second predetermined period has passed after a systolic, a mean, and a diastolic BP value $BP_{SYS}$, $BP_{MEAN}$, $BP_{DIA}$ are measured using the cuff 110 according to the oscillometric method, at Step S107 in the prior control cycle. The second period may be predetermined independent of the first period. However, the second period is predetermined to be not shorter than the shortest BP measurement period (2 minutes and 30 seconds) specified by WHO (World Health Organization). If a negative judgment is made at Step S721, the control goes back to Step S715 so that another diastolic pressure can be measured while the display 132 continues to display the "abnormality" message. On the other hand, if a positive judgment is made at Step S721, the control goes to Step S107 to continue to increase the cuff pressure so that BP values $BP_{SYS}$, $BP_{MEAN}$, $BP_{DIA}$ are measured according to the oscillometric method. Then, the control of the CPU 129 goes back to Step S715.

As is apparent from the foregoing description relating to the eighth embodiment shown in FIGS. 26 to 28, the CPU 129 of the control device 128 determines, at Step S605, a time interval $D_i$ between an upper-peak point $V_{sR}$ or $V_{sIR}$ and a lower-peak point $V_{dR}$ or $V_{dIR}$ of each of successive heartbeat-synchronous pulses of the red-light or infrared-light signal $SM_R$ or $SM_{IR}$ and a time interval $d_i$ between an upper-peak point $P_{M1max}$ and a lower-peak point $P_{M1min}$ of each of successive heartbeat-synchronous pulses of the CPW signal $SM_1$. The signal $SM_R$ or $SM_{IR}$ and the signal $SM_1$ are detected by the probe 788 and the CPW sensor 114, 124, 130 respectively, when the cuff pressure is increased at a predetermined rate at Step S103. At Step S605, the CPU 129 calculates a peak-interval difference $t_i$ between the first interval $D_i$ of each of the heartbeat-synchronous pulses of the signal $SM_R$ or $SM_{IR}$ and the second interval $d_i$ of a corresponding one of the heartbeat-synchronous pulses of the CPW signal $SM_1$ which is produced in synchronism with that each pulse of the signal $SM_R$ or $SM_{IR}$ in response to the same heartbeat. At Step S606, the CPU 129 identifies a point $K_3$ where the rate of change of the peak-interval differences $t_i$ significantly largely change. At Step S717, the CPU 129 determines, as a diastolic BP value $BP_{DIA}$ of the patient, a cuff pressure $P_{CD1}$ corresponding to the point $K_3$ identified at Step S606, and commands the display 132 to display the determined diastolic pressure $BP_{DIA}$. At Step S719, the CPU 129 judges whether the diastolic-pressure value $BP_{DIA}$ is abnormal, based on the amount of change of it from the prior diastolic-pressure values $BP_{DIA}$.

If a negative judgment is made at Step S719, an oscillometric BP measuring operation is not carried out at Step S107. Thus, the present BP monitor 700 can monitor the blood pressure of the patient without causing the patient to feel the discomfort due to highly frequent pressing of the cuff 110. In the present embodiment, the photoelectric pulse wave detecting probe 788 is used for not only monitoring the blood oxygen saturation of the patient but also the blood pressure of the patient. Thus, the total number of sensors which are worn on the patient is reduced as compared with the case where an exclusive distal pulse wave sensor is employed.

Although the probe 788 is worn at a position downstream of the cuff 110, a continuous blood oxygen saturation monitoring operation using the probe 788 may be continued without being interrupted due to the inflation of the cuff 110 at Step S103, because in a continuous BP monitoring operation the cuff pressure is not increased to values higher than the diastolic pressure of the patient.

When the display 132 informs the operator of the abnormal change of the diastolic pressure $BP_{DIA}$ of the patient, he or she can take an appropriate action against it. Even in this case, the oscillometric BP measurement is not carried out at Step S107, before the second predetermined period has-passed at Step S721. Therefore, the patient is prevented from being highly frequently pressed by the cuff 110.

In each of the seventh and eighth embodiments, the BP measuring device 172 performs, at Step S107, an oscillometric BP measuring method in which one or more BP values are determined based on the variation of respective amplitudes of heartbeat-synchronous pulses of the cuff pulse wave (i.e., CPW signal $SM_1$) obtained while the cuff pressure is changed. However, it is possible to employ, in place of the oscillometric method, a Korotkoff-sound method in which one or more BP values are determined based on the first detection and/or last detection (i.e., disappearance) of Korotkoff sounds detected by a microphone while the cuff pressure is changed.

While in the seventh embodiment the judging means 686 uses only the last diastolic BP value $MBP_{DIA}$ determined by the monitor-BP determining means 176, for evaluating the accuracy of the MBP-$P_M$ relationship, it is possible to use, for the same purpose, an average of a plurality of last diastolic BP values $MBP_{DIA}$ determined based on a plurality of last pulses detected by the PPW sensor 146. In the latter case, even if an abnormal lower-peak magnitude of a PPW pulse may be detected due to, e.g., a physical motion of the patient, the adverse influence of that magnitude to the judgment of the judging means 686 is effectively reduced.

Although in the seventh embodiment the calibration of the MBP-$P_M$ relationship is carried out at Steps S107 and S108 at a predetermined period employed at Step S112, it is possible to replace Step S112 by a step where the CPU 129 judges whether monitor BP values MBP determined by the BP determining means 176 have abnormally changed. In the latter case, if a positive judgment is made at that step, then the control of the CPU 129 goes back to Step S102.

While in each of the seventh and eighth embodiments the cuff 110 is adapted to be wound around the upper arm 112 of the patient, it is possible to employ an inflatable cuff which is adapted to be wound around a different body portion of a patient such as a wrist.

In the eighth embodiment, it is possible to omit Step S107 from the flow chart of FIG. 28. In the latter case, if a positive judgment is made at Step S719, the CPU 129 only commands, at Step S720, the display 132 to display the "abnormality" message. Alternatively, it is possible to omit Step S720 from the flow chart of FIG. 28. In the last case, if a positive judgment is made at Step S719, the CPU 129 is only able to command, at Step S107, the BP measuring device 172 to carry out an oscillometric BP measurement using the cuff 110. The reference value employed at Step S719 for finding an abnormal diastolic pressure $BP_{DIA}$ may be predetermined in a manner other than described therein.

In the eighth embodiment, the first period used at Step S716 may be predetermined to be longer than the second period used at Step S721. In the latter case, it is possible to omit Step S721. In the last case, whenever a positive judgment is made at Step S719, the CPU 129 commands, at Step S107, the BP measuring device 172 to carry out an oscillometric BP measurement using the cuff 110.

While in the eighth embodiment the reflection-type probe 788 that detects the lights reflected from the blood vessels under the body surface 138 of the patient is employed, it is possible to employ a transmission-type probe that detects the lights transmitted through the body portion or tissue 142 of the patient.

In each of the seventh and eighth embodiments, the PPW sensor 146 or the probe 788 may be replaced by a different sort of pulse wave sensor, e.g., an impedance sensor which detects the change of impedance of a living subject due to blood pulsation and which is used in the so-called impedance plethysmography.

In the eighth embodiment, the probe 788 is employed for monitoring both the blood pressure and blood oxygen saturation of a living subject. However, it is possible to employ, in place of the probe 788, an exclusive sensor which detects a photoelectric pulse wave for exclusively monitoring the blood pressure of a living subject, or a sensor which detects a photoelectric pulse wave for monitoring both the blood pressure and peripheral blood circulation of a living subject.

It is to be understood that the present invention may be embodied with other changes, improvements, and modifications that may occur to those skilled in the art without departing from the spirit and scope of the invention defined in the appended claims.

What is claimed is:

1. A blood pressure monitor comprising:

an inflatable cuff which is adapted to be wound around a body portion of a living subject to press said body portion through which an artery of the subject extends;

a blood pressure measuring device which measures a blood pressure of the subject by changing a pressure in said cuff;

a pressure pulse wave sensor which is adapted to be pressed against a distal section of said artery located on a distal side of said cuff wound around said body portion, so as to detect a pressure pulse wave which is produced from said distal section of the artery and is propagated thereto via a skin tissue above said distal section;

relationship determining means for determining a relationship between blood pressure and magnitude of pressure pulse wave, based on the blood pressure measured by said blood pressure measuring device and a magnitude of the pressure pulse wave detected by said pressure pulse wave sensor;

blood pressure determining means for determining at least a mean blood pressure of the subject according to the determined relationship based on a mean magnitude of each of successive first heartbeat-synchronous pulses of said pressure pulse wave detected by said pressure pulse wave sensor;

cuff-pressure increasing means for increasing said pressure of said cuff at a predetermined rate;

pulse-area calculating means for calculating an area defined by each of successive second heartbeat-synchronous pulses of said pressure pulse wave which are detected by said pressure pulse wave sensor when said pressure of said cuff is increased at said predetermined rate by said cuff-pressure increasing means;

half-area identifying means for identifying that the pulse area calculated by said pulse-area calculating means has decreased to half an initial pulse area obtained before said cuff-pressure increasing means starts increasing said pressure of said cuff; and judging means for judging whether said determined relationship is accurate, based on at least one mean blood pressure determined by said blood pressure determining means and a pressure of said cuff corresponding to a time when said half-area identifying means identifies that the pulse area calculated by said pulse-area calculating means has decreased to half said initial pulse area.

* * * * *